(12) United States Patent
Kitano et al.

(10) Patent No.: US 7,294,629 B2
(45) Date of Patent: Nov. 13, 2007

(54) QUINAZOLINE DERIVATIVES

(75) Inventors: Yasunori Kitano, Tokyo (JP); Eiji Kawahara, Suita (JP); Tsuyoshi Suzuki, Tokyo (JP); Daisuke Abe, Tokyo (JP); Masahiro Nakajou, Tokyo (JP); Naoko Ueda, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 704 days.

(21) Appl. No.: 10/468,788

(22) PCT Filed: Feb. 21, 2002

(86) PCT No.: PCT/JP02/01575

§ 371 (c)(1),
(2), (4) Date: Aug. 21, 2003

(87) PCT Pub. No.: WO02/066445

PCT Pub. Date: Aug. 29, 2002

(65) Prior Publication Data

US 2004/0116422 A1    Jun. 17, 2004

(30) Foreign Application Priority Data

Feb. 21, 2001 (JP) ............... 2001-045827
Nov. 19, 2001 (JP) ............... 2001-353525

(51) Int. Cl.
A61K 31/517 (2006.01)
C07D 239/94 (2006.01)
A61K 31/54 (2006.01)
A61K 31/5377 (2006.01)

(52) U.S. Cl. ............ 514/252.17; 514/217.06; 514/218; 514/228.2; 514/234.5; 514/266.2; 514/266.4; 540/575; 540/600; 544/58.2; 544/58.6; 544/119; 544/293

(58) Field of Classification Search ............ 514/266.2, 514/266.4, 252.17, 217.06, 218, 228.2, 234.5; 544/293, 58.2, 58.6, 119; 540/575, 600
See application file for complete search history.

(56) References Cited

U.S. PATENT DOCUMENTS 6,127,374 A * 10/2000 Bridges ............ 514/217.06
6,251,912 B1 * 6/2001 Wissner et al. ........ 514/228.2

FOREIGN PATENT DOCUMENTS

| EP | 0 837 063 | | 4/1998 |
| EP | 1690856 | * | 8/2006 |
| JP | 05-208991 | | 8/1993 |
| JP | 06-073025 | | 3/1994 |
| JP | 10-152477 | | 6/1998 |
| WO | 97/38983 | | 10/1997 |

OTHER PUBLICATIONS

Vippagunta, S.R. et. al., Crystalline Solids, Advanced Drug Delivery Reviews, 2001, vol. 48, pp. 3-26.*
P. Perrotte et al., "Anti-Epidermal Growth Factor Receptor Antibody C225 Inhibits Angiogenesis in Human Transitional Cell Carcinoma Growing Orthotopically in Nude Mice", Clinical Cancer Research, vol. 5, pp. 257-264, Feb. 1999.
D. W. Fry, "Protein tyrosine kinases as therapeutic targets in cancer chemotherapy and recent advances in the development of new inhibitors", Exp. Opin. Invest. Drugs, vol. 3, No. 6, 1994, pp. 577-595.
T. Hunter, "A thousand and one protein kinases", Cell, vol. 50, Sep. 11, 1987, pp. 823-829.
T. Yoneda et al., "The antiproliferative effects of tyrosine kinase inhibitors tyrphostins on a human squamous cell carcinoma in vitro and in nude mice", Cancer Research, vol. 51, Aug. 15, 1991, pp. 4430-4435.
K. B. Reddy et al., "Inhibition of breast cancer cell growth in vitro by a tyrosine kinase inhibitor", Cancer Research, vol. 52, Jul. 1, 1992, pp. 3636-3641.
V. Brunton et al., "Cell-signaling targets for antitumour drug development", Cancer Chemother Pharmacol., vol. 32, 1993, pp. 1-19.

(Continued)

Primary Examiner—James O. Wilson
Assistant Examiner—Tamthom N Truong
(74) Attorney, Agent, or Firm—Wenderoth, Lind & Ponack, L.L.P.

(57) ABSTRACT

A compound of the formula (I)

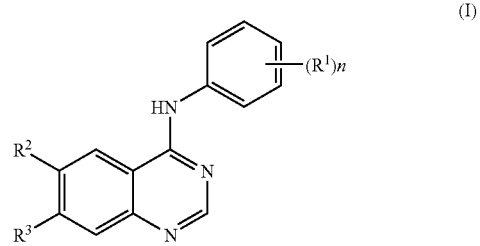

or a pharmaceutically acceptable salt thereof, a hydrate thereof, a solvate thereof, an optically active compound thereof, a racemate thereof or a diastereomer mixture thereof has a superior tyrosine-specific protein kinase inhibitory activity and is useful as a pharmaceutical agent, particularly as an agent for the prophylaxis or treatment of various cancers, psoriasis or diseases caused by arteriosclerosis, and the like.

9 Claims, 2 Drawing Sheets

OTHER PUBLICATIONS

W.J. Gullick et al., "Prevalence of aberrant expression of the epidermal growth factor receptor in human cancers", Medical Bulletin, vol. 47, No. 1, 1991, pp. 87-98.

J. Nelson et al., "Murine epidermal growth factor (EGF) fragment (33-42) inhibits both EGF- and laminin-dependent endothelial cell motility and angiogenesis", Cancer Research, vol. 55, Sep. 1, 1995, pp. 3772-3776.

D. Boschelli, "Small molecule inhibitors of receptor tyrosine kinases", Drugs of the Future, vol. 24, No. 5, 1999, pp. 515-537.

P. Perrotte et al., "Anti-epidermal growth factor receptor antibody C225 inhibits angiogenesis in human transitional cell carcinoma growing orthotopically in nude mice", Clinical Cancer Research, vol. 5, Feb. 199, pp. 257-264.

G. Bilder et al., "Tyrphostins inhibit PDGF-induced DNA synthesis and associated early events in smooth muscle cells", Am. J. Physiol., 1991, vol. 260 (4-part-1), C721-C730.

L. Merkel et al., "Inhibition of EGF—Induced Vasoconstriction in Isolated Rabbit Aortic Rings with the Tyrosine Kinase Inhibitor RG50864", Biochem. Biophys. Res. Commun., vol. 192, No. 3, May 14, 1993, pp. 1319-1326.

H. Salari et al.,"Erbstatin blocks platelet activating factor-induced protein-tyrosine phosphorylation, polyphosphoinositide hydrolysis, protein kinase C activation, seratonin secretion and aggregation of rabbit platelets", FEBS Letters, Apr. 1990, vol. 263, No. 1, pp. 104-108.

M. Asahi et al., "Thrombin-induced human platelet aggregation is inhibited by protein-tyrosine kinase inhibitors, ST638 and genistein", FEBS Letters, vol. 309, No. 1, Aug. 1992, pp. 10-14.

E. Munoz et al., "Tyrosine protein phosphorylation is required for protein kinase C-mediated proliferation in T cells", FEBS Letters, vol. 279, No. 2, Feb. 1991, pp. 319-322.

A. O'Rourke et al., "Cytotoxic T-lymphocyte activation involves a cascade of signaling and adhesion events", Nature, vol. 358, Jul. 16, 1992, pp. 253-255.

C. E. Klein et al., "Expression of a 38-kD Cell-Surface Glycoprotein in Transformed Human Keratinocyte Cell Lines", Basal Cell Carcinomas, and Epithelial Germs, J. Invest. Dermatol., vol. 95, 1990, pp. 74-82, pp. 83-89 and 90-96.

C. Roifman et al., "Tyrosine phospharylation is an essential event in the stimulation of B lymphocytes by *Stephylococcus aureus* cowan I", The Journal of Immunology, vol. 146, No. 9, May 1, 1991, pp. 2965-2971.

A. Dhar et al., "Platelet-activating factor stimulation of thyrosine kinases and its relationship to phospholipase C in rabbit platelets: studies with genistein and monoclonal antibody to phosphatyrosine", Molecular Pharmacology, vol. 37, 1990, pp. 519-525.

H. Schneider et al., "Tyrosine phosphorylation of phospholipase $C_y$, couples the Fε receptor mediated signal to mast cells secretion", International Immunology, vol. 4, No. 4, 1992, pp. 447-453.

* cited by examiner

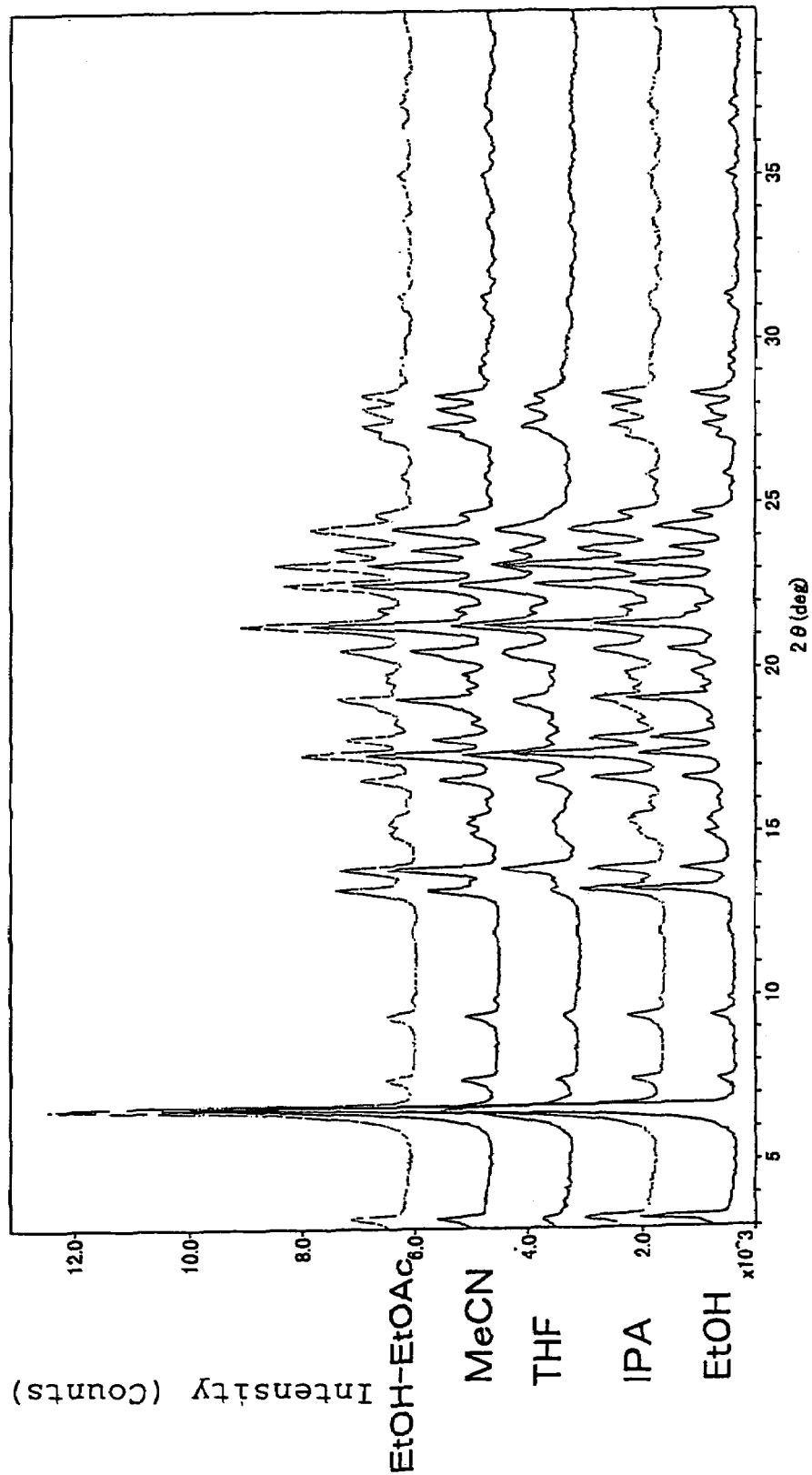

QUINAZOLINE DERIVATIVES

This application is a U.S. national stage of International Application No. PCT/JP02/01575 filed Feb. 21, 2002.

TECHNICAL FIELD

The present invention relates to a novel quinazoline derivative. More particularly, the present invention relates to a quinazoline derivative having a tyrosine-specific protein kinase (hereinafter tyrosine kinase) inhibitory activity.

The present invention also relates to a pharmaceutical composition containing said quinazoline derivative and a pharmaceutically acceptable carrier, a tyrosine kinase inhibitor containing said quinazoline derivative, and an anticancer agent and an agent for the treatment and/or prophylaxis of the diseases based on arteriosclerosis and the diseases caused by the potentiation of tyrosine kinase activity, such as psoriasis and the like.

BACKGROUND ART

In chemotherapy of cancer, a number of pharmaceutical agents that inhibit DNA synthesis or that directly inhibit cell division have been used. These pharmaceutical agents function as cytotoxicity, and sometimes prove effective against rapidly dividing cancer cells. In many cases, however, since the cytotoxicity is not limited to cancer cells, they exhibit strong toxicity in normal cells as well. As the current situation stands, therefore, side effects have become a problem in chemotherapy using such pharmaceutical agents. As a different approach acting on a mechanism other than the one mentioned above, a method enhancing the selectivity to suppress growth of cancer cells is known.

Tyrosine kinase is an enzyme that phosphorylates tyrosine residue in proteins. It is widely known that tyrosine kinase plays an important and central role in differentiation and proliferation of cells and in an intracellular signal transduction system. Furthermore, it is also considered that a failure to control tyrosine kinase activity causes aberration in differentiation or proliferation of cells and in an intracellular signal transduction system, thereby directly causing the onset of many diseases. For example, tyrosine kinase activity has been found to be detected more often in arteriosclerosis [*Am. J. Physiol.*, 1991, 260 (4-part 1), C721-C730; *Biochem. Biophys. Res. Commun.*, 1993, 192(3), 1319-1326. etc.] and psoriasis [*J. Invest. Deruatol.*, 1990, 95, 75-95], as well as in tumor cells than in normal cells [*Cell*, 1987, 50, 823]. Particularly, it has been clarified that growth factor receptor tyrosine kinases (hereinafter to be referred to as receptor tyrosine kinase) such as HER2 (also called ErbB2 or Neu), EGF receptor and the like are deeply involved in the formation of malignant tumor, and that receptor tyrosine kinase activity is potentiated in human cancer [*Cancer Res.*, 1991, 51, 4430-4435; *Cancer Res.*, 1992, 52, 3636-3641; *Cancer Chemother. Pharmacol.*, 1993, 32, 1-19 and the like]. Moreover, these receptor tyrosine kinases have been shown to excessively express in many tumors such as those in brain, lung, stomach, colorectum, pancreas, head and neck portion, esophagus, bladder, kidney, prostate, ovary, breast, uterus, thyroid gland and the like [*Med. Bull.*, 1991, 47, 87; *Expert. Opin. Invest. Drugs*, 1994, 3 (6), 577-595; JP-A-5-208911]. In addition, involvement of EGF receptors in angiogenesis, which is closely related to metastasis of cancer, has been indicated [*J. Biol. Chem.*, 1995, 912, 895-898; *Cancer Res.*, 1995, 55, 3772-3776]. Accordingly, a pharmaceutical agent that inhibits tyrosine kinase is considered to be useful not only as an agent for the prophylaxis or treatment of the above-mentioned diseases but also as an anticancer agent having a new mechanism, which is applicable to many kinds of cancers and which causes fewer side effects. Various tyrosine kinase inhibitors have been heretofore studied, and disclosed in JP-A-6-73025, JP-A-5-208911, Japanese Patent No. 2994165, JP-T-Hei 12-508657 and a recent paper by Diane H. Boschelli [*Drugs of the Future* 1999 24(5), 515-537], but have not been put to practical use.

The four receptors of EGF receptor, HER2, ErbB3 and ErbB4 all belong to the ErbB family, and these receptors form a heterocomplex and show interaction in the intracellular signal transduction [*J. Clin. Oncol.* 2001 19(18s), 32s-40s]. For example, it is known that coexpression of EGF receptor and HER2 accelerates tumorigenesis solely derived from the EGF receptor [*Cell* 1987 58, 287-292]. There is a report that the coexpression of EGF receptor and HER2 in breast cancer, oral cancer, lung cancer and the like causes poor prognosis [*Clin. Cancer Res.* 1999 5, 4164-4174]. Furthermore, there is a report that the coexpression of EGF receptor and HER2 in breast cancer relates to the resistance to endocrine therapy [*J. Steroid Biochem.* 1989 34, 123-131].

The present invention aims at finding a pharmaceutical agent that inhibits EGF receptor tyrosine kinase and a pharmaceutical agent that inhibits both the EGF receptor tyrosine kinase and HER2 tyrosine kinase. The dual inhibitor of EGF receptor and HER2 is advantageous in that it: can be applied to a wider range of diseases and is superior in that the synergistic dual inhibitory action affords a stronger treatment effect as compared to a pharmaceutical agent acting only on a single kinase.

The compound of the present invention shows a sustained enzyme inhibitory action and provides a more superior treatment effect than do conventionally reported reversible inhibitors.

DISCLOSURE OF THE INVENTION

The present inventors have conducted intensive studies with the aim of solving the above-mentioned problems and found that a quinazoline derivative having a particular structure has a strong tyrosine kinase inhibitory activity and cancer cell growth inhibitory action, and reached the present invention.

Accordingly, the present invention provides the following.

(1) A quinazoline derivative of the following formula (I)

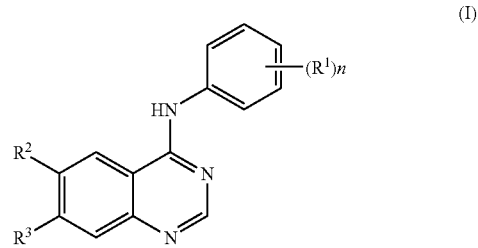

wherein n is an integer of 0-3, $R^1$ is a hydrogen atom, a halogen atom, a hydroxyl group, a cyano group, a nitro group, a $C_1$-$C_5$ alkyl group, a $C_1$-$C_5$ alkoxy group, —S(O)$_f$R$^{13}$ (wherein f is an integer of 0-2 and R$^{13}$ is a $C_1$-$C_5$ alkyl group), —NR$^{14}$R$^{15}$ (wherein R$^{14}$ and R$^{15}$ are each independently a hydrogen atom, a $C_1$-$C_5$ alkyl group, a $C_1$-$C_5$ alkanoyl group or a $C_1$-$C_5$ alkylsulfonyl group), a $C_2$-$C_5$ alkenyl group or a $C_2$-$C_5$ alkynyl group, one of R$^2$ and R$^3$ is R$^{27}$SO$_2$NH— wherein R$^{27}$ is a $C_1$-$C_5$ alkyl group optionally substituted by a morpholino group, (R$^{28}$SO$_2$)$_2$N— (wherein R$^{28}$ is a $C_1$-$C_5$ alkyl group optionally substituted by a morpholino group), a $C_1$-$C_5$ alkoxy group, MeCOCH$_2$CONH—, MeSCH$_2$CH$_2$CONH—, NCCH$_2$CONH—,

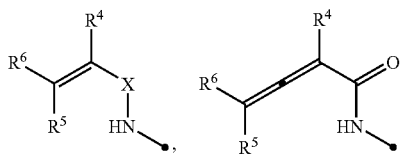

(wherein X is —C(O)— or SO$_2$— and R$^4$, R$^5$ and R$^6$ are each independently a hydrogen atom, a halogen atom or a $C_1$-$C_5$ alkyl group optionally substituted by a halogen atom, a morpholino group, a 4-$C_1$-$C_5$ alkylpiperazin-1-yl or di($C_1$-$C_5$ alkyl) amino group, or

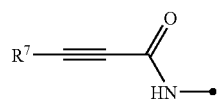

(wherein R$^7$ is a $C_1$-$C_5$ alkyl group optionally substituted by a halogen atom, a morpholino group, 4-$C_1$-$C_5$ alkylpiperazin-1-yl or di($C_1$-$C_5$ alkyl) amino group, and the other of R$^2$ and R$^3$ is

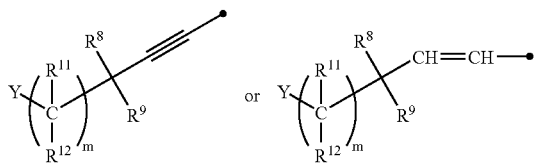

wherein a) R$^8$ and R$^9$ are each independently a hydrogen atom, b) R$^8$ and R$^9$ are each independently a $C_1$-$C_5$ alkyl group optionally substituted by a hydroxyl group or a $C_1$-$C_5$ alkoxy group, c) R$^8$ and R$^9$ are taken together to show C=O or d) R$^8$ and R$^9$ in combination form a ring to represent a $C_3$-$C_8$ cycloalkylene optionally via —O—, —S— or —NR$^{10}$ (wherein R$^{10}$ is a hydrogen atom or a $C_1$-$C_5$ alkyl group), m is an integer of 0-3, R$^{11}$ and R$^{12}$ are each independently a hydrogen atom or a $C_1$-$C_5$ alkyl group, and Y is a hydrogen atom, a hydroxyl group, a $C_1$-$C_5$ alkoxy group, a $C_1$-$C_5$ alkanoyloxy group, —N(R$^{16}$)—(CO)$_u$—(CR$^{17}$R$^{18}$)$_v$—

(CO)$_j$—R$^{19}$ (wherein R$^{16}$ is a) a hydrogen atom or b) a $C_1$-$C_5$ alkyl group optionally substituted by a cyano group or a $C_1$-$C_5$ alkoxy group, R$^{17}$ and R$^{18}$ are each independently a hydrogen atom or a $C_1$-$C_5$ alkyl group, u and j are each 0 or 1, v is an integer of 1-5 and R$^{19}$ is a hydrogen atom, a hydroxyl group, a cyano group, an amino group, a $C_1$-$C_5$ alkoxy group, a morpholino group, 4-$C_1$-$C_5$ alkylpiperazin-1-yl or di($C_1$-$C_5$ alkyl) amino group, provided that, when u and j are simultaneously 0, then v is an integer of 2-5),

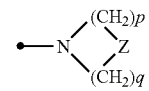

wherein p and q are each independently an integer of 2 or 3, Z is —O— or —S(O)$_g$— wherein g is an integer of 0-2, a carbonyl group or —NR$^{20}$— (wherein R$^{20}$ is a) a hydrogen atom, b) a $C_1$-$C_5$ alkylsulfonyl group, c) a $C_1$-$C_5$ alkanoyl group, d) a $C_1$-$C_5$ alkoxycarbonyl group or e) a $C_1$-$C_5$ alkyl group optionally substituted by a cyano group, a hydroxyl group or a $C_1$-$C_5$ alkoxy group) or

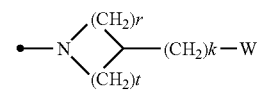

wherein r and t are each independently an integer of 1-3, k is 0 or 1, W is a hydrogen atom, a hydroxyl group, a $C_1$-$C_5$ alkoxy group, a $C_1$-$C_5$ alkanoyloxy group, a carboxyl group, a cyano group, a di($C_1$-$C_5$ alkyl)amino group, a morpholino group, pyrrolidin-1-yl, piperidin-1-yl, 4-$C_1$-$C_5$ alkylpiperazin-1-yl or CONR$^{21}$R$^{22}$ (wherein R$^{21}$ and R$^{22}$ are each independently a hydrogen atom or a $C_1$-$C_5$ alkyl group), or a pharmaceutically acceptable salt thereof, a hydrate thereof, a solvate thereof, an optically active compound thereof, a racemate thereof or a diastereomer mixture thereof.

(2) The quinazoline derivative of the aforementioned (1), which is represented by the following formula (I)

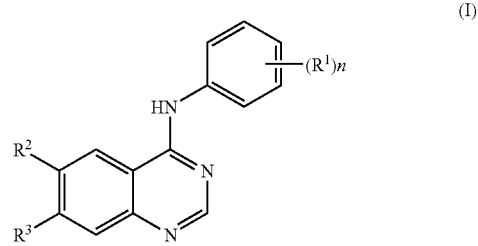

wherein
n is an integer of 1 or 2,
R$^1$ is a halogen atom, a cyano group, a C$_1$-C$_5$ alkyl group, a C$_1$-C$_5$ alkoxy group, —S(O)$_f$R$^{13}$ (wherein f is an integer of 0-2 and R$^{13}$ is a C$_1$-C$_5$ alkyl group), —NR$^{14}$R$^{15}$ (wherein R$^{14}$ and R$^{15}$ are each independently a hydrogen atom, a C$_1$-C$_5$ alkyl group, a C$_1$-C$_5$ alkanoyl group or a C$_1$-C$_5$ alkylsulfonyl group) or a C$_2$-C$_5$ alkynyl group,
one of R$^2$ and R$^3$ is R$^{27}$SO$_2$NH— (wherein R$^{27}$ is a C$_1$-C$_5$ alkyl group optionally substituted by a morpholino group), (R$^{28}$SO$_2$)$_2$N— (wherein R$^{28}$ is a C$_1$-C$_5$ alkyl group optionally substituted by a morpholino group), a C$_1$-C$_5$ alkoxy group, MeCOCH$_2$CO—, MeSCH$_2$CH$_2$CO—, NCCH$_2$CO—,

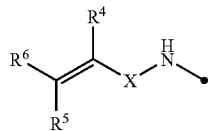

wherein X is —C(O)— or SO$_2$— and R$^4$, R$^5$ and R$^6$ are each independently a hydrogen atom, a halogen atom or a C$_1$-C$_5$ alkyl group optionally substituted by a halogen atom, a morpholino group, 4-C$_1$-C$_5$ alkylpiperazin-1-yl or di(C$_1$-C$_5$ alkyl)amino group, or

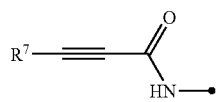

wherein R$^7$ is a C$_1$-C$_5$ alkyl group, and the other of R$^2$ and R$^3$ is

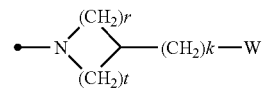

wherein a) R$^8$ and R$^9$ are each independently a hydrogen atom, b) R$^8$ and R$^9$ are each independently a C$_1$-C$_5$ alkyl group optionally substituted by a C$_1$-C$_5$ alkoxy group, m is an integer of 0-3, R$^{11}$ and R$^{12}$ are each independently a hydrogen atom or a C$_1$-C$_5$ alkyl group, and Y is a hydrogen atom, a hydroxyl group, a C$_1$-C$_5$ alkoxy group, a C$_1$-C$_5$ alkanoyloxy group, —N(R$^{16}$)—(CO)$_u$—(CR$^{17}$R$^{18}$)$_v$—(CO)$_j$—R$^{19}$ (wherein R$^{16}$ is a hydrogen atom, or a C$_1$-C$_5$ alkyl group optionally substituted by a cyano group or a C$_1$-C$_5$ alkoxy group, R$^{17}$ and R$^{18}$ are each independently a hydrogen atom or a C$_1$-C$_5$ alkyl group, u and j are each 0 or 1, v is an integer of 1-5 and R$^{19}$ is a hydrogen atom, a hydroxyl group, a cyano group, an amino group, a C$_1$-C$_5$ alkoxy group, a morpholino group, 4-C$_1$-C$_5$ alkylpiperazin-1-yl or di(C$_1$-C$_5$ alkyl)amino group, provided that, when u and j are simultaneously 0, then v is an integer of 2-5),

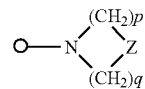

wherein p and q are each independently an integer of 2 or 3, Z is —O—, a carbonyl group or —NR$^{20}$— (wherein R$^{20}$ is a hydrogen atom, a C$_1$-C$_5$ alkylsulfonyl group, a C$_1$-C$_5$ alkanoyl group, a C$_1$-C$_5$ alkoxycarbonyl group or a C$_1$-C$_5$ alkyl group optionally substituted by a cyano group or a C$_1$-C$_5$ alkoxy group), or

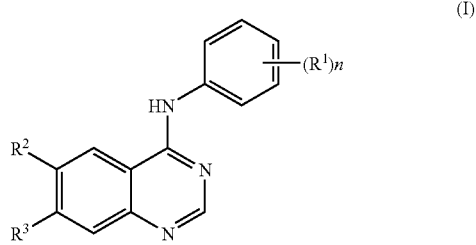

wherein r and t are each independently an integer of 1-3, k is 0 or 1, W is a hydrogen atom, a hydroxyl group, a C$_1$-C$_5$ alkoxy group, a C$_1$-C$_5$ alkanoyloxy group, a carboxyl group, a cyano group, a di(C$_1$-C$_5$ alkyl)amino group, a morpholino group or CONR$^{21}$R$^{22}$ (wherein R$^{21}$ and R$^{22}$ are each independently a hydrogen atom or a C$_1$-C$_5$ alkyl group), or a pharmaceutically acceptable salt thereof, a hydrate thereof, a solvate thereof, an optically active compound thereof, a racemate thereof or a diastereomer mixture thereof.

(3) The quinazoline derivative of the aforementioned (1) or (2), which is represented by the following formula (I)

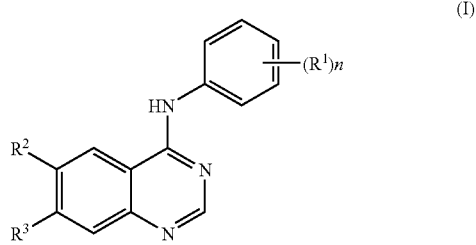

(I)

wherein
n is an integer of 0-3,
R$^1$ is a hydrogen atom, a halogen atom, a hydroxyl group, a cyano group, a nitro group, a C$_1$-C$_5$ alkyl group, a C$_1$-C$_5$ alkoxy group, —S(O)$_f$R$^{13}$ (wherein f is an integer of 0-2 and R$^{13}$ is a C$_1$-C$_5$ alkyl group), —NR$^{14}$R$^{15}$ (wherein R$^{14}$ and R$^{15}$ are each independently a hydrogen atom, a C$_1$-C$_5$ alkyl group, a C$_1$-C$_5$ alkanoyl group or a C$_1$-C$_5$ alkylsulfonyl group), a C$_2$-C$_5$ alkenyl group or a C$_2$-C$_5$ alkynyl group, $R^2$ is

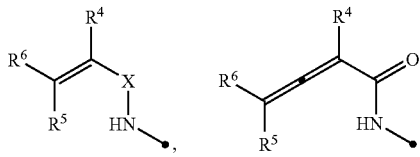

wherein X is —C(O)— or SO$_2$— and R$^4$, R$^5$ and R$^6$ are each independently a hydrogen atom, a halogen atom or a C$_1$-C$_5$ alkyl group optionally substituted by a halogen atom, a morpholino group, 4-C$_1$-C$_5$ alkylpiperazin-1-yl or di(C$_1$-C$_5$ alkyl)amino group, or

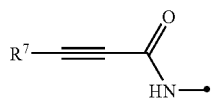

wherein R$^7$ is a C$_1$-C$_5$ alkyl group optionally substituted by a halogen atom, a morpholino group, 4-C$_1$-C$_5$ alkylpiperazin-1-yl or di(C$_1$-C$_5$ alkyl)amino group, and R$^3$ is

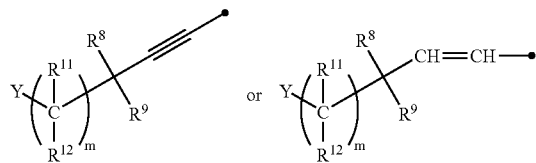

wherein R$^8$ and R$^9$ are each independently a hydrogen atom, a C$_1$-C$_5$ alkyl group optionally substituted by a hydroxyl group or a C$_1$-C$_5$ alkoxy group, R$^8$ and R$^9$ are taken together to denote C=O or R$^8$ and R$^9$ combination form a ring to represent C$_3$-C$_8$ cycloalkylene optionally via —O—, —S— or —NR$^{10}$ (wherein R$^{10}$ is a hydrogen atom or a C$_1$-C$_5$ alkyl group), m is an integer of 0-3, R$^{11}$ and R$^{12}$ are each independently a hydrogen atom or a C$_1$-C$_5$ alkyl group, and Y is a hydrogen atom, a hydroxyl group, a C$_1$-C$_5$ alkoxy group, a C$_1$-C$_5$ alkanoyloxy group, —N(R$^{16}$)—(CO)$_u$—(CR$^{17}$R$^{18}$)$_v$—(CO)$_j$—R$^{19}$ (wherein R$^{16}$ is a hydrogen atom, or a C$_1$-C$_5$ alkyl group optionally substituted by a cyano group or a C$_1$-C$_5$ alkoxy group, R$^{17}$ and R$^{18}$ are each independently a hydrogen atom or a C$_1$-C$_5$ alkyl group, u and j are each 0 or 1, v is an integer of 1-5 and R$^{19}$ is a hydrogen atom, a hydroxyl group, a cyano group, an amino group, a C$_1$-C$_5$ alkoxy group, a morpholino group, 4-C$_1$-C$_5$ alkylpiperazin-1-yl or a di(C$_1$-C$_5$ alkyl)amino group, provided that, when u and j are simultaneously 0, then v is an integer of 2-5, $$\cdot-N\begin{matrix}(CH_2)p\\ \\(CH_2)q\end{matrix}Z$$

wherein p and q are each independently an integer of 2 or 3, Z is —O— or —S(O)$_g$— (wherein g is an integer of 0-2), a carbonyl group or —NR$^{20}$— (wherein R$^{20}$ is a hydrogen atom, or a C$_1$-C$_5$ alkyl group optionally substituted by a cyano group or a C$_1$-C$_5$ alkoxy group) or $$\cdot-N\begin{matrix}(CH_2)r\\ \\(CH_2)t\end{matrix}(CH_2)k-W$$

wherein r and t are each independently an integer of 1-3, k is 0 or 1, W is a hydrogen-atom, a hydroxyl group, a C$_1$-C$_5$ alkoxy group, a C$_1$-C$_5$ alkanoyloxy group, a carboxyl group, a cyano group, a di(C$_1$-C$_5$ alkyl)amino group, a morpholino group, pyrrolidin-1-yl, piperidin-1-yl, 4-C$_1$-C$_5$ alkylpiperazin-1-yl or —CONR$^{21}$R$^{22}$ (wherein R$^{21}$ and R$^{22}$ are each independently a hydrogen atom or a C$_1$-C$_5$ alkyl group), or a pharmaceutically acceptable salt thereof, a hydrate thereof, a solvate thereof, an optically active compound thereof, a racemate thereof or a diastereomer mixture thereof.

(4) A compound of any of the aforementioned (1) to (3), which is represented by the following formula (1a)

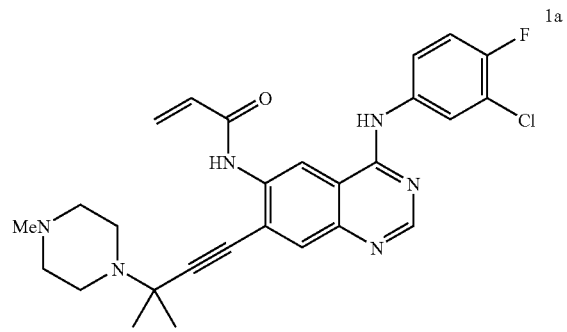

or a pharmaceutically acceptable salt thereof, a hydrate thereof, a solvate thereof, an optically active compound thereof, a racemate thereof or a diastereomer mixture thereof.

(5) The compound of the aforementioned (4), wherein the pharmaceutically acceptable salt is a salt with tosic acid.

(6) A crystal of a salt of a compound of the following formula (1a)

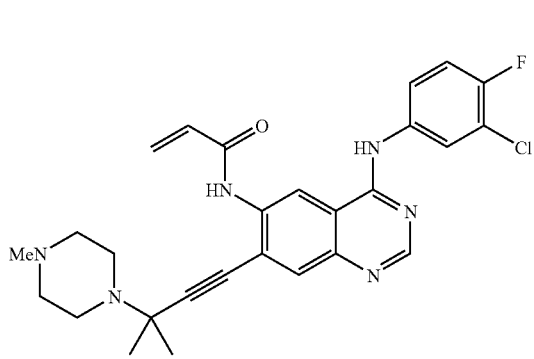

with tosic acid.

(7) The crystal of the aforementioned (6) having any one, two, three, four, five, six or all the characteristic absorbance peaks (2θ) shown below in powder X-ray diffraction pattern: characteristic peaks (2θ, ±0.2°) 3.3°, 6.6°, 7.5°, 9.4°, 13.9°, 17.4°, 19.1°.

(8) The compound of the aforementioned (4), wherein the hydrate is a ½ hydrate.

(9) A crystal of a ½ hydrate of a compound of the following formula (1a)

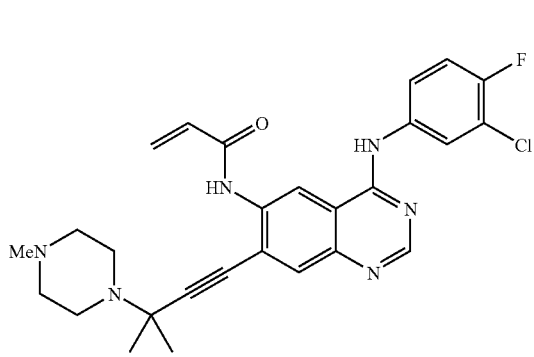

(10) The crystal of the aforementioned (9) having any one, two, three, four, five, six or all the characteristic absorbance peaks (2θ) shown below in powder X-ray diffraction pattern: characteristic peaks (2θ, ±0.2°) 7.1°, 10.6°, 11.9°, 12.2°, 13.8°, 17.3°, 18.4°.

(11) A pharmaceutical composition comprising a compound of any of the aforementioned (1) to (10) and a pharmaceutically acceptable carrier.

(12) A tyrosine-specific protein kinase inhibitor comprising a compound of any of the aforementioned (1) to (10) as an active ingredient.

(13) The inhibitor of the aforementioned (12), wherein the tyrosine-specific protein kinase is EGF receptor tyrosine-specific protein kinase.

(14) The inhibitor of the aforementioned (12) or (13), wherein the tyrosine-specific protein kinase is EGF receptor tyrosine-specific protein kinase and HER2 tyrosine-specific protein kinase.

(15) An agent for the treatment and/or prophylaxis of a disease caused by potentiation of tyrosine-specific protein kinase activity, which comprises a compound of any of the aforementioned (1) to (10) as an active ingredient.

(16) The agent for the treatment and/or prophylaxis of the aforementioned (15), which is an anticancer agent, or for the treatment and/or prophylaxis of psoriasis or a disease based on arteriosclerosis.

In the following, they are also simply referred to as a "tyrosine kinase inhibitor" in the present invention.

BRIEF DESCRIPTION OF THE DRAWINGS

FIG. 2 shows an XRD pattern of compound 1a.2TsOH type A crystal form.

DETAILED DESCRIPTION OF THE INVENTION

Figure 1:
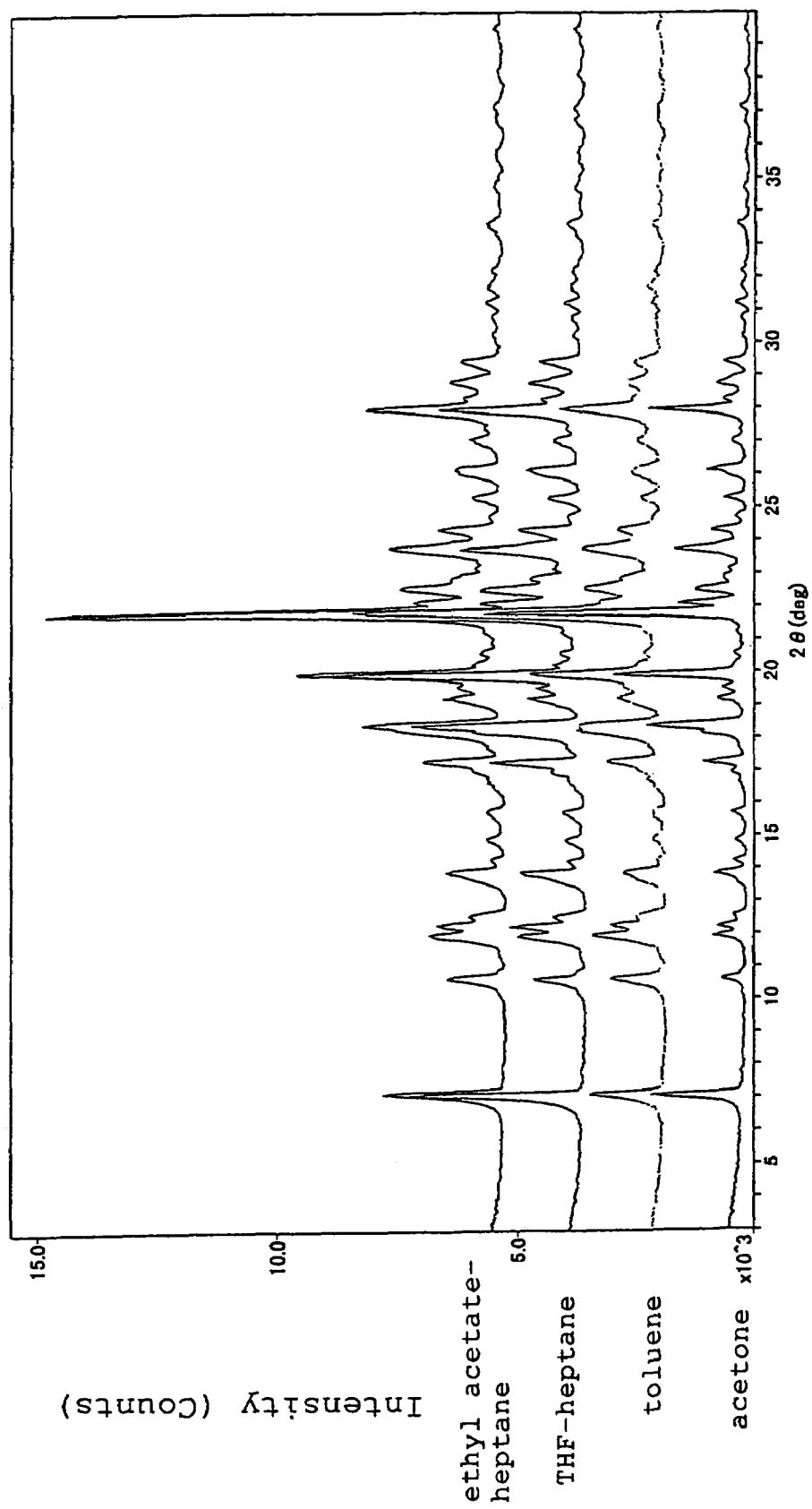
FIG. 1 shows an XRD pattern of compound 1a.½ $H_2O$ type A crystal form.

The present invention is explained in detail in the following.

The compound of the present invention is a quinazoline derivative of the aforementioned formula (I).

As the halogen atom defined for each substituent of the aforementioned formula (I), fluorine atom, chlorine atom, bromine atom and iodine atom can be mentioned; as the $C_1$-$C_5$ alkyl group, methyl group, ethyl group, n-propyl group, iso-propyl group, n-butyl group, iso-butyl group, sec-butyl group, tert-butyl group, n-pentyl group, neopentyl group and the like can be mentioned; as the $C_1$-$C_5$ alkoxy group, methoxy group, ethoxy group, n-propoxy group, iso-propoxy group, n-butoxy group, iso-butoxy group, sec-butoxy group, tert-butoxy group, n-pentyloxy group, neopentyloxy group and the like can be mentioned; as the $C_2$-$C_5$ alkenyl group, vinyl group, 1-propenyl group, 2-propenyl group, 1-butenyl group, 2-methylpropen-1-yl group, 2-butenyl group, 1-pentenyl group, 2-pentenyl group and the like can be mentioned; as the $C_2$-$C_5$ alkynyl group, ethynyl group, 1-propynyl group, 1-butynyl group, 1-pentynyl group and the like can be mentioned; and as the $C_1$-$C_5$ alkanoyl group, formyl group, acetyl group, propionyl group, butyryl group, isovaleryl group, valeryl group and the like can be mentioned.

The quinazoline derivative of the present invention is converted to a salt with the corresponding acid or base by a known method.

Examples of the salt include inorganic acid salts such as hydrochloride, sulfate, carbonate, phosphate and the like, and organic acid salts such as formate, acetate, propionate, lactate, oxalate, fumarate, maleate, citrate, tartrate, benzoate, phthalate, methanesulfonate, p-toluenesulfonate, isethionate, glucuronate, gluconate and the like. In addition, alkali metal salts such as sodium salt, potassium salt and the like, alkaline earth metal salts such as magnesium salt, calcium salt and the like, ammonium salt, a salt with a pharmacologically acceptable organic amine (tetramethylamine, triethylamine, benzylamine, phenethylamine, monoethanolamine, diethanolamine, tris(hydroxyethylamine), lysine and arginine etc.) can be mentioned.

The quinazoline derivative of the present invention can have various steric structures. For example, when considered from an asymmetric carbon atom as a center, the absolute configuration thereof may be (S)-form or (R)-form, or a racemate. Pure forms of optical isomer and diastereoisomer, optional mixtures of the isomers, racemate and the like are all encompassed in the present invention.

The quinazoline derivative of the formula (I) can be present in the form of, for example, a solvate such as hydrate or a non-solvate, and the present invention encompasses all such kinds of solvates having an anticancer activity.

Preferable embodiments of the compounds of the present invention are shown in the following Tables 1-9. In the Tables, Me means methyl group, Et means ethyl group and Pr means propyl group.

TABLE 1-continued
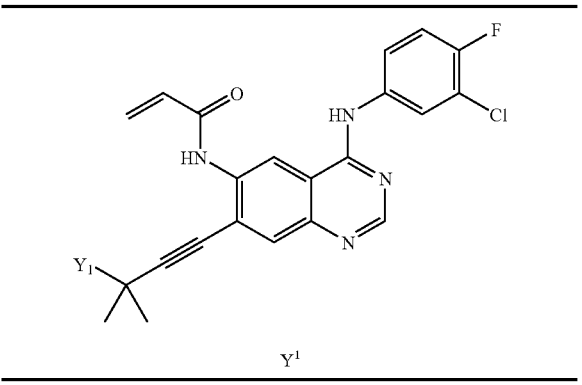
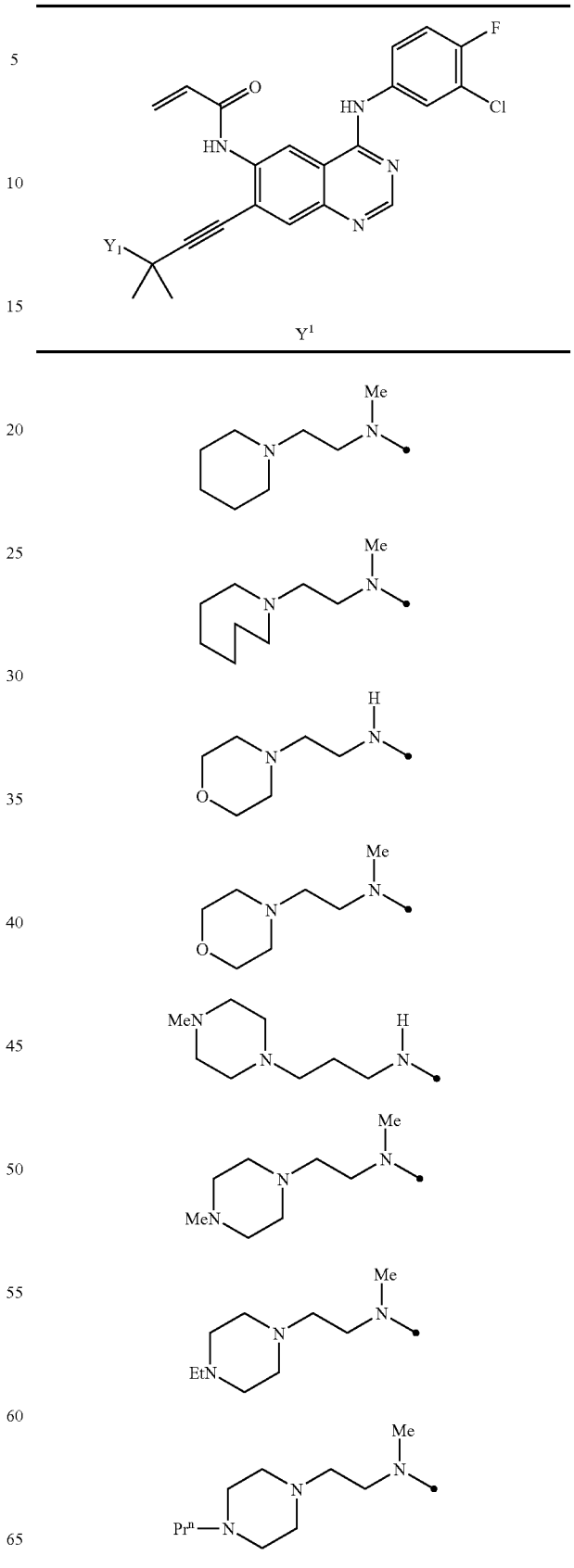

TABLE 1-continued
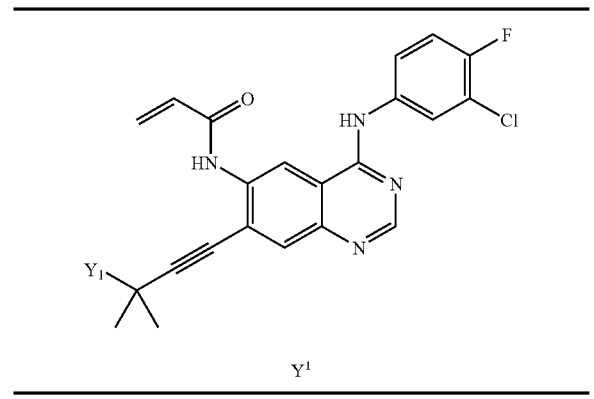
| Y¹ |
|---|
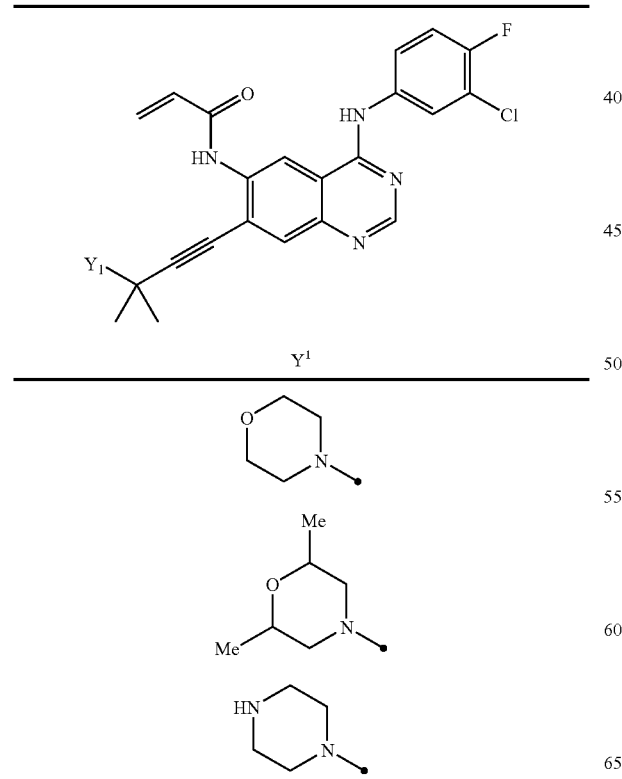
TABLE 2
TABLE 2-continued
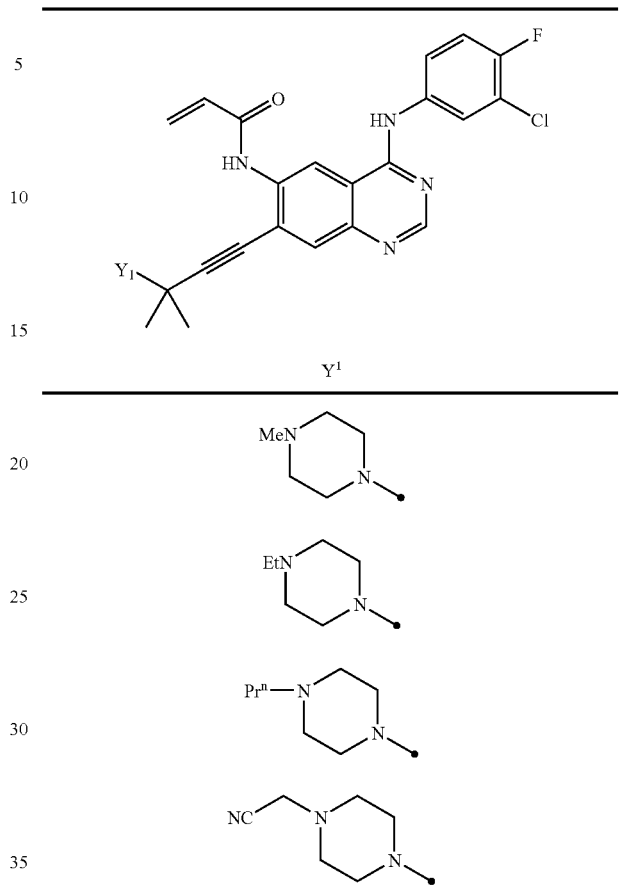

TABLE 2-continued
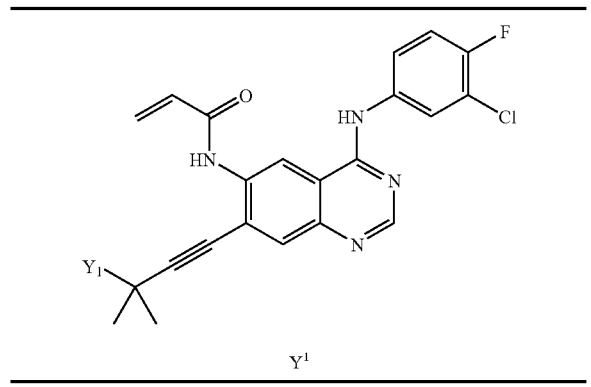
| $Y^1$ |
|---|
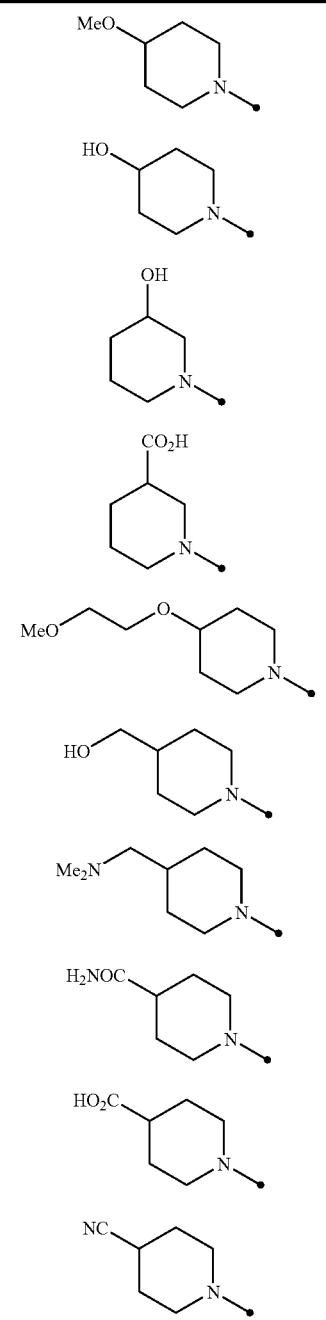
TABLE 2-continued
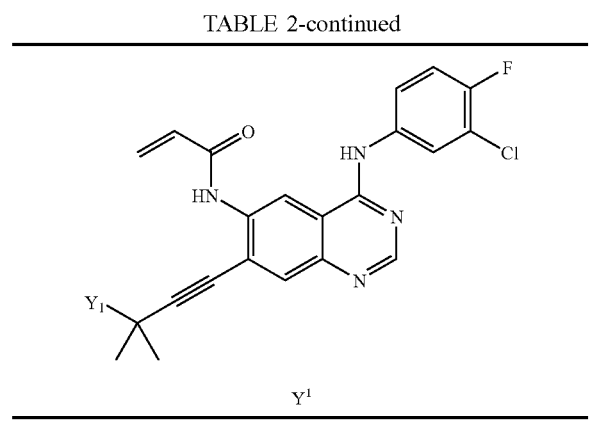
| $Y^1$ |
|---|
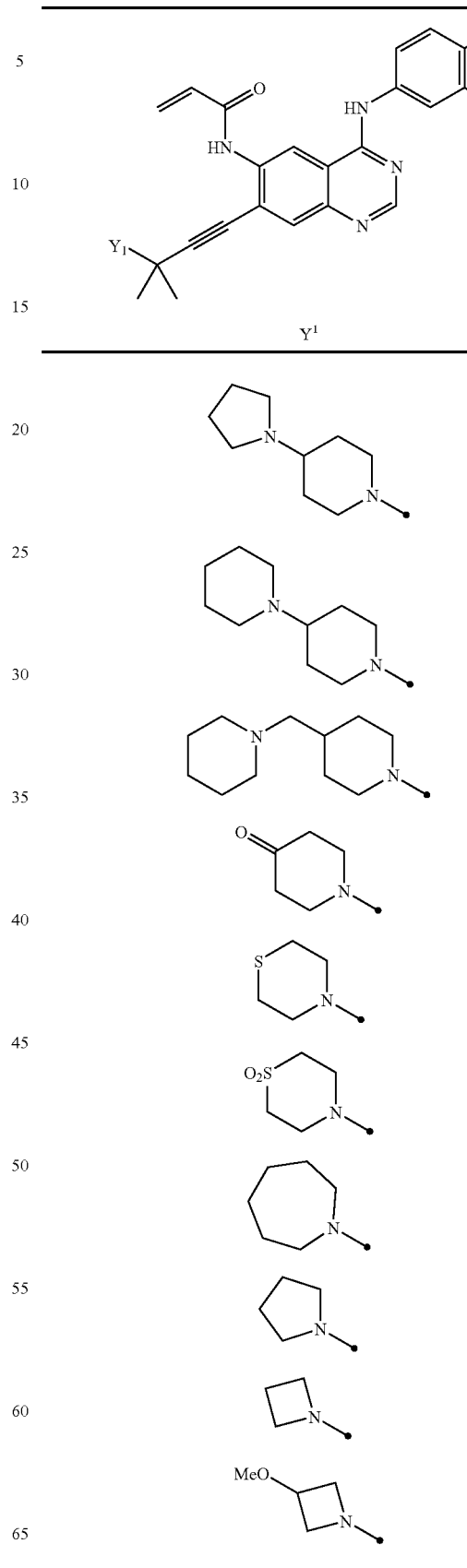

TABLE 2-continued
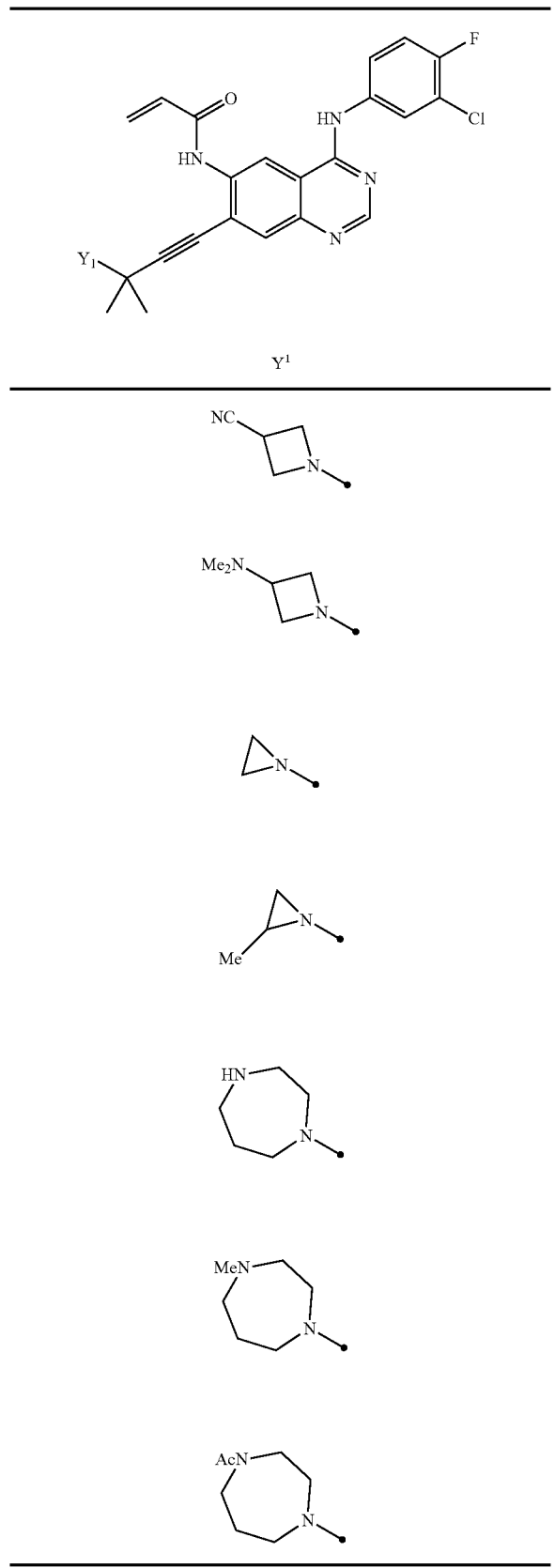
TABLE 3
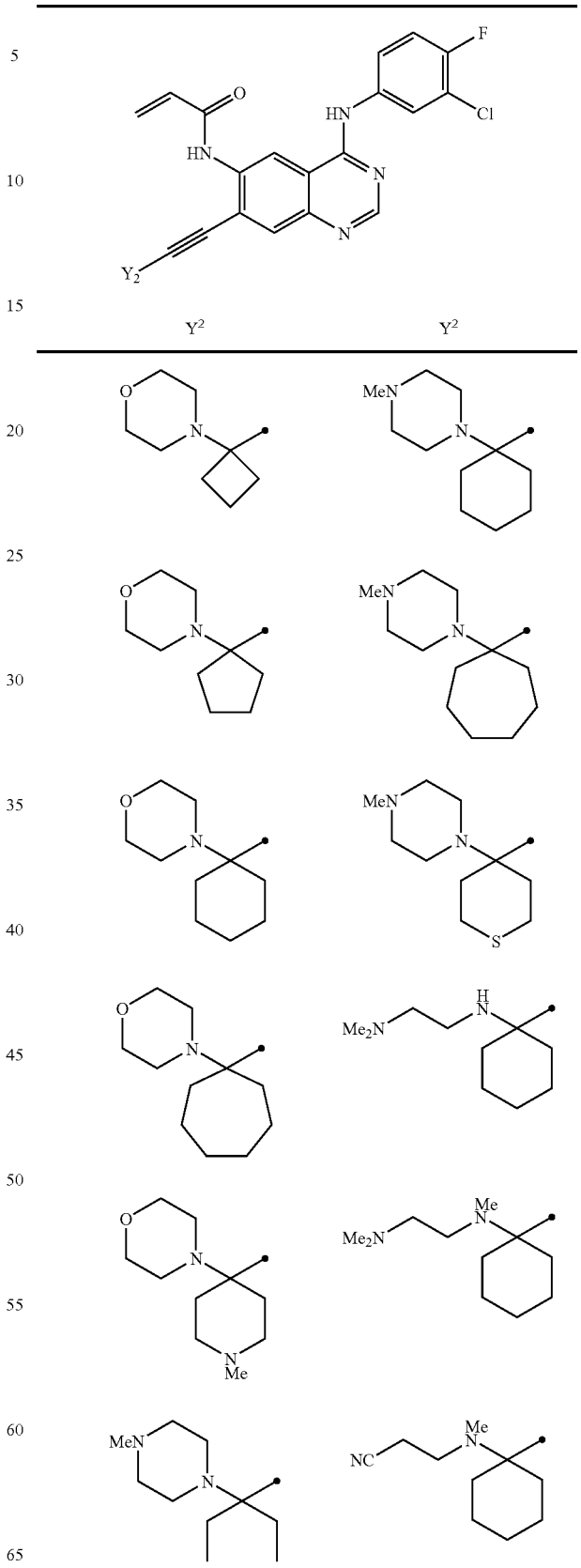

TABLE 3-continued
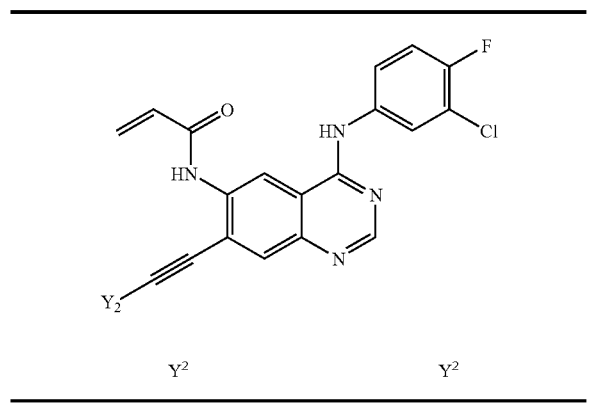
| $Y^2$ | $Y^2$ |
|---|---|
| 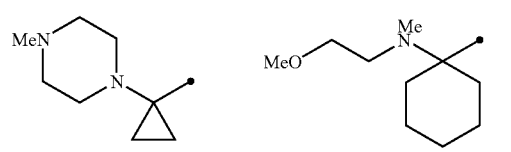 | 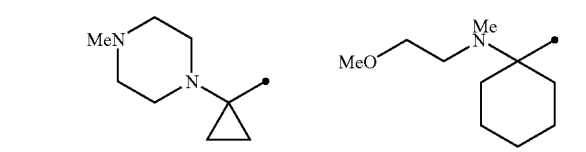 |
| 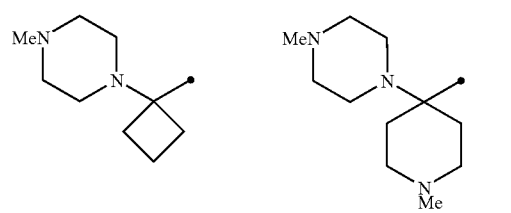 | |
| 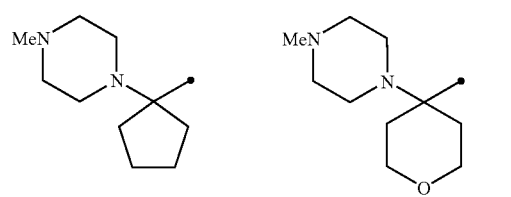 | |
| 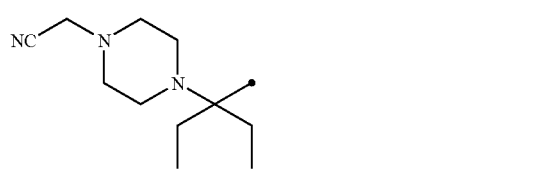 | |
| 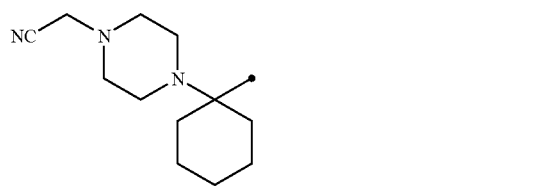 | |
TABLE 4
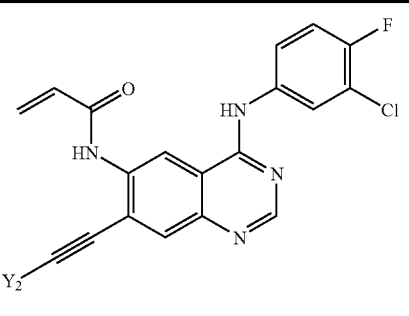
| $Y^2$ |
|---|
| 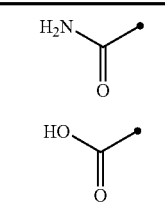 |
| 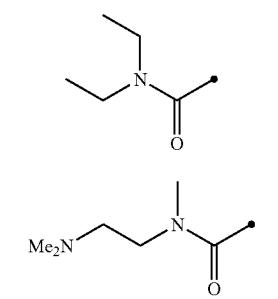 |
| 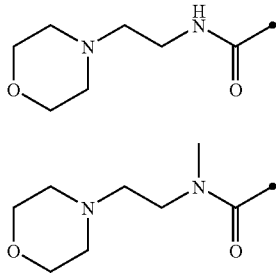 |
| 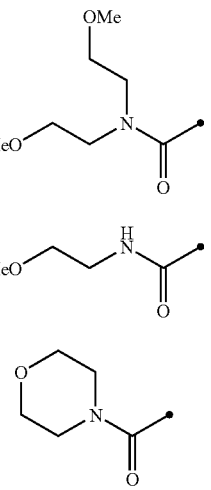 |

TABLE 4-continued
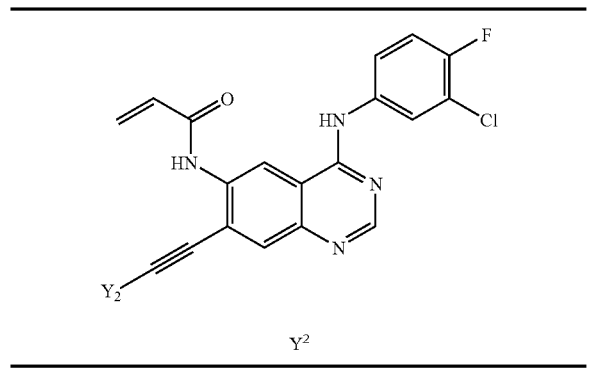
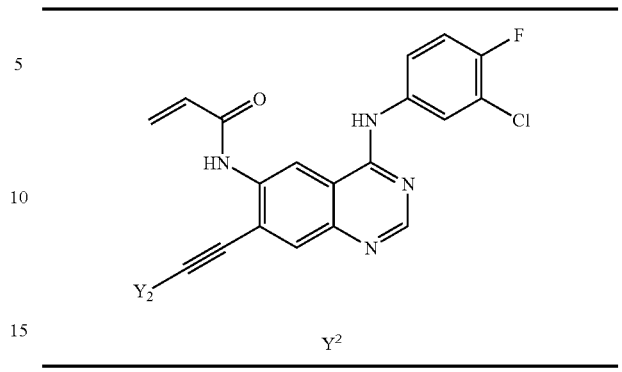
| $Y^2$ |
| --- |
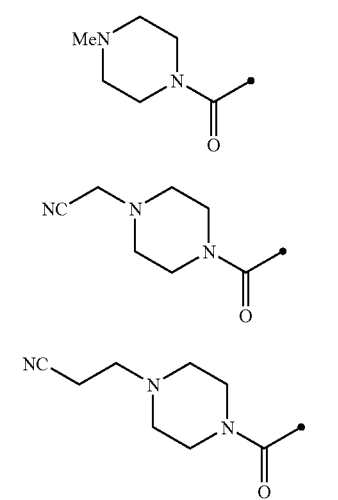
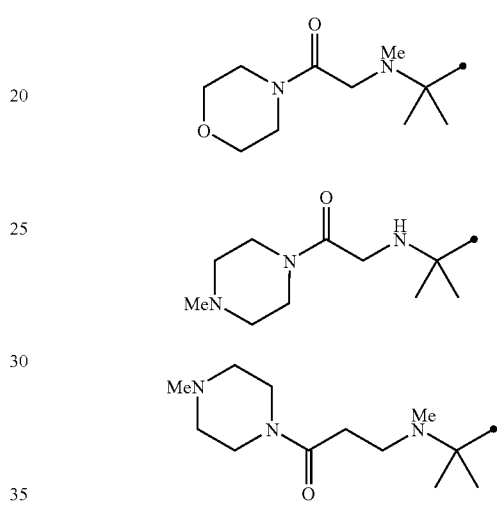
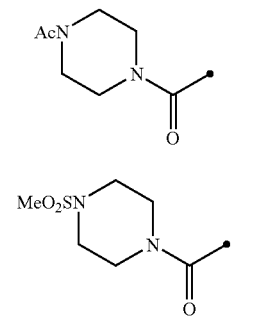
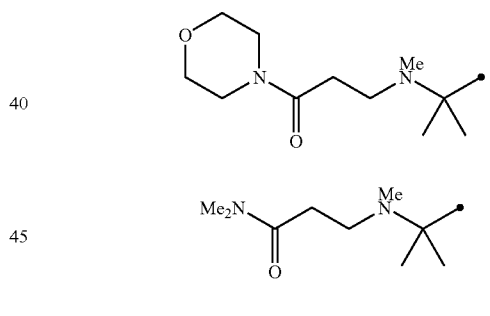
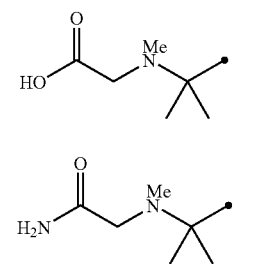
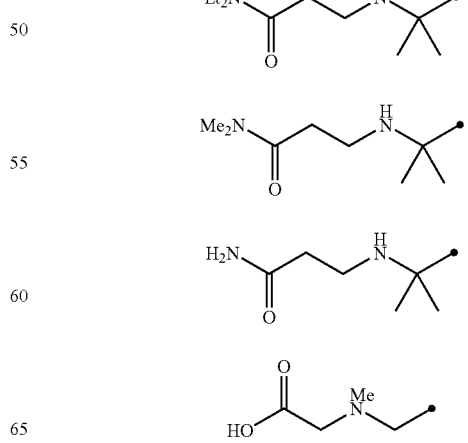

TABLE 4-continued
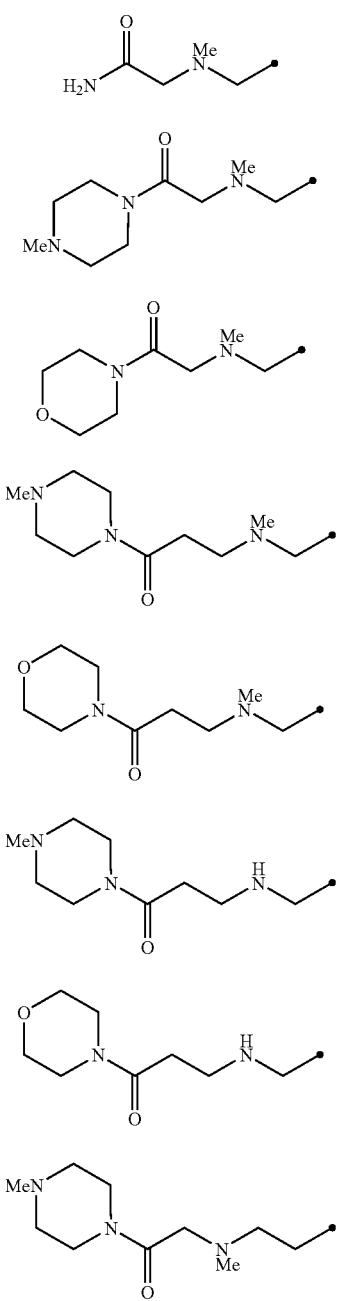
TABLE 4-continued
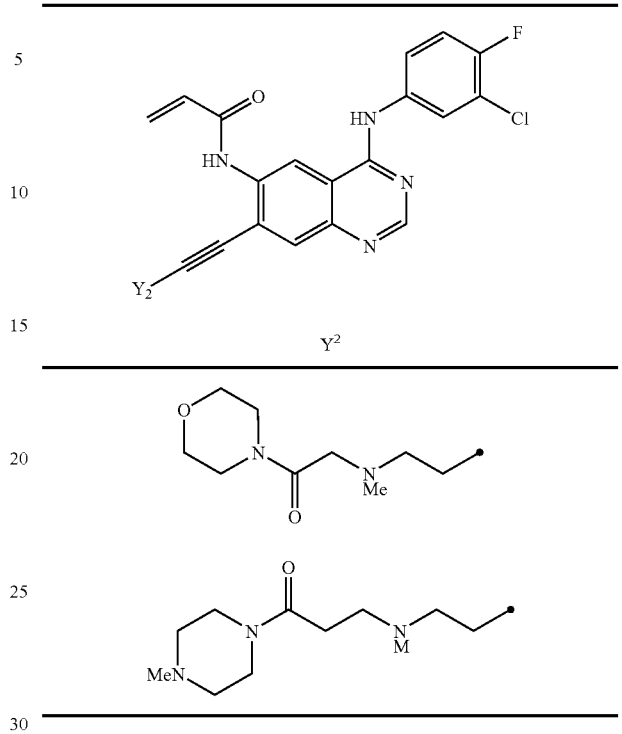
TABLE 5
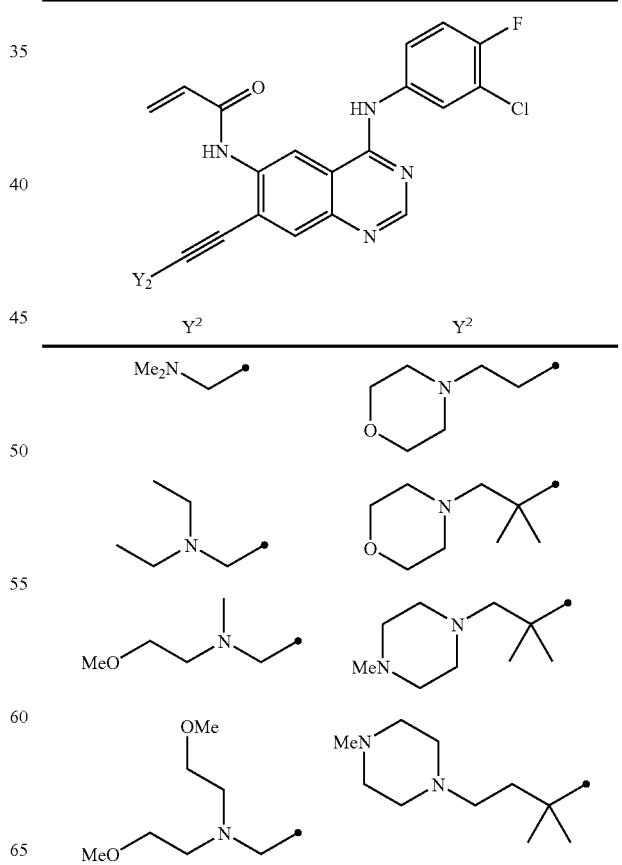

TABLE 5-continued
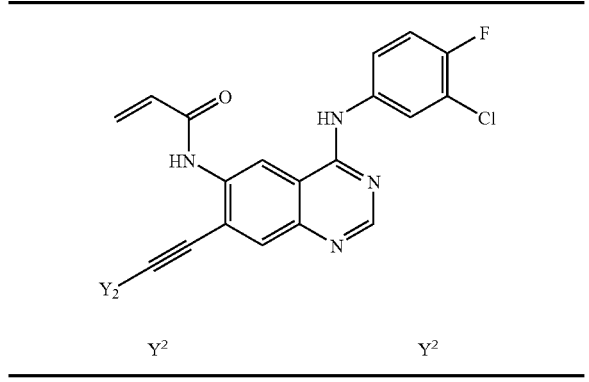
| $Y^2$ | $Y^2$ |
|---|---|
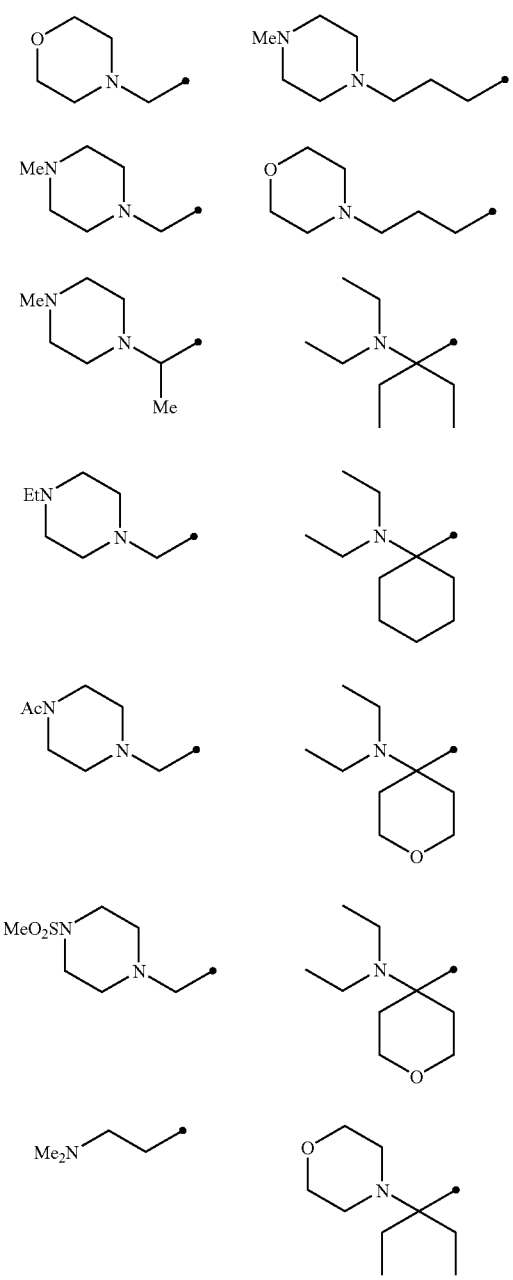
TABLE 5-continued
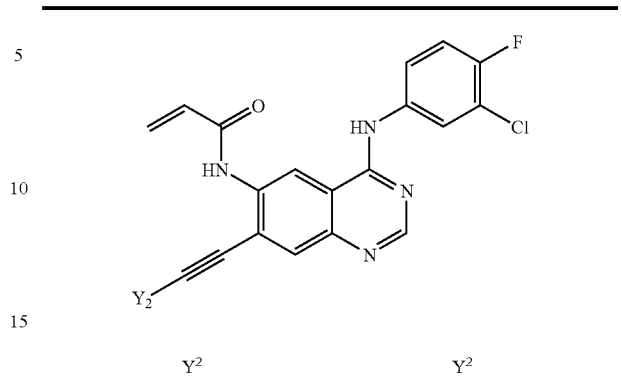
| $Y^2$ | $Y^2$ |
|---|---|
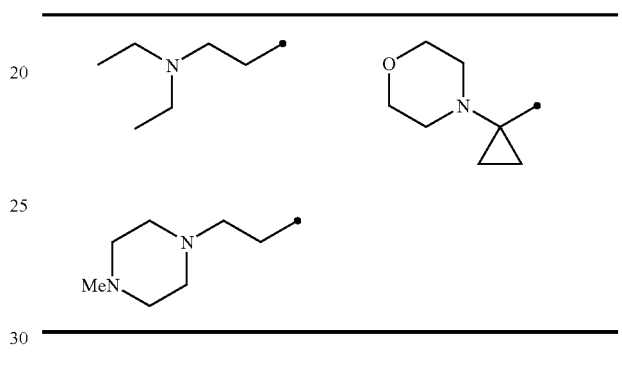
TABLE 6
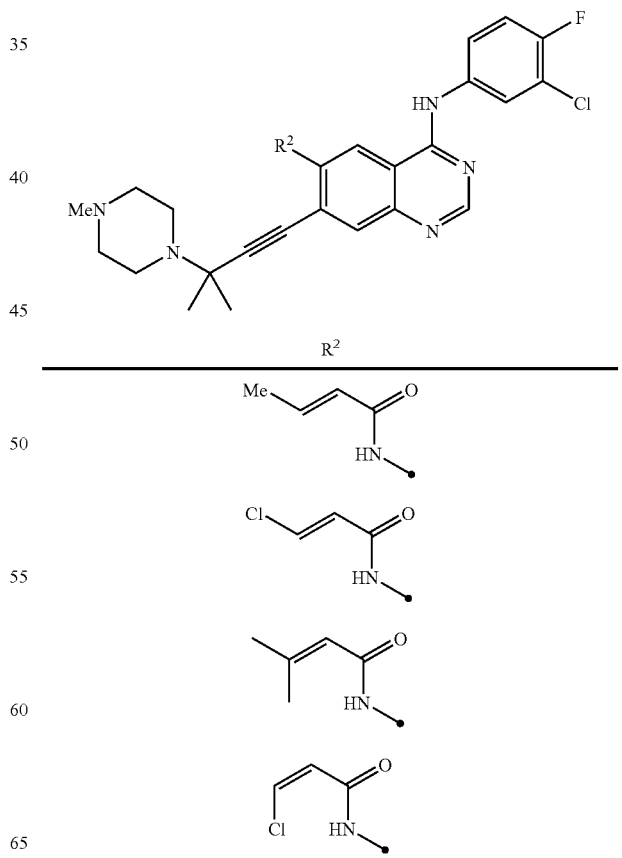

TABLE 6-continued
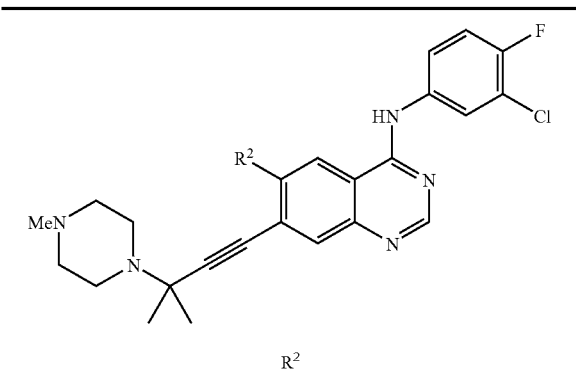
R²
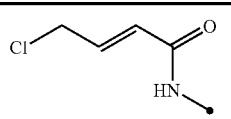
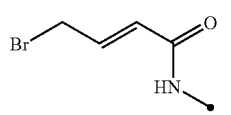
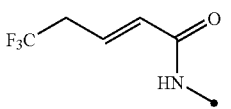
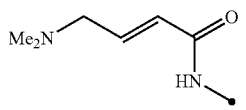
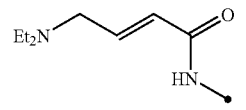
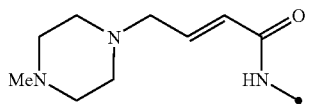
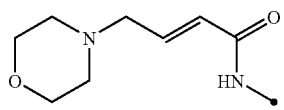
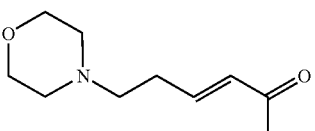
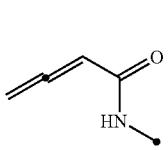
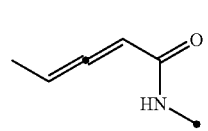
TABLE 6-continued
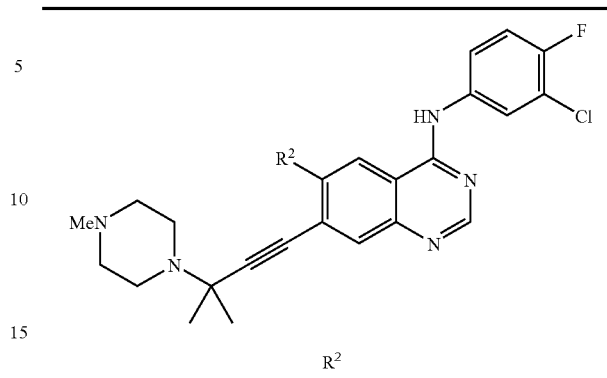
R²
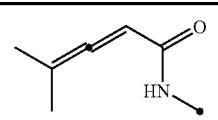
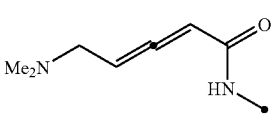
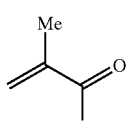
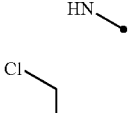
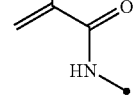
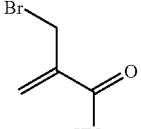
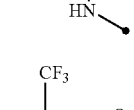
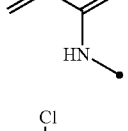
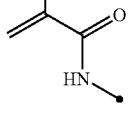
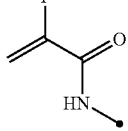

TABLE 6-continued
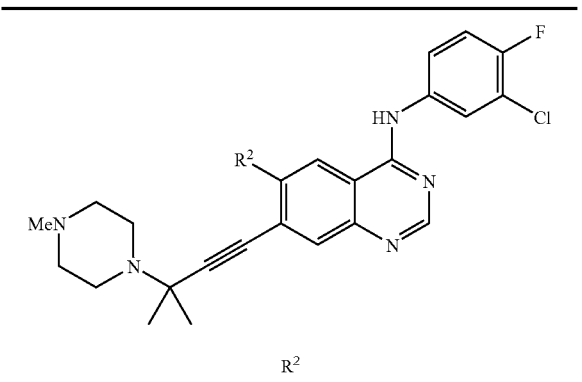
R[2]
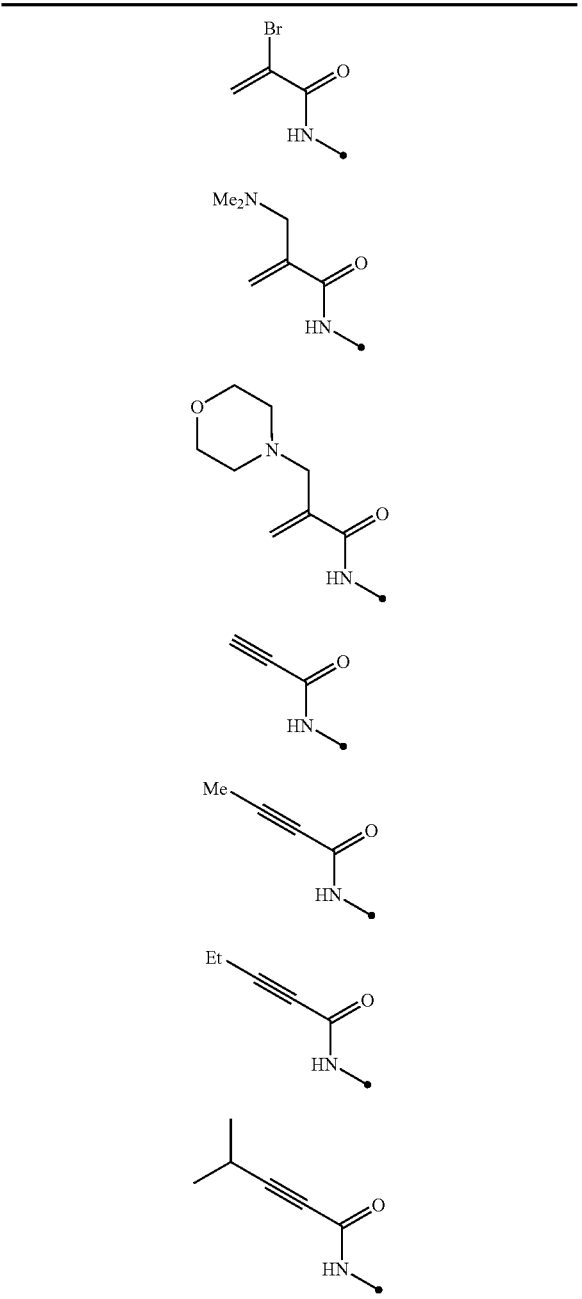
TABLE 6-continued
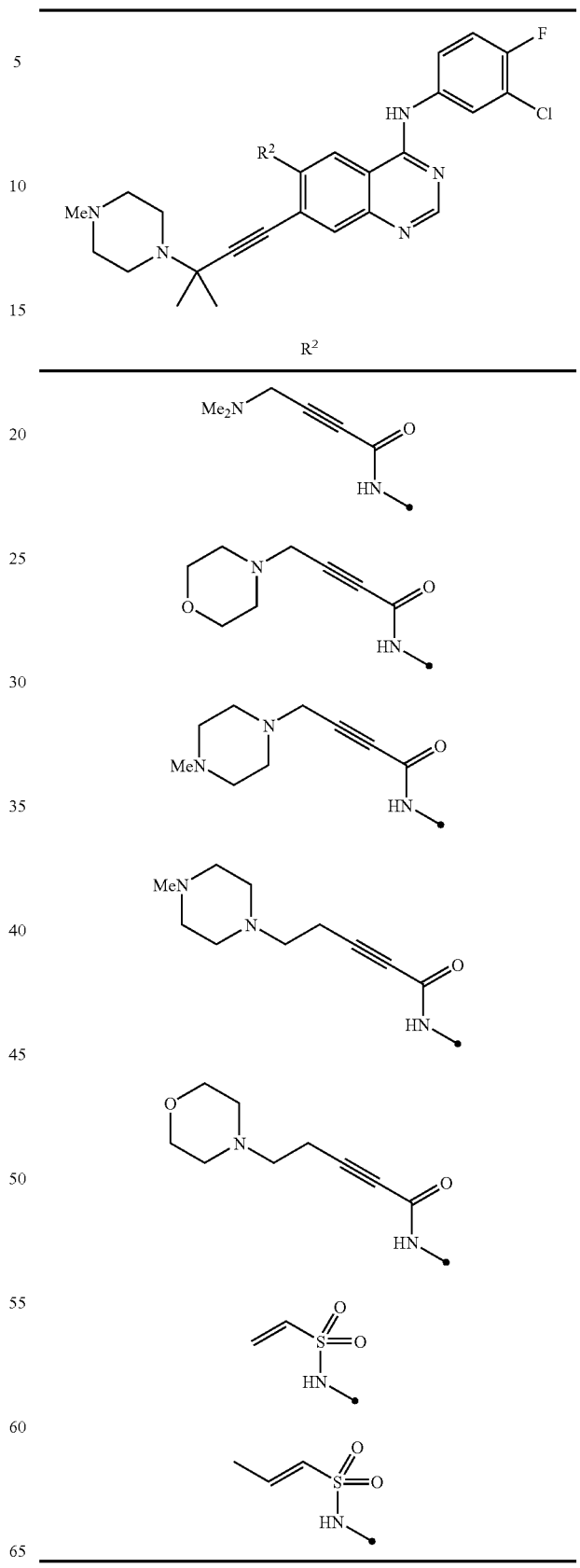

TABLE 7
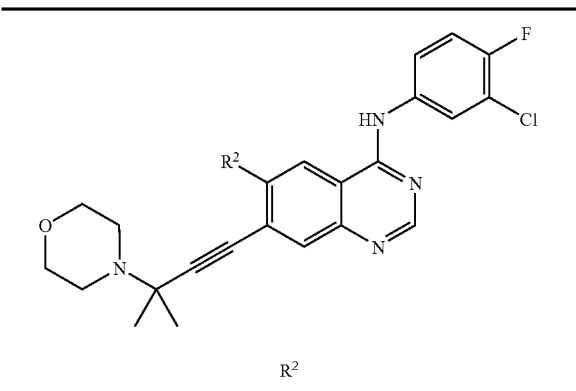
R²
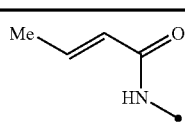
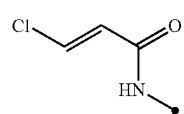
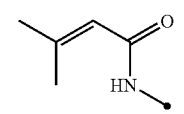
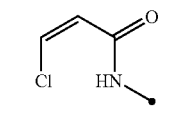
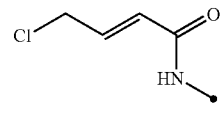
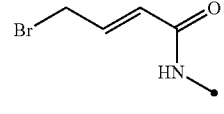
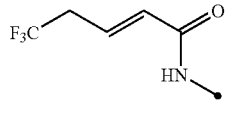
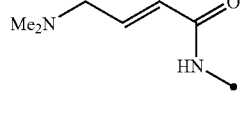
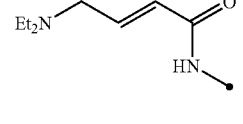
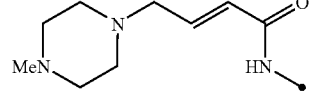
TABLE 7-continued
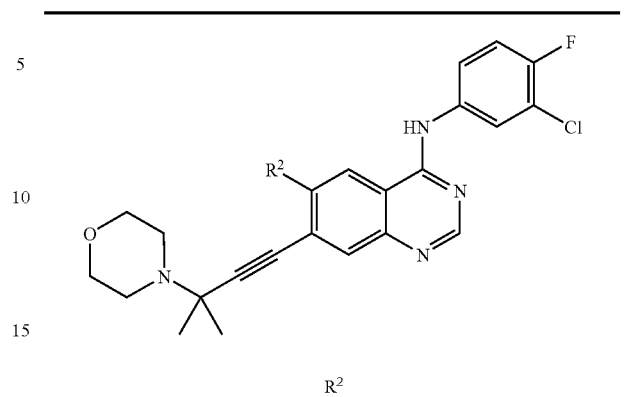
R²
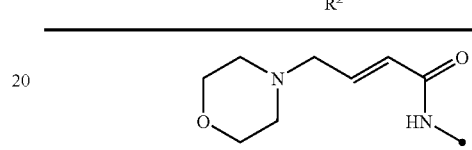
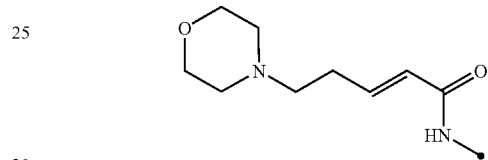
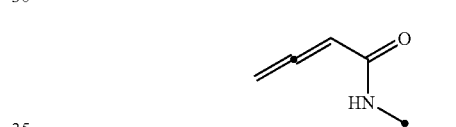
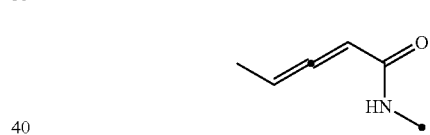
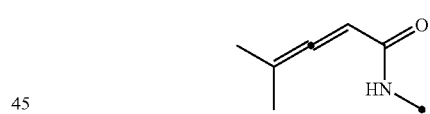
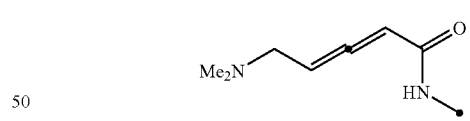

TABLE 7-continued
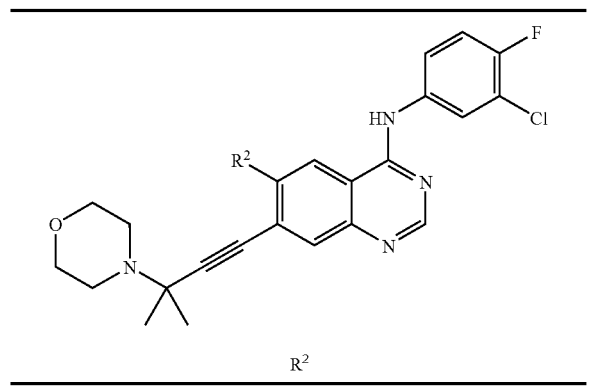
R²
TABLE 7-continued
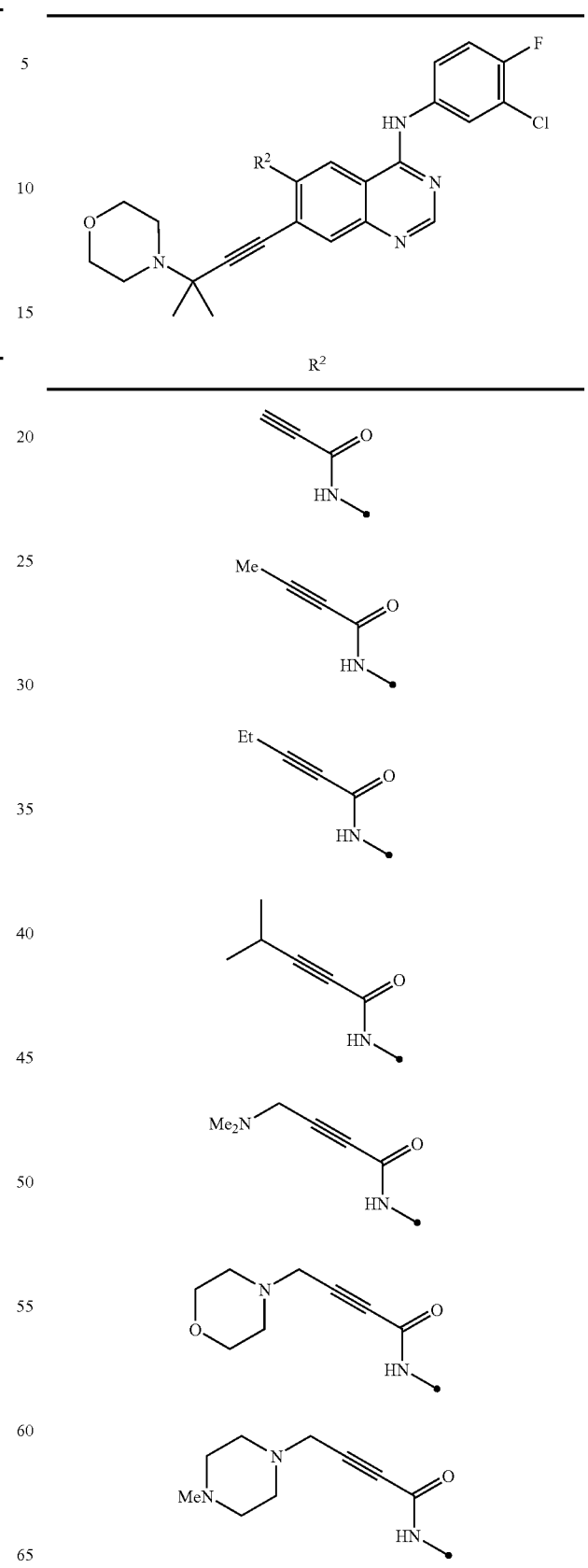

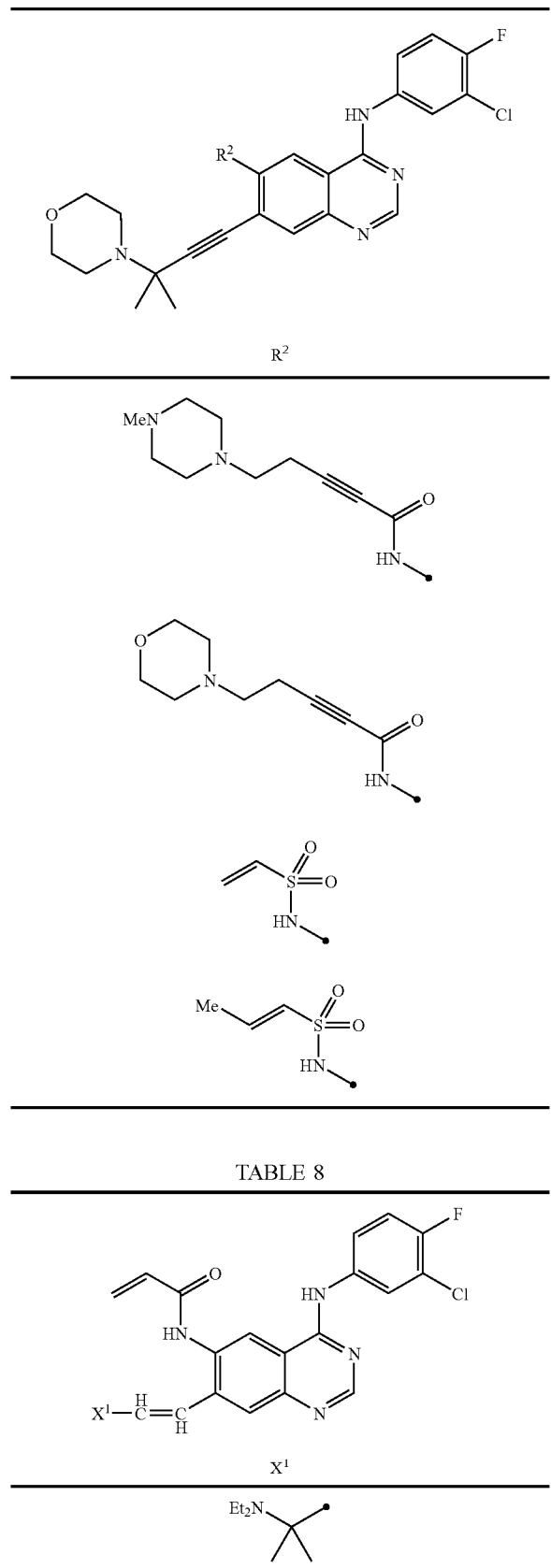

TABLE 8-continued

| X¹ |
|---|
| HO–piperidine–C(CH₃)₂– |
| MeO–piperidine–C(CH₃)₂– |
| MeN–homopiperazine–C(CH₃)₂– |
| pyrrolidine–C(CH₃)₂– |
| azetidine–C(CH₃)₂– |
| MeO₂C–CH₂CH₂–N(Et)–C(CH₃)₂– |
| MeN–piperazine–CH₂– |
| morpholine–CH₂– |
| NC–CH₂CH₂–N(Me)–CH₂– |

TABLE 8-continued

| X¹ |
|---|
| piperidine–CH₂CH₂–NH–CH₂– |
| Me₂N–CH₂CH₂–N(Me)–CH₂– |
| MeN–piperazine–CH₂CH₂– |
| morpholine–CH₂CH₂– |
| NC–CH₂CH₂–N(Me)–CH₂CH₂– |
| piperidine–CH₂CH₂–NH–CH₂CH₂– |
| Me₂N–CH₂CH₂–CH(Me)–N(Me)– |
| morpholine–C(cyclohexyl)– |
| MeN–piperazine–C(cyclohexyl)– |

TABLE 8-continued
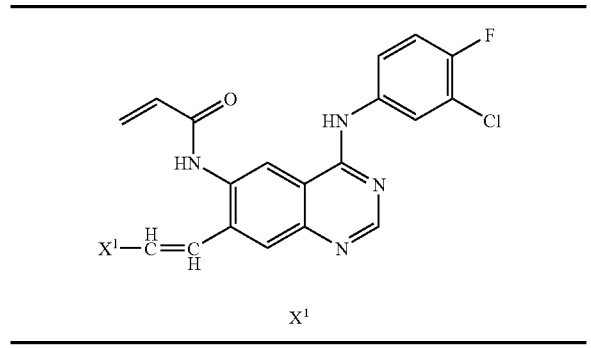
X¹
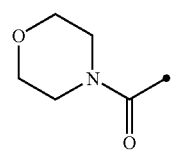
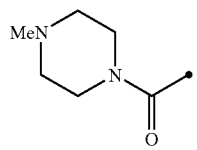
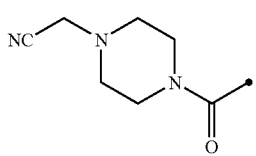
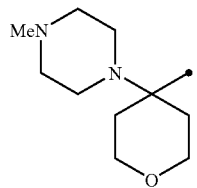
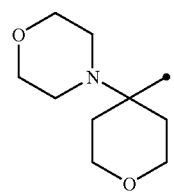
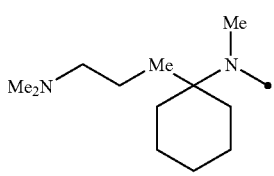
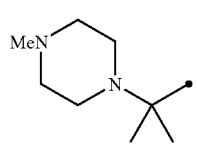
TABLE 8-continued
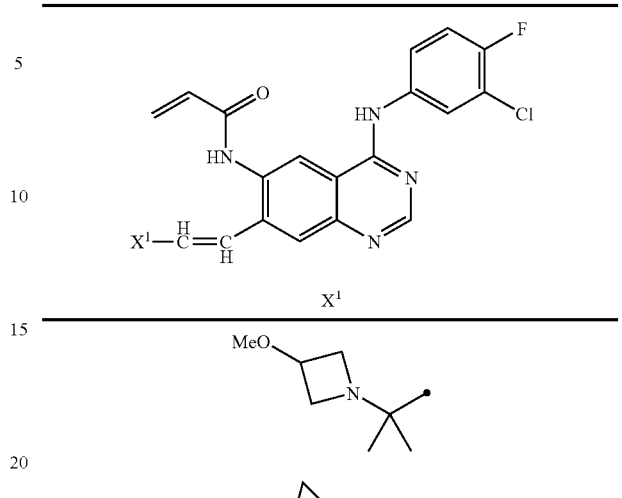
TABLE 9
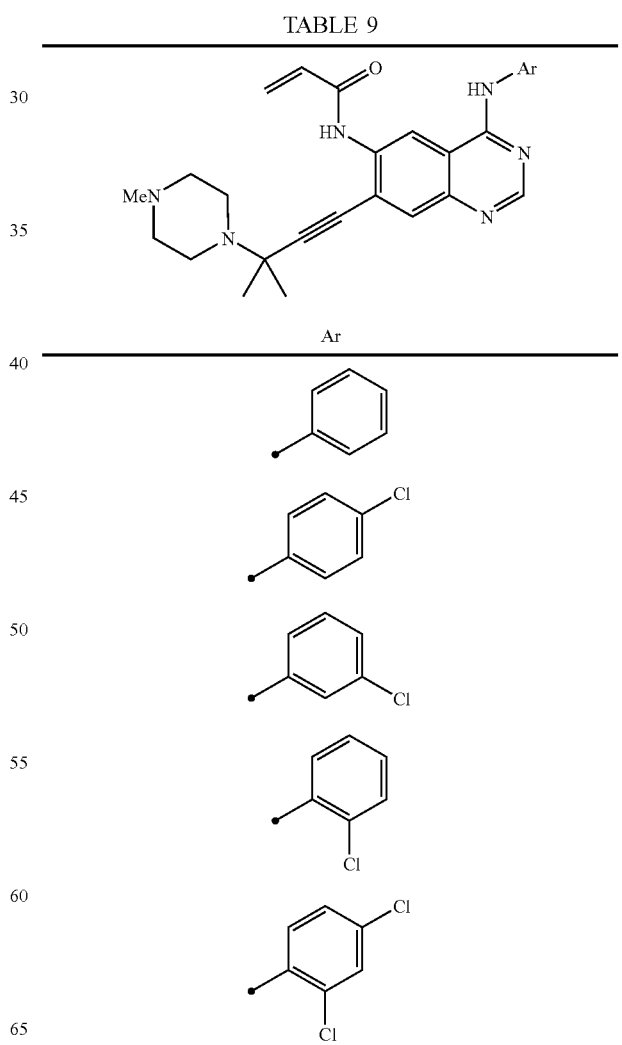

TABLE 9-continued
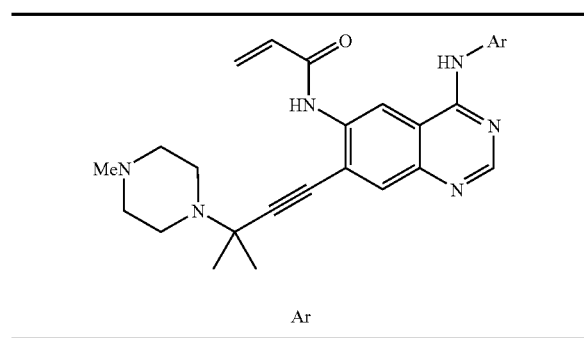
Ar
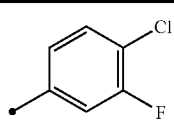
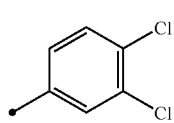
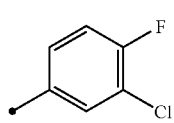
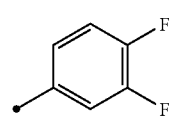
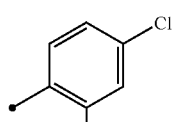
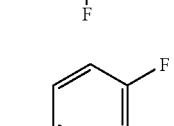
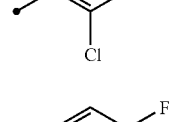
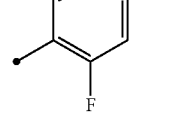
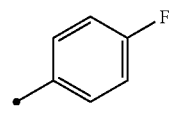
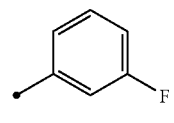
TABLE 9-continued
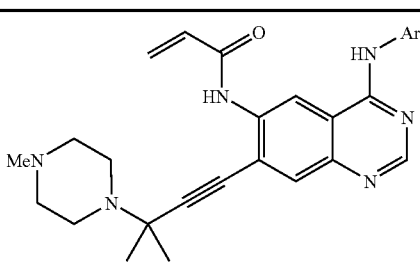
Ar
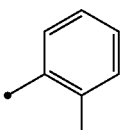
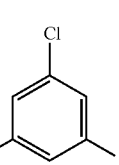
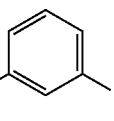
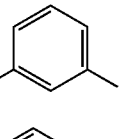
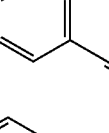
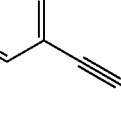
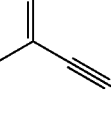
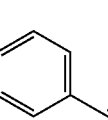
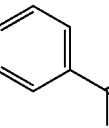

TABLE 9-continued

Of the compounds represented by the aforementioned formula (I), a compound wherein one of $R^2$ and $R^3$ has an amide bond can be produced by, for example, the following route (Scheme 1).

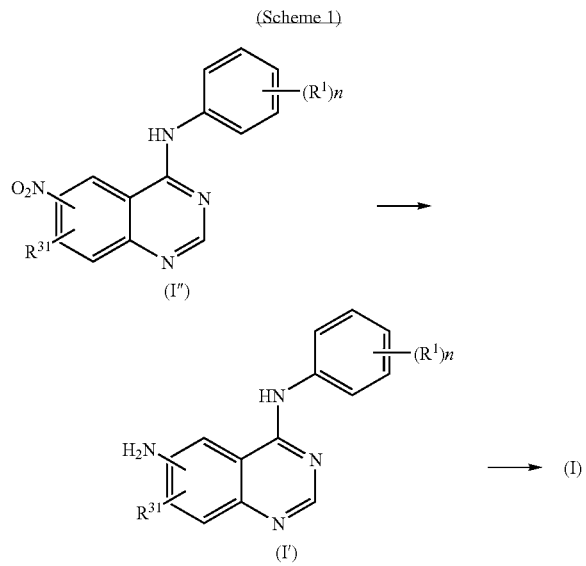

(Scheme 1)

wherein $R^{31}$ is

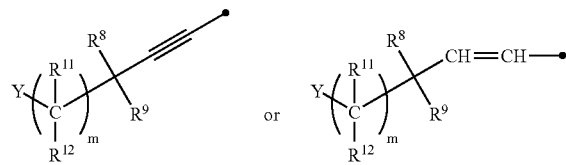

wherein each symbol is as mentioned above, $R^{31}$ is bonded to one of the 6-position and the 7-position of quinazoline ring, —NH$_2$ and —NO$_2$ are bonded to the other position, and other symbols are as defined above.

Compound (I) can be produced by a method wherein compound (I') is reacted with the corresponding sulfonic acid chloride, sulfonic acid anhydride, acid chloride or acid anhydride in, for example, an aprotic polar solvent such as tetrahydrofuran (hereinafter to be referred to as THF), an ether solvent such as diethyl ether and the like, a hydrocarbon solvent such as toluene, heptane and the like, dimethylformamide (hereinafter to be referred to as DMF), dimethyl sulfoxide (hereinafter to be referred to as DMSO), acetonitrile and the like, a protic polar solvent such as methanol, tert-butanol, water and the like or a mixed solvent thereof, in the presence or absence of a 0 to 10 equivalent amount of a nitrogen-containing base such as triethylamine, diethylamine, pyridine, 4-(N,N-dimethylamino)pyridine (hereinafter to be referred to as DMAP) and the like or an inorganic base such as sodium carbonate, potassium hydrogen carbonate and the like, at –20° C. to +200° C. for 5 min to 48 hrs. Alternatively, compound (I) can be produced by condensation reaction of the corresponding sulfonic acid or carboxylic acid in the co-presence of, for example, carbodiimides such as dicyclohexylcarbodiimide and the like, and an activation agent such as carbonyldiimidazole, diphenylphosphoryl azide and the like. In addition, a vinylsulfonamide compound can be produced by a treatment of 2-haloethylsulfonyl halide and compound (I') in the presence of an excess of a base such as triethylamine and the like, or with a base; and an acetylacetamide compound can be produced by reacting compound (I') with diketene in a solvent such as toluene, acetonitrile and the like.

While compound (I') can be produced by reacting the corresponding nitro compound (I'') with a 1 to 50 equivalent amount of reduced iron, zinc powder, tin chloride and the like in an ether solvent such as THF, diethyl ether and the like, a hydrocarbon solvent such as toluene, heptane and the like, an aprotic polar solvent such as DMF, acetonitrile and the like, a protic polar solvent such as methanol, ethanol, water and the like or a mixed solvent thereof, in the presence or absence of a 0.1 to 10 equivalent amount of a mineral acid such as hydrochloric acid, sulfuric acid and the like or an organic acid such as acetic acid and the like at a temperature of +20° C. to +200° C. for 5 min to 48 hrs, it may be produced by a method comprising reaction with hydrazine in the presence of a 0.1 to 10 equivalent amount of an iron salt such as FeCl$_3$ and the like for 5 min to 48 hrs, or by a reduction method using a metal complex compound such as LiAlH$_4$, NaBH$_4$, NaAlH$_2$(OCH$_2$CH$_2$OMe)$_2$ and the like or a metal hydride such as NaH and the like.

The compounds of the above-mentioned formulas (I'), (I'') and (I) can be also produced by the following methods.

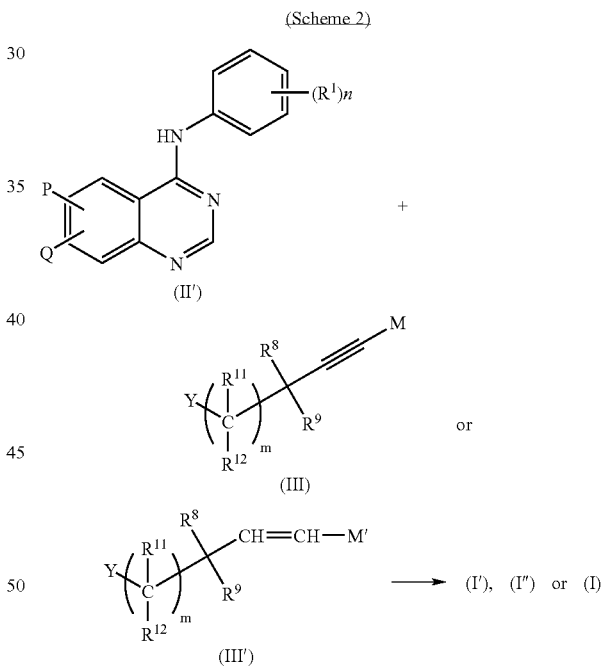

(Scheme 2)

wherein P' denotes amino group, nitro group, alkoxy group, or amide group such as sulfonamide, acrylamide and the like, Q denotes a leaving group such as halogen atom, trifluoromethanesulfonyl (OTf) and the like, P' and Q are bonded to the 6-position or 7-position of quinazoline ring; M denotes hydrogen atom, Li, MgBr, SnR$_3$ or B(OR)$_2$; M' denotes metal atom (group) such as Li, MgBr, SnR$_3$, AlR$_2$, B(OR)$_2$, ZrCp$_2$Cl wherein R is hydrogen atom or lower alkyl group and Cp is cyclopentadienyl group, and the like or halogen atom such as Br, I and the like; and other symbols are as defined above.

Compound (I'), (I") or (I) can be produced by reacting compound (II') with compound (III) or compound (III') in, for example, an ether solvent such as THF, diethyl ether and the like, a hydrocarbon solvent such as toluene and the like, an aprotic polar solvent such as DMF, dimethyl sulfoxide, acetonitrile and the like, a protic polar solvent such as methanol, tert-butanol, water and the like or a mixed solvent thereof, in the presence or absence of a 0 to 10 equivalent amount of a nitrogen-containing base such as triethylamine, diethylamine, pyridine and the like or an inorganic base such as sodium carbonate, potassium hydrogen carbonate, cesium fluoride and the like, a 0.001-0.5 equivalent amount of a palladium complex such as $Pd(PPh_3)_4$, $Pd(OAc)_2$, $PdCl_2(PPh_3)_2$ and the like, a 0.001-0.5 equivalent amount of a copper compound such as CuI and the like at +20° C. to +200° C. for 5 mm to 48 hrs. In this case, acetylide (III) [M=Li, MgX (X is halogen atom)] prepared by reacting compound (III) (M=H) with alkyllithium such as butyl-lithium and the like or a Grignard's reaction agent such as ethyl magnesium bromide and the like in an ether solvent such as THF, diethyl ether and the like, or a hydrocarbon solvent such as benzene, toluene and the like may be used. In addition, (III) [M=$SnR_3$, ZnCl, $B(OR')_2$] wherein R is lower alkyl group and R' is hydrogen atom or lower alkyl group, prepared by, for example, reaction with a trialkyltin chloride compound, zinc chloride and a trialkoxyboron compound may be used. In the case of (III') (M'=Br, I), a compound of the above-mentioned formula (I'), (I") or (I) can be produced by placing this (III') (M'=Br, I) and (II') in the co-presence of a 0.5-5 equivalent amount of hexameth-ylditin or bis(pinacolate)diboran in, for example, an ether solvent such as THF, diethyl ether and the like, a hydrocarbon solvent such as toluene and the like, an aprotic polar solvent such as DMF, DMSO, acetonitrile and the like, a protic polar solvent such as methanol, tert-butanol, water and the like or a mixed solvent thereof, in the presence of a 0 to 10 equivalent amount of a nitrogen-containing base such as triethylamine, diethylamine, pyridine and the like or an inorganic base such as sodium carbonate, potassium hydrogen carbonate, cesium fluoride and the like, and a 0.001-0.5 equivalent amount of a palladium complex such as $Pd(PPh_3)_4$, $Pd(OAc)_2$, $PdCl_2(PPh_3)_2$, Pd/C and the like. It can be also produced by lithiation of (III') (M'=Br, I) with n-butyllithium, tert-butyllithium and the like in, for example, an ether solvent such as THF, diethyl ether and the like or a hydrocarbon solvent such as toluene and the like to give (III') (M'=Li), which is then reacted with (II') along with a 0.001-0.5 equivalent amount of a palladium complex such as $Pd(PPh_3)_4$, $Pd(OAc)_2$, $PdCl_2(PPh_3)_2$ and the like.

For conversion of compound (II') ($P'=NO_2$) to compound (II') ($P'=NH_2$), the aforementioned reduction method of compound (I") to (I') can be used; and for conversion of (II') ($P'=NH_2$) to (II') (P' is amide group such as sulfonamide, acrylamide and the like), the aforementioned condensation reaction of compound (I') to (I) can be used.

Of the compounds represented by the above-mentioned formula (I), a compound wherein either $R^2$ or $R^3$ is alkoxy group can be produced by the reaction of compound (II') (P' is $C_1$-$C_5$ alkoxy group) with compound (III) or compound (III') (Scheme 2).

Of the compounds represented by the above-mentioned formula (I') and (I"), a compound wherein $R^3$ is represented by

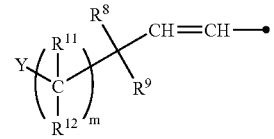

wherein Y, $R^8$, $R^9$, $R^{11}$, $R^{12}$ and m are as defined above, can be obtained by subjecting, from among the compounds of the above-mentioned formula (I') and (I"), a compound wherein $R^3$ is

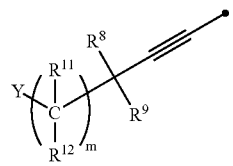

wherein Y, $R^8$, $R^9$, $R^{11}$, $R^{12}$ and m are as defined above, to reduction by catalytic hydrogenation using a 0.0001-0.5 equivalent amount of $Pd/BaSO_4$, $PtO_2$, Pd/C and the like as a catalyst in, for example, an ether solvent such as THF, diethyl ether and the like, a hydrocarbon solvent such as toluene and the like, halogenated hydrocarbon such as dichloromethane and the like, an aprotic polar solvent such as DMF, acetonitrile and the like, a protic polar solvent such as methanol, tert-butanol, water and the like or a mixed solvent thereof, or by, for example, hydrometallation reaction using a 0.1-5 equivalent amount of $LiAlH_4$, $(i-Bu)_2AlH$, diboran, followed by hydrolysis.

Now the production methods of compounds (III) and (III') are given below.

Compound (III') can be produced by, for example, hydrometallation reaction using, for example, $LiAlH_4$, $(i-Bu)_2AlH$, $R_3SnH$, $Cp_2Zr(H)Cl$, $Cp_2TiCl_2$—RMgX (Cp is cyclopentadienyl group, R is lower alkyl group and X is halogen atom) of the corresponding acetylene compound (III) (M=H) in an ether solvent such as THF, diethyl ether and the like, a hydrocarbon solvent such as toluene and the like, an aprotic polar solvent such as DMF, acetonitrile and the like or a mixed solvent thereof, or without a solvent, at a temperature of −30° C. to +150° C. By capturing compound (III') with, for example, a halogenating agent such as iodine, N-iodosuccinimide, N-bromosuccinimide and the like, the compound can be converted to compound (III') (M'=Br, I).

(Scheme 3)

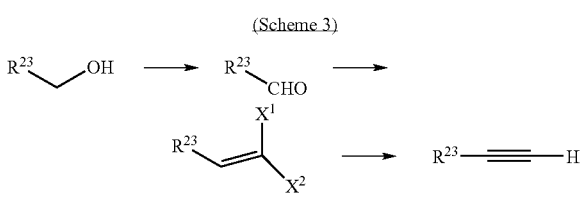

wherein $R^{23}$ denotes

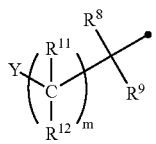

wherein each symbol is as mentioned above, and $X^1$ and $X^2$ are simultaneously, or one of $X^1$ and $X^2$ is, bromine atom or chlorine atom.

Compound (III) (M=H) can be produced by, for example, a method shown in Scheme 3. That is, haloalkene can be produced by a method comprising oxidization of the corresponding alcohol to give aldehyde and reaction thereof with, for example, a 0.1 to 10 equivalent amount each of carbon tetrachloride and triphenylphosphine in a suitable solvent such as dichloromethane, carbon tetrachloride and the like at −20 to +50° C. for 5 min to 48 hrs, or a method comprising reaction of, for example, $(EtO)_2P(O)CCl_3$ with an organic lithium compound such as n-butyllithium and the like in a solvent such as THF, diethyl ether and the like or a mixed solvent thereof at −100° C. to +100° C. for 5 min to 48 hrs, and the resulting haloalkene is treated with an organic lithium compound such as n-butyllithium and the like in, for example, a solvent such as THF, diethyl ether and the like or a mixed solvent thereof at −100° C. to +100° C. for 5 min to 48 hrs, and then hydrolyzed to give compound III. Where necessary, this conversion is carried out after protection of functional group in the compound.

(Scheme 4)

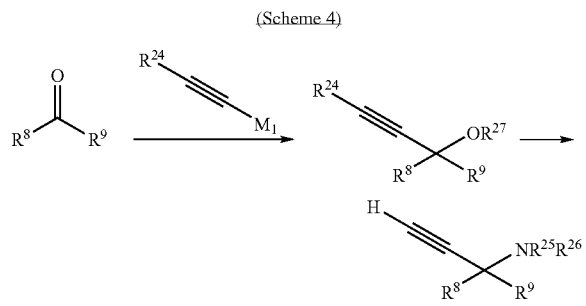

wherein $R^{24}$ denotes hydrogen atom or trialkylsilyl group, $M_1$ denotes a metal atom (group) such as Li, MgBr or $CeCl_3$ and the like, $R^{27}$ denotes hydrogen atom, $C_1$-$C_5$ alkyl group or $C_1$-$C_5$ alkanoyl group, $R^{25}$ and $R^{26}$ each denote $R^{16}$—$(CR^{17}R^{18})_v$—$(CO)_j$—$R^9$ wherein each symbol is as mentioned above, or $R^{25}$ and $R^{26}$ are taken together to form a ring,

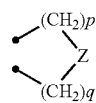

wherein each symbol is as mentioned above, or

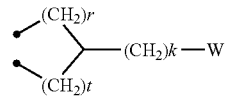

wherein each symbol is as mentioned above.

Particularly, for the production of compound (III) (m=0, M=H, Y are as defined above, except Y=H) (Scheme 4), an alcohol compound (III)(m=0, M=H, Y=OH) can be produced by reacting the corresponding ketone or aldehyde with ethynyl magnesium halide, lithium trimethylsilylacetylide or an ethynylation agent such as ethynylcelium compound and the like produced by reacting these with, for example, $CeCl_3$, in a suitable solvent such as THF, diethyl ether, toluene and the like at −100° C. to +100° C. for 5 min to 48 hrs. An acylated compound or an ether compound (III) (m=0, M=H, Y=$C_1$-$C_5$ alkoxy group, or $C_1$-$C_5$ alkanoyl group) can be produced by reacting the alcohol compound with an acid anhydride such as acetic anhydride and the like, an acylating agent such as acid chloride (e.g., acetic acid chloride and the like) and the like or an alkylation agent such as alkyl halide, alkylmethanesulfonate and the like in a suitable solvent such as dichloromethane, toluene, acetonitrile and the like in the presence of a base such as pyridine, triethylamine and the like or a base also as a solvent at 0° C. to 150° C. for 5 min to 48 hrs. Here, a method wherein ketone is reacted with an ethynylation agent and, without isolating the alcohol compound, alkoxide generated in situ is directly captured by an acylating agent or alkylating agent such as acid anhydride, acid chloride and the like, can be also used. In addition, the acylated compound can be produced by a method wherein the alcohol compound is reacted with an acid anhydride or an acid chloride in a suitable solvent such as acetonitrile, toluene, THF and the like in the presence of a 0.0001 to 0.5 equivalent amount of a suitable Lewis acid such as $Sc(OTf)_3$ and $BF_3.OEt_2$ at −30° C. to 120° C. When lithium trimethylacetylide is used, a treatment for removal of trimethylsilyl according to a conventional method may be performed before or after the acylation step or etheration step as necessary.

By reacting the acylated compound with the corresponding amine in, for example, a suitable solvent such as THF, dichloromethane, toluene, acetonitrile and the like, in the presence of a 0.001 equivalent amount to 0.5 equivalent amount of copper compound such as CuCl, CuI or copper powder and the like at 0° C. to +100° C. for 5 min to 48 hrs, (III) {m=0, M=H, Y=$NR^{25}R^{26}$ wherein $NR^{25}$, $R^{26}$ are as defined above} can be produced. By a method wherein (III) {m=0, M=H, Y=$NHR^{16}$ wherein $R^{16}$ are as defined above}, which can be produced by the above method, is reacted with the corresponding carboxylic acid chloride or acid anhydride in an ether solvent such as THF, diethyl ether and the like, a hydrocarbon solvent such as toluene, heptane and the like, an aprotic polar solvent such as DMF, dimethyl sulfoxide, acetonitrile and the like, a protic polar solvent such as methanol, tert-butanol, water and the like or a mixed solvent thereof, in the presence or absence of a 0 to 10 equivalent amount of a nitrogen-containing base such as triethylamine, diethylamine, pyridine, DMAP and the like or an inorganic base such as sodium carbonate, potassium-hydrogen carbonate and the like at −20° C. to +200° C. for 5 min to 48 hrs, or a method wherein (III) is subjected to a condensation reaction with the corresponding carboxylic acid in the co-presence of, for example, carbodiimides such as dicyclohexylcarbodiimide and the like, and a condensation agent such as carbonyldiimidazole, diphenylphosphorylazide and the like, (III) {m=0, M=H, Y=N($R^{16}$)—(CO) ($CR^{17}R^{18}$)$_v$—(CO)$_j$—$R^{19}$ wherein $R^{16}$ to $R^{19}$, j and v are as defined above} can be produced.

In the case of production of compound (III) (m=1 to 3, M=H, Y=—$NR^{25}R^{26}$; $R^{25}$, $R^{26}$ are as defined above, except Y=H), from among the corresponding compounds (III), a compound wherein Y is halogen atom such as chlorine, bromine, and the like, or a leaving group such as toluenesulfonate, methanesulfonate and the like is reacted with a 0.5-100 equivalent amount of the corresponding amine in a suitable solvent such as acetonitrile, THF, DMF and the like, in the presence or absence of a base such as potassium carbonate, diisopropylethylamine, sodium hydride and the like, at −20° C. to +150° C. for 5 min to 72 hrs to give (III) {m=1 to 3, M=H, Y=$NR^{25}R^{26}$ wherein $NR^{25}$, $R^{26}$ are as defined above}. By subjecting III) {m=1 to 3, M=H, Y=$NHR^{16}$ wherein $R^{16}$ is as defined above} produced by this method to a condensation reaction similar to that used for the above-mentioned (III) {m=0, M=H, Y=$NHR^{16}$ wherein $R^{16}$ are as defined above}, compound (III) {m=1 to 3, M=H, Y=N($R^{16}$)—(CO) ($CR^{17}R^{18}$)$_v$—(CO)$_j$—$R^{19}$ wherein $R^{16}$ to $R^{19}$, j and v are as defined above} can be produced.

The quinazoline derivative of the present invention can be used as an agent for treatment and/or prophylaxis of the diseases caused by potentiation of tyrosine kinase activity; that is, as an anticancer agent or an agent for the treatment and/or prophylaxis of psoriasis and the diseases (e.g., ischemic cardiac disease, acute coronary artery syndrome etc.) based on arteriosclerosis action.

When the compound of the present invention represented by the above-mentioned formula (I) is used for the above-mentioned objects, it is generally administered systemically or topically in an oral or parenteral form. The dose varies depending on the age, body weight, symptom, treatment effect, administration method, treatment period and the like. Generally, the compound is orally administered to an adult in an amount of 1 mg to 5 g per dose, once to several times a day, or parenterally administered to an adult in an amount of 1 mg to 5 g per dose, once to several times a day, or intravenously administered in a sustained manner for 1 hr to 24 hrs a day. Because the dose varies depending on diverse conditions as mentioned above, a dose less than the above-mentioned dose may be sufficient, or administration of a dose beyond the above dose range may be necessary.

When the compound of the present invention is administered, it is used as a solid composition, liquid composition or other composition for oral administration, an injection for parenteral administration, an external agent, an adhesive plaster, a suppository and the like. The compound can be administered alone, or as a part of a pharmaceutically acceptable composition containing a pharmaceutically acceptable-excipient. It is also possible to administer simultaneously or sequentially one or more kinds of the compounds of the aforementioned formula (I).

Solid compositions for oral administration include tablet, pill, capsule, powder, granule and the like. Capsules include hard capsule and soft capsule. In such a solid composition, one or more active substances are admixed with at least one inert diluent, such as lactose, mannitol, glucose, hydroxypropyl cellulose, microcrystalline cellulose, starch, polyvinyl pyrrolidone and metamagnesium silicate aluminate. The composition may contain an additive other than the inert diluent, such as lubricant (e.g., talc, magnesium stearate, solid polyethylene glycol, sodium lauryl sulfate), disintegrant (e.g., calcium cellulose glucolate), stabilizer (e.g., lactose) and dissolution aids (e.g., glutamine acid, aspartic acid), according to a conventional method. Tablet and pill may be coated with a film of a gastric-soluble or enteric substance as necessary, such as sucrose, gelatin, hydroxypropyl cellulose, hydroxypropylmethylcellulose phthalate and the like, or may be coated with two or more layers. Furthermore, capsules made from an absorbable substance such as gelatin are also encompassed.

Liquid compositions for oral administration include pharmaceutically acceptable solution, emulsifier, suspension, syrup, elixir and the like, and may contain inert diluent generally used, such as water and other solvents, solubilizing agent and emulsifier, such as ethyl alcohol, isopropyl alcohol, ethyl carbonate, ethyl acetate, benzyl alcohol, benzyl benzoate, propylene glycol, 1,3-butylen e glycol, dimethylformamide, cottonseed oil, Apios americana oil, corn germ oil, olive oil, castor oil, and sesame oil, glycerol, tetrahydrofurfuryl alcohol, polyethylene glycol and sorbitan fatty acid ester, a mixture of these substances and the like. Besides these inert diluents, the composition may contain an aid such as wetting agent and suspending agent, sweetener, flavoring agent, fragrance agent and preservative.

A suspension may contain, besides the active compound, suspending agent such as ethoxyl isostearyl alcohol, polyoxyethylenesorbitol and sorbitan ester, microcrystalline cellulose, aluminum metahydroxide, bentonite, agar and tragacanth, a mixture of these substances and the like.

Other composition for oral administration contains one or more active substances, and includes a spray agent formulated according to a method known per se. This composition may contain, other than an inert diluent, a stabilizer such as sodium hydrogensulfite and a buffer affording isotonicity, such as sodium chloride, sodium citrate and citric acid. The production method of the spray agent is described in, for example, U.S. Pat. Nos. 2,868,691 and 3,095,355.

The composition for injection of the present invention for parenteral administration includes physiologically acceptable sterilized aqueous or nonaqueous solution, suspension and emulsifier. The aqueous solution and suspension are exemplified by distilled water for injection and physiological saline. As the water-insoluble solution and suspension, for example, propylene glycol, polyethylene glycol, olive oil, ethanol, polysorbate 80 and the like can be mentioned. Such compositions may contain an aid such as preservative, wetting agent, emulsifier, dispersing agent, stabilizer (e.g., lactose) and dissolution aids (e.g., glutamic acid, aspartic acid). These are sterilized by, for example, filtration through a bacteria retention filter, addition of sterilizing agent or irradiation. It is also possible to produce a sterilized solid composition, which is dissolved in sterilized water or sterilized solvent for injection, before use of, for example, a lyophilized product.

Other compositions for parenteral administration include external liquid, ointment, liniment, suppository, pessary and the like, which contain one or more active substances and are prescribed by conventional methods.

EXAMPLES

The present invention is explained in detail in the following by referring to Synthetic Examples and Examples, which are not to be construed as limitative as long as they are within the scope of the present invention. In the following, unless particularly indicated, each operation means the following.

1) The reaction operation was performed at an ambient temperature, or 18-25° C., in an inert gas, for example, under a nitrogen atmosphere.

2) The concentration was done using a rotary evaporator under reduced pressure, and drying was done on, for example, anhydrous sodium sulfate, and desiccant was removed by filtration.

3) For purification, for example, recrystallization, suspension-washing comprising stirring in a suspension state, sublimation, or column chromatography (by flushing method) was used. For column chromatography, a suitable developer, such as chloroform-methanol and the like, was used.

4) The structure of the objective product of the aforementioned formula (I) was confirmed by proton ($^1$H or 1H) nuclear magnetic resonance (NMR) (300 MHz or 270 MHz, 300 MHz unless particularly specified) and/or mass spectrum: $^1$H NMR was measured in deuterated dimethyl sulfoxide (DMSO-$d_6$, DMSO-$d_6$) or deuterated chloroform (CDCl$_3$, CDCl$_3$) unless particularly specified, chemical shift value is expressed by delta values (δ ppm) based on tetramethylsilane (TMS), and the peak multiplicity is expressed according to the following: s, singlet; d, doublet; t, triplet; q, quartet; m, multiplet; br, broad peak.

5) The following abbreviations were used: n-hexane (Hex or hexane); Ac acetyl group; Ms methanesulfonyl group; Tf trifluoromethanesulfonyl group; EDC 1-[3-(diethylamino)propyl]-3-ethylcarbodiimide hydrochloride.

6) Powder X-ray diffraction pattern was measured according to the following conditions.
Diffractometer: PHILIPS PW1700
Target: Cu
Monochro.: Graphite
Tube Voltage: 40 kV
Tube Current: 30 mA
Divergence Slit: 1°
Receiving Slit: 0.2 mm
Scatter Slit: 1°
Range: 3-40° 2θ

Synthetic Example 1

1-(1,1-dimethyl-2-propynyl)-4-methylpiperazine (4a)

A solution of acetic acid 1,1-dimethyl-2-propynyl ester (2-methyl-3-butyn-2-yl acetate) (51.5 g, 408.2 mmol), copper chloride (I) (2.02 g, 20.4 mmol), triethylamine (56.6 mL, 408.2,mmol) and 1-methylpiperazine (54.3 mL, 489.9 mmol) in THF (480 mL) was reacted under reflux for 2 hrs. The reaction mixture was concentrated, and tert-butylmethyl ether (200 mL) was added to the residue. The product was extracted with dilute hydrochloric acid. 6N Aqueous sodium hydroxide solution was added to the extract with stirring under ice-cooling until the aqueous layer showed basicity, and the mixture was extracted with dichloromethane (500 mL×1, 150 mL×3). The extracts were washed with 14% aqueous ammonia, and then with saturated brine, dried and concentrated. The resulting brown solid was purified by sublimation (60° C./5-6 Torr) to give the title compound as colorless crystals (49.07 g, 72%).

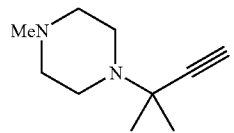

4a: $^1$H NMR (CDCl$_3$) δ ppm: 1.40 (s, 6H), 2.28 (s, 1H), 2.28 (s, 3H), 2.49 (br s, 4H), 2.69 (br s, 4H).

Synthetic Example 2

N$^4$-(3-chloro-4-fluorophenyl)-7-[3-methyl-3-(4-methyl-1-piperazinyl)-1-butynyl]-4,6-quinazolinediamine (2a)

1) A mixture (about 3:1, 52.0 g; described in Leonard et al., J. Org. Chem. 1975, 40, 356-363) of 7-chloro-6-nitro-3H-quinazolin-4-one and 7-chloro-8-nitro-3H-quinazolin-4-one and DMF (0.7 mL) were added to thionyl chloride (200 mL) and the mixture was heated under reflux for 4 hrs. The reaction mixture was concentrated to dryness and toluene (150 mL) was added. The mixture was concentrated further. This step was repeated twice and dichloromethane (280 mL) was added to the residue. The mixture was stirred at room temperature. To this suspension was added dropwise a solution (760 mL) of 3-chloro-4-fluoroaniline (36.9 g, 253.6 mmol) in isopropanol. Dichloromethane (300 mL) was added and the mixture was stirred, at 20° C. for 20 min. Hexane (600 mL) was added under ice-cooling, and stirring was continued at 20° C. The precipitate was collected by filtration, washed with hexane (200 mL×2) and dried under reduced pressure. The obtained solid was added to methanol (1 L)-water (120 mL), and triethylamine (30 mL) was added with stirring under ice-cooling. After stirring at room temperature for 1 hr, the precipitate was collected by filtration and washed with water (700 mL×2). The crudely purified substance (65 g) was suspension-washed with acetonitrile (1.2 L) with heating, and collected by filtration to give the objective (7-chloro-6-nitro-4-quinazolinyl)-(3-chloro-4-fluorophenyl)amine (54.6 g, 67%).

2) Nitrogen was passed through a solution (70 mL) of (7-chloro-6-nitro-4-quinazolinyl)-(3-chloro-4-fluorophenyl)amine (14.2 g. 40.1 mmol), 1-(1,1-dimethyl-2-propynyl)-4-methylpiperazine (4a) (10.0 g, 60.1 mmol), copper iodide (I) (380 mg), and tetrakis(triphenylphosphine)palladium (1.39 g) in DMF at 50° C. for 15 mm and triethylamine (13.9 mL, 100.0 mmol) was added and the mixture was stirred at an oil bath temperature of 140° C. for 50 mm. The reaction mixture was allowed to cool and concentrated. Aqueous sodium hydrogen carbonate (300 mL) was added, and the product was extracted with ethyl acetate (200 mL×2), dried and concentrated. The residue was subjected to silica gel column chromatography (chloroform-methanol; ethyl acetate-methanol) to give the objective nitro compound of (3-chloro-4-fluorophenyl)-{7-[3-methyl-3-(4-methyl-1-piperazinyl)-1-butynyl]-6-nitro-4-quinazolinyl}amine (3a) (7.25 g, 37%).

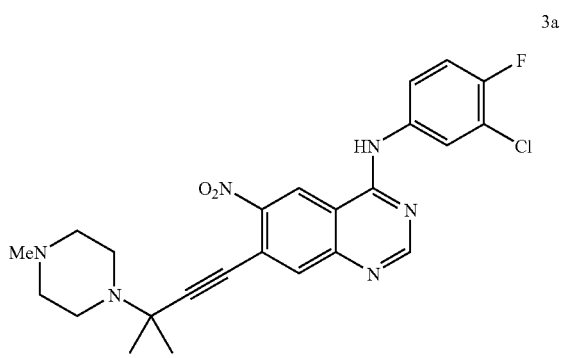

3a: $^1$H NMR (CDCl$_3$) δ ppm: 1.54 (s, 6H), 2.28 (s, 3H), 2.53 (s, 4H), 2.82 (s, 4H), 7.21 (t, J=8.7 Hz, 1H), 7.59 (m, 1H), 7.99 (m, 1H), 8.08 (s, 1H), 8.80 (s, 1H), 8.81 (s, 1H).

3) A suspension of nitro compound 3a (3.69 g, 7.64 mmol), acetic acid (5 mL) and iron powder (1.71 g, 30.6 mmol) in ethanol (100 mL)-water (50 mL) was refluxed for 20 min. 10% Aqueous sodium carbonate solution (90 mL) was added to the reaction mixture under ice-cooling, and the mixture was stirred at room temperature for 1 hr and filtered through Celite. The residue was washed with ethanol (150 mL×3) and the filtrate was concentrated. Water (100 mL) was added and the precipitate was collected by filtration. The product was washed with water and dried under reduced pressure to give the objective amino form, N$^4$-(3-chloro-4-fluorophenyl)-7-[3-methyl-3-(4-methyl-1-piperazinyl)-1-butynyl]-4,6-quinazolinediamine (2a) (3.02 g, 87%).

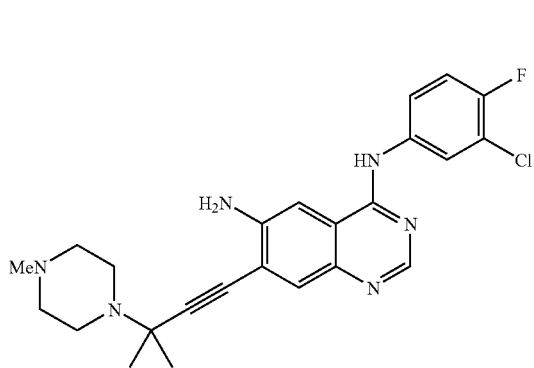

2a: $^1$H NMR (CDCl$_3$) δ ppm: 1.55 (s, 6H), 2.30 (s, 3H), 2.53 (br s, 4H), 2.80 (br s, 4H), 4.53 (br s, 2H), 6.93 (s, 1H), 7.11, (s, 1H), 7.17 (t, J=8.8 Hz, 1H), 7.53 (m, 1H), 7.88 (s, 1H), 7.93 (dd, J=2.5, 6.5 Hz, 1H), 8.58 (s, 1H).

Synthetic Example 3

(7-bromo-6-nitro-4-quinazolinyl)-(3-chloro-4-fluorophenyl)amine

1) A solution (250 mL) of 2,5-dibromo-1-nitrobenzene (4.32 g, 15.4 mmol) in THF was cooled to −105° C. and 0.88 M phenyllithium/THF solution (19.8 mL, 17.4 mmol) was slowly added dropwise. After 30 min, DMF (5.4 mL, 69.6 mmol) was slowly added dropwise and the temperature was slowly raised to −20° C. Dilute aqueous sulfuric acid solution (100 mL) was added to the reaction mixture and the mixture was concentrated. The product was extracted with ethyl acetate (80 mL×2). The organic layer was dried, concentrated and the resulting brown solid (5.66 g) was dissolved in acetone (50 mL). Jone's reagent (20 mL) was slowly added to this solution under ice-cooling, and the temperature was slowly raised to room temperature. Isopropanol was added to the reaction mixture and the mixture was concentrated. 2 mol/L Aqueous sodium hydroxide solution (100 mL) was added and the mixture was filtered. Concentrated hydrochloric acid was added to acidify the filtrate. The precipitate was collected by filtration and the residue was washed with water and dried to give 4-bromo-2-nitrobenzoic acid (1.95 g, 52%).

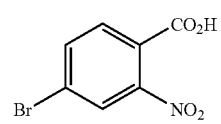

$^1$H NMR (DMSO-d$_6$) δ ppm: 7.80 (br s, 1H), 7.98 (br s, 1H), 8.25 (br s, 1H), 14.1 (br s, 1H).

2) To 4-bromo-2-nitrobenzoic acid (1.80 g, 7.83 mmol) were added 0.88N aqueous sodium hydroxide solution (10 mL), iron(III) chloride (133 mg) and isopropyl alcohol (0.7 mL) and the mixture heated to 75° C. While stirring the mixture, hydrazine (1.1 mL) was slowly added, and the mixture was reacted at 75° C. for 2 hrs. The reaction mixture was filtered and the filtrate was concentrated. The precipitated solid was washed with water to give 4-bromoanthranilic acid (1.73 g, 96%).

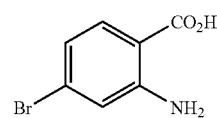

$^1$H NMR (DMSO-d$_6$) δ ppm: 6.62 (dd, J=1.5, 8.5 Hz, 1H), 6.95 (d, J=1.5 Hz, 1H), 7.56 (d, J=8.5 Hz, 1H).

3) Formamidine acetate (1.96 g, 18.9 mmol) and 2-ethoxyethanol (25 mL) were added to 4-bromoanthranyl acid (1.63 g, 7.55 mmol) and the mixture was heated under reflux for 7 hrs. Formamidine acetate (1.45 g) was added and the mixture was further refluxed for 6 hrs. Dilute aqueous ammonia solution (30 mL) was added, and after stirring for a while, the product was collected by filtration and dried to give the objective 7-bromo-3H-quinazolin-4-one (1.67 g, 98%).

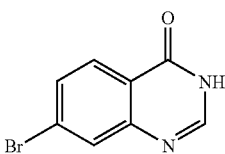

$^1$H NMR (DMSO-d$_6$) δ ppm: 7.69 (dd, J=1.9, 8.4 Hz, 1H), 7.89 (d, J=1.9 Hz, 1H), 8.04 (d, J=8.4 Hz, 1H), 8.14 (br s, 1H).

To a mixed solution of concentrated sulfuric acid (3 mL) and fuming nitric acid (3 mL) was added 7-bromo-3H-quinazolin-4-one (1.67 g, 7.42 mmol), and the mixture was heated at an oil bath temperature of 95° C. to 100° C. for 1 hr. The reaction mixture was poured into water (50 mL), and the product was collected by filtration, washed with water and dried under reduced pressure to give an about 5.6:1 mixture (1.3 g, 65%) of the objective 7-bromo-6-nitro-3H-quinazolin-4-one and 7-bromo-8-nitro-3H-quinazolin-4-one.

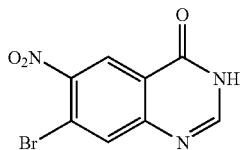

7-bromo-6-nitro-3H-quinazolin-4-one $^1$H NMR (DMSO-$d_6$) δ ppm: 8.15 (s, 1H), 8.27 (s, 1H), 8.61 (s, 1H).

This mixture (1.26 g) was converted to (7-bromo-6-nitro-4-quinazolinyl)-(3-chloro-4-fluorophenyl)amine (1.38 g, 74%) in the same manner as in Synthetic Example 2-1).

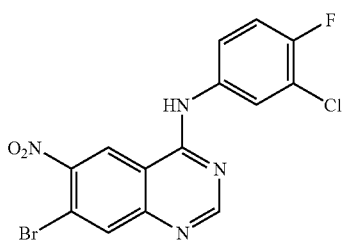

(7-bromo-6-nitro-4-quinazolinyl)-(3-chloro-4-fluorophenyl)amine $^1$H NMR (DMSO-$d_6$) δ ppm: 7.46 (t, J=9.2 Hz, 1H), 7.77 (m, 1H), 8.13 (m, 1H), 8.25 (s, 1H), 8.73 (s, 1H), 9.33 (s, 1H), 10.37 (br s, 1H).

Synthetic Example 4

(7-bromo-6-nitro-4-quinazolinyl)-(3-chloro-4-fluorophenyl)amine hydrochloride

1) To a solution of 2,5-dibromonitrobenzene (80 g, 285 mmol) in DMF (500 mL) was added copper cyanide (I) (38 g, 427 mmol) and the mixture was stirred at 100° C. for 1.5 hrs. The reaction mixture was allowed to reach room temperature and toluene (750 mL)-water (1250 mL) was added. Then, Celite (50 g) was added, and after thorough stirring, insoluble material was filtered off. The filtrate was partitioned and the organic layer was washed successively with water (500 mL), 1% aqueous ammonia (250 mL×2), water (250 mL) and saturated brine (500 mL), and dried over anhydrous sodium sulfate, after which the solvent was evaporated under reduced pressure to give a yellow solid (61.4 g) containing 2-cyano-5-bromonitrobenzene as a main component. This was dissolved in ethyl acetate (270 mL) and platinum oxide monohydrate (330 mg, 1.35 mmol) was added. The inside of the reaction container was displaced with hydrogen and the mixture was stirred under a hydrogen atmosphere for 41.5 hrs. Insoluble material was filtered off and the residue was washed with ethyl acetate (200 mL) and then with ethanol (100 mL). The filtrate was evaporated under reduced pressure, and after drying, suspended in ether (250 mL). The suspension was stirred with heating under reflux. The mixture was allowed to cool to room temperature and the insoluble material was collected by filtration to give 4-bromoanthranilic amide (40 g, 186 mmol, 65%).

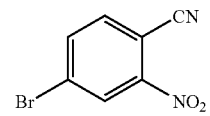

2-cyano-5-bromonitrobenzene $^1$H NMR (DMSO-$d_6$) δ ppm: 8.10 (d, J=8.3 Hz, 1H), 8.21 (dd, J=1.8, 8.3 Hz, 1H), 8.57 (d, J=1.8 Hz, 1H)

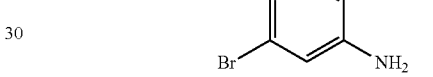

4-bromoanthranilic amide $^1$H NMR (DMSO-$d_6$) δ ppm: 6.61 (dd, J=1.8, 8.4 Hz, 1H), 6.81 (br s, 2H), 6.89 (d, J=1.8 Hz), 7.17 (br s, 1H), 7.46 (d, J=8.4 Hz, 1H), 7.79 (br s, 1H).

2) 4-Bromoanthranilic amide (40 g, 186 mmol) obtained in 1) was dissolved in ethanol (400 mL). Thereto was added sodium methoxide (54.2 g, 93 mmol) with stirring under ice-cooling and then ethyl formate (60.1 mL, 744 mmol) was added dropwise. The mixture was heated under reflux for 1.5 hrs. The reaction mixture was allowed to cool to room temperature and water (500 mL) was added and then acetic acid (40 mL) was added. The mixture was concentrated under reduced pressure and water (200 mL) was added. The precipitate was collected by filtration and dried to give 7-bromo-3H-quinazolin-4-one (35 g, 156 mmol, 84%).

7-bromo-3H-quinazolin-4-one $^1$H NMR (DMSO-$d_6$) δ ppm: 7.68 (dd, J=1.7, 8.5 Hz, 1H), 7.88 (d, J=1.7 Hz, 1H), 8.03 (d, J=8.5 Hz, 1H), 8.14 (s, 1H).

3) 7-Bromo-3H-quinazolin-4-one (35 g, 156 mmol) obtained in 2) was dissolved in sulfuric acid (56 mL) and stirred on an oil bath at 90° C. Thereto was added dropwise fuming nitric acid (56 mL) by small portions while maintaining the temperature of the reaction mixture at not higher than 120° C. After the completion of the dropwise addition, the mixture was further stirred with heating at 90° C. for 1 hr. The reaction mixture was allowed to cool to room temperature and poured into ice water (1.5 L). The precipitated solid was collected by filtration and washed with water (500 mL). Drying gave a mixture (about 3:1, 37 g) of 7-bromo-6-nitro-3H-quinazolin-4-one and 7-bromo-8-nitro-3H-quinazolin-4-one. Thereto was added thionyl chloride (205 mL) and DMF (2.5 mL) and the mixture was heated under reflux for 2 hrs. The reaction mixture was concentrated to dryness under reduced pressure. Thereto was added dichloromethane (370 mL) and a solution of 3-chloro-4-fluoroaniline (21.9 g, 151 mmol) in isopropanol (1.1 L) was added dropwise with stirring at room temperature. The mixture was further stirred for 4 hrs. Hexane (1.1 L) was added to the reaction mixture and the precipitate was collected by filtration. Drying gave (7-bromo-6-nitro-4-quinazolinyl)-(3-chloro-4-fluorophenyl)amine hydrochloride (42.7 g, 98.4 mmol, 72%).

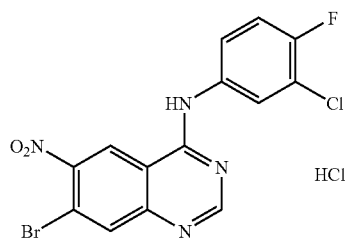

(7-bromo-6-nitro-4-quinazolinyl)-(3-chloro-4-fluorophenyl)amine hydrochloride $^1$H NMR (DMSO-$d_6$) δ ppm: 7.52 (t, J=9.0 Hz, ,1H), 7.81 (m, 1H), 8.15 (m, 1H), 8.33 (s, 1H), 8.86 (s, 1H), 9.54 (s, 1H), 11.16 (br s, 1H).

4) A solution of (7-bromo-6-nitro-4-quinazolinyl)-(3-chloro-4-fluorophenyl)amine hydrochloride (42.0 g, 96.8 mmol), 1-(1,1-dimethyl-2-propynyl)-4-methylpiperazine (4a) (19.3 g, 116 mmol) and triethylamine (47.2 mL, 339 mmol) in DMSO (400 mL) was subjected 3 times to the step of degassing under reduced pressure and then displacement with nitrogen. Copper iodide (I) (460.8 mg, 2.4 mmol), triphenylphosphine (2.53 g, 9.6 mmol) and palladium(II) acetate (543 mg, 2.4 mmol) were added. The mixture was stirred at 80° C. for 9 hrs and allowed to cool to room temperature. The mixture was poured into ethyl acetate (750 mL) and 1% aqueous ammonia solution (1.5 L), and Celite (50 g) was added, which was followed by stirring. Insoluble material was filtered off and the organic layer was washed with brine (500 mL×2) and dried over anhydrous sodium sulfate. The solvent was evaporated under reduced pressure and ethyl acetate-methanol mixed solvent (10:1, 130 mL) was added to the residue. The mixture was stirred and the precipitate was collected by filtration. The filtered product was suspension-washed with acetonitrile (100 mL) and dried to give a nitro compound 3a (23.3 g, 48.3 mmol, 50%).

Example 1

A solution of the amino compound 2a (6.08 g, 13.4 mmol) obtained by the method of Synthetic Example 2, acrylic acid (1.38 mL, 20.1 mmol), triethylamine (2.8 mL, 20.1 mmol) and EDC (3.86 g, 20.1 mmol) in DMF (100 mL) was stirred overnight at room temperature. Acrylic acid (0.46 mL, 6.71 mmol), triethylamine (0.93 mL, 6.71 mmol) and EDC (1.29 g, 6.71 mmol) were added to the reaction mixture and the mixture was further stirred overnight. The reaction mixture was poured into aqueous sodium hydrogen carbonate (300 mL) and the mixture was filtered. The residue was washed with water and water-ethanol and dried. The crudely purified substance was stirred with heating in water-ethanol and cooled to room temperature. The precipitate was collected by filtration and dried to give the objective compound 1a (3.41 g, 50%).

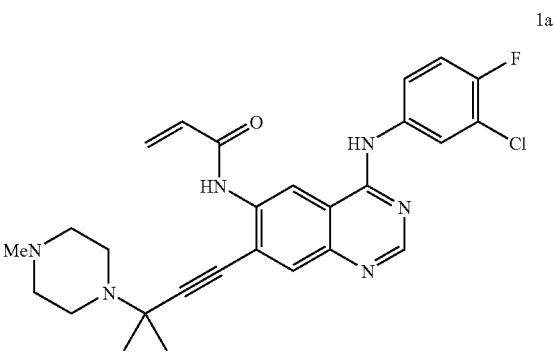

1a: $^1$H NMR (DMSO-$d_6$) δ ppm: 1.44 (s, 6H), 2.15 (s, 3H), 2.35 (br s, 4H), 2.64 (br s, 4H), 5.85 (d, J=10.3 Hz, 1H), 6.33 (d, J=16.9 Hz, 1H), 6.58 (dd, J=10.3, 16.9 Hz, 1H), 7.47 (t, J=9.1 Hz, 1H), 7.84 (br s, 2H), 8.20 (br d, J=6.1 Hz, 1H), 8.64 (s, 1H), 8.69 (s, 1H), 9.88 (s, 1H), 10.01 (s, 1H).

Example 2

In the same manner as in Synthetic Example 2-2) 3) and using (7-bromo-6-nitro-4-quinazolinyl)-(3-chloro-4-fluorophenyl)amine obtained by the method of Synthetic Example 3 and 1-(1,1-dimethyl-2-propynyl)morpholine (4b), amino compound 2b was obtained. In the same manner as in Example 1, compound 1b was obtained from compound 2b.

Note that 4b used for the reaction was produced in the same manner as in Synthetic Example 3 using morpholine instead of 1-methylpiperazine.

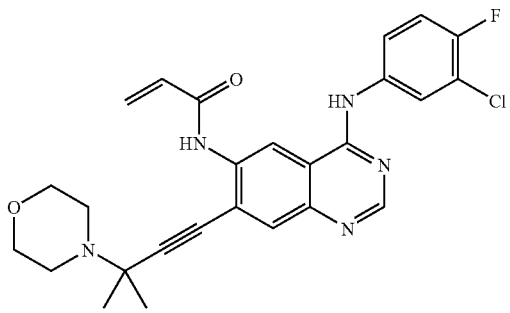

1b (yield 87%): $^1$H NMR (DMSO-$d_6$) δ ppm: 1.43 (s, 6H), 2.61 (m, 4H), 4.18 (m, 4H), 5.84 (d, J=10.2 Hz, 1H), 6.33 (d, J=16.9 Hz, 1H), 6.56 (dd, J=10.2, 16.9 Hz, 1H), 7.44 (t, J=9.1 Hz, 1H), 7.80-8.00 (m, 2H), 7.95 (m, 1H), 8.60-8.70 (m, 2H), 9.85-9.90 (m, 2H).

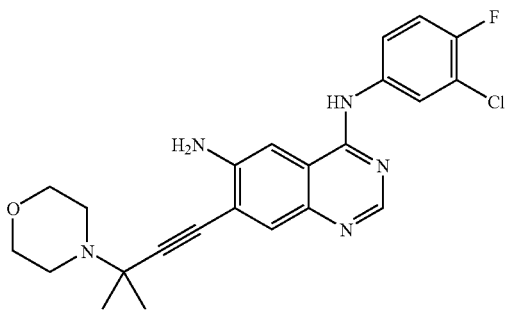

2b (yield 79%): ¹H NMR (DMSO-d₆) δ ppm: 1.47 (s, 6H), 2.64 (m, 4H), 3.65 (m, 4H), 5.55 (m, 2H), 7.43 (t, J=9.2 Hz), 7.52 (s, 1H), 7.65 (s, 1H), 7.82 (m, 1H), 8.20 (m 1H), 8.39 (m 1H), 9.64 (s, 1H).

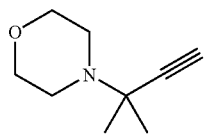

4b (yield 73%): ¹H NMR (DMSO-d₆) δ ppm: 1.39 (s, 6H), 2.31 (s, 1H), 2.64 (t, J=4.7 Hz, 4H), 3.75 (t, J=4.7 Hz, 4H).

Synthetic Example 5

7-bromo-N⁴-(3-chloro-4-fluorophenyl)-4,6-quinazolinediamine (5)

Reduced iron (84.2 g, 1.51 mol) and 1.5 mol/L hydrochloric acid (605 mL) were added to ethanol (2.5 L) and the mixture was heated to 90° C. with stirring. To this mixture was added (7-bromo-6-nitro-4-quinazolinyl)-(3-chloro-4-fluorophenyl)amine 4 times (30 g each time) every 30 min. The mixture was heated under reflux for 5 hrs and the inner temperature was set to 50° C. 2N Aqueous sodium hydroxide solution (450 mL) and 1N aqueous sodium hydroxide solution were added to adjust the pH thereof to 7-8 and the mixture was stirred for a while. Ethyl acetate (1 L) and Celite (300 g) were added, and after stirring for a while, the mixture was filtered through Celite. The residue was washed with THF-ethyl acetate (1:1, 1 L) and the filtrate was concentrated under reduced pressure. Water (1 L) was added to the concentrate and the product was collected by filtration and dried under reduced pressure at 60° C. overnight to give the title compound (108.76 g, 98%).

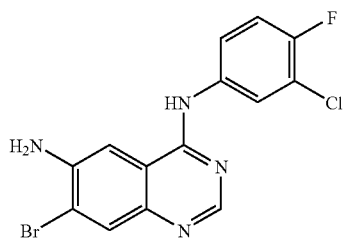

5: ¹H NMR (DMSO-d₆) δ ppm: 5.77 (s, 2H), 7.43 (t, J=9.3 Hz, 1H), 7.60 (s, 1H), 7.80 (m, 1H), 7.94 (s, 1H), 8.18 (dd, J=6.9, 2.1 Hz, 1H), 8.39 (s, 1H), 9.72 (s, 1H).

Synthetic Example 6

Synthesis of [4-(1,1-dimethyl-2-propynyl)-1-piperazinyl]acetonitrile (4c)

To a suspension (10 mL) of 1-(1,1-dimethyl-2-propynyl)piperazine (350 mg, 2.3 mmol) and potassium carbonate (480 mg, 3.45 mmol) in methyl ethyl ketone (MEK) was added bromoacetonitrile (0.176 mL, 2.53 mmol), and the mixture was stirred at room temperature for 30 min. The reaction mixture was diluted with MEK and filtered. The filtrate was concentrated to give the title compound (0.439 g, quantitative) as a white solid.

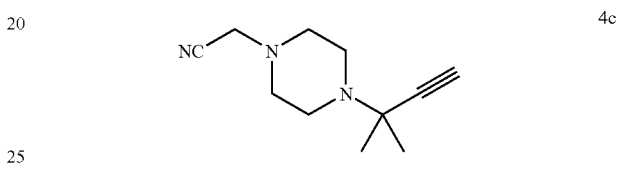

4c: ¹H NMR (300 MHz, CDCl₃) δ ppm: 1.40 (s, 6H), 2.31 (s, 1H), 2.68 (br s, 8H), 3.52 (s, 2H).

Example 3

1) Triethylamine (15 mL) and DMF (3.5 mL) were added to compound 5 (1.0 g, 2.72 mmol) and [4-(1,1-dimethyl-2-propynyl)-1-piperazinyl]acetonitrile (4c) (624 mg, 3.26 mmol). This mixture was subjected 3 times to the step of degassing under reduced pressure and displacement with nitrogen, and triphenylphosphine (35 mg, 0.16 mmol) and palladium (II) acetate (18 mg, 0.08 mmol) were added. The mixture was stirred at 80° C. for 4 hrs. The reaction mixture was allowed to cool to room temperature and the solvent was evaporated under reduced pressure. Aqueous sodium hydrogen carbonate was added to the residue and the mixture was extracted with ethyl acetate. The organic layer was washed successively with water and saturated brine and dried over anhydrous sodium sulfate. The solvent was evaporated under reduced pressure and the residue was subjected to silica gel column chromatography (ethyl acetate-methanol) to give the objective coupling compound 2c (1.07 g, 82%).

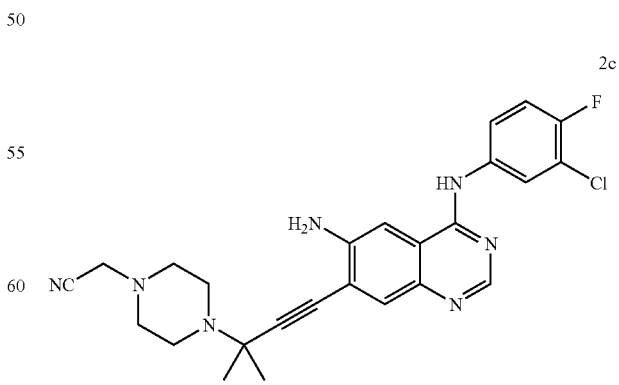

2c: ¹H NMR (270 MHz, DMSO-d₆) δ ppm: 1.48 (s, 6H), 2.56 (br s, 4H), 2.70 (br s, 4H), 3.73 (s, 2H), 5.54 (s, 2H), 7.42 (t, J=8.9 Hz, 1H), 7.51 (s, 1H), 7.64 (S, 1H), 7.81 (m, 1H), 8.20 (dd, J=6.9, 2.4 Hz, 1H), 8.39 (s, 1H), 9.64 (s, 1H).

2) A solution of compound 2c (500 mg, 1.04 mmol), acrylic acid (0.36 mL, 5.2 mmol), triethylamine (0.22 mL, 1.56 mmol) and EDC (297 mg, 1.56 mmol) in DMF (7 mL) was stirred overnight at room temperature. The reaction mixture was evaporated under reduced pressure and poured into aqueous sodium hydrogen carbonate (70 mL). The mixture was filtered and the residue was washed with water and water-ethanol. The purified crude substance was subjected to silica gel column chromatography (chloroform-methanol) and the obtained solid was recrystallized from water-ethanol to give the objective compound 1c (338 mg, 61%).

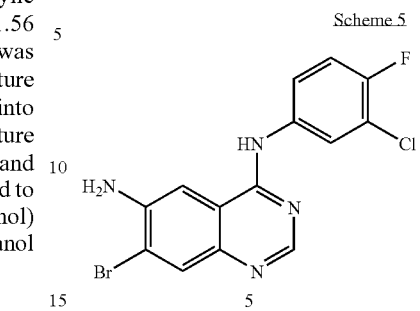

Scheme 5

1c: $^1$H NMR (DMSO-$d_6$) δ ppm: 1.44 (s, 6H), 2.50 (br s, 4H), 2.67 (br s, 4H), 3.71 (s, 2H), 5.84 (d, J=10.1 Hz, 1H), 6.32 (d, J=16.9 Hz, 1H), 6.56 (dd, J=16.9, 10.1 Hz, 1H), 7.46 (t, J=9.2 Hz, 1H), 7.84 (br s, 2H), 8.18 (br d, J=6.8 Hz, 1H), 8.63 (s, 1H), 8.67 (s, 1H), 9.89 (s, 1H), 9.99 (s, 1H).

Examples 4-25

In the same manner as in Example 3 and using 7-bromo-N$^4$-(3-chloro-4-fluorophenyl)-4,6-quinazolinediamine (5) and the corresponding acetylene compound 4 as starting materials, amines 2 and compounds 1 were produced as shown in the following (Scheme 5). Each spectrum data are shown in Table 10.

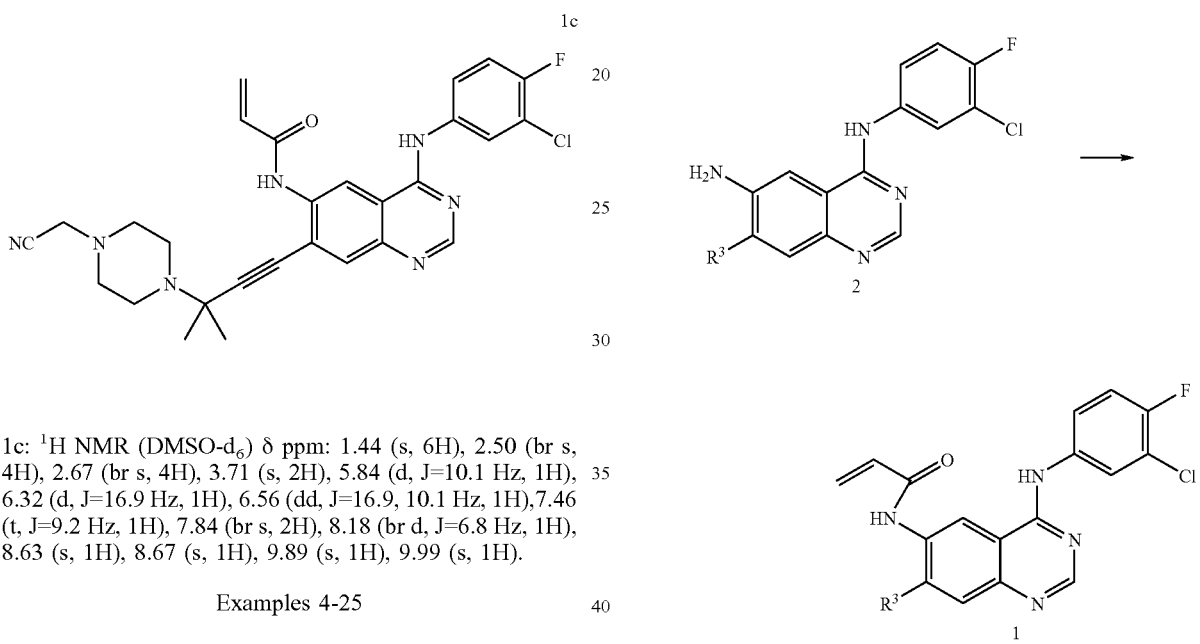

TABLE 10

| Ex. | R$^3$ | Compound 1 (yield) | Compound 2 (yield) | Compound 4, R3—H |
|---|---|---|---|---|
| 4 | OMe (structure: MeO-CH2CH2-N(CH2CH2-OMe)-C(CH3)2-C≡C-) | 1d(40%):<br>1H NMR(270 MHz, DMSO-d6) δ ppm:<br>1.43(s, 6H),<br>2.82(t, J=6.8 Hz, 4H),<br>3.24(s, 6H), 3.33-3.50(m, 4H),<br>5.85(dd, J=10.0, 1.9 Hz, 1H),<br>6.33(dd, J=17.0, 1.9 Hz, 1H),<br>6.56(dd, J=17.0, 10.0 Hz, 1H),<br>7.46(t, J=9.2 Hz, 1H),<br>7.83(br s, 2H),8.18(br d, J=7.0 Hz, 1H), 8.63(s, 1H), 8.68(s, 1H), 9.88(s, 1H), 9.99(s, 1H). | 2d(62%):<br>1H NMR(270 MHz, DMSO-d6) δ ppm:<br>1.47(s, 6H),<br>2.86(t, J=6.8 Hz, 4H),<br>3.26(s, 6H),<br>3.43(t, J=6.8 Hz, 4H),<br>5.56(s, 2H),<br>7.42(t, J=9.2 Hz, 1H),<br>7.51(s, 1H), 7.64(s, 1H),<br>7.83(m, 1H),<br>8.21(dd, J=6.8, 2.4 Hz, 1H),<br>8.39(s, 1H), 9.62(s, 1H). | 4d·HCl(51%):<br>1H NMR(300 MHz, CDCl3) δ ppm:<br>1.91(s, 6H), 2.68(s, 1H),<br>3.47(s, 6H), 3.57-3.75(m, 4H), 3.80-3.90(m, 2H), 4.00-4.15(m, 2H), 12.23(br s, 1H). |

TABLE 10-continued

| Ex. | R³ | Compound 1 (yield) | Compound 2 (yield) | Compound 4, R3—H |
|---|---|---|---|---|
| 5 | 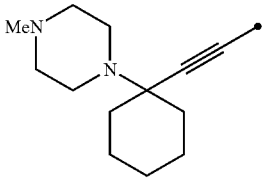 | 1e(36%): 1H NMR(270 MHz, DMSO-d6) δ ppm: 1.26(m, 1H), 1.50-1.64(m, 7H), 2.00(m, 2H), 2.15(s, 3H), 2.35(br s, 4H), 2.64(br s, 4H), 5.83(dd, J=10.0, 1.9 Hz, 1H), 6.31(dd, J=17.0, 1.9 Hz, 1H), 6.55(dd, J=17.0, 10.0 Hz, 1H), 7.46(t, J=8.9 Hz, 1H), 7.85(br s,2H), 8.19(br d, J=6.8 Hz, 1H), 8.64(s, 1H), 8.65(s, 1H), 9.88(s, 1H), 9.99(s, 1H). | 2e(89%): 1H NMR(270 MHz, DMSO-d6) δ ppm: 1.35(m, 1H), 1.50-1.75(m, 7H), 1.99(m, 2H), 2.20(s, 3H), 2.45(br s, 4H), 2.67(br s, 4H), 5.50(s, 2H), 7.43(t, J=8.9 Hz, 1H), 7.54(s, 1H), 7.66(s, 1H), 7.79-7.85(m, 1H), 8.21(dd, J=7.0, 2.7 Hz, 1H), 8.40(s, 1H), 9.65(s, 1H). | 4e(83%): 1H NMR(300 MHz, DMSO-d6) δ ppm: 1.13-1.31(m, 1H), 1.32-1.52(m, 5H), 1.52-1.70(m, 2H), 1.70-1.87(m, 2H), 2.13(s, 3H), 3.20-2.41(m, 4H), 2.41-2.65(m, 4H), 3.18(s, 1H). |
| 6 | 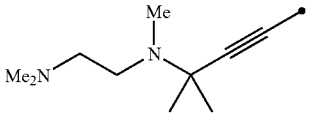 | 1f(30%): 1H NMR(270 MHz, DMSO-d6) δ ppm: 1.42(s, 6H), 2.14(s, 6H), 2.26(s, 3H), 2.31(t, J=7.2 Hz, 2H), 2.56(t, J=7.2 Hz, 2H), 5.84(dd, J=10.0, 1.9 Hz, 1H), 6.33(dd, J=16.7, 1.9 Hz, 1H), 6.56(dd, J=16.7, 10.0 Hz, 1H), 7.46(t, J=9.2 Hz, 1H), 7.84(br s,2H), 8.18(br d, J=7.0 Hz, 1H), 8.62(s, 1H), 8.67(s, 1H), 9.90(s, 1H), 10.00(s, 1H). | 2f(70%): 1H NMR(270 MHz, DMSO-d6) δ ppm: 1.46(s, 6H), 2.16(s, 6H), 2.30(s, 3H), 2.35(t, J=7.6 Hz, 2H), 2.61(t, J=7.6 Hz, 2H), 5.55(s, 2H), 7.42(t, J=9.2 Hz, 1H), 7.50(s, 1H), 7.63(s, 1H), 7.81(m, 1H), 8.20(dd, J=6.8, 2.7 Hz, 1H), 8.39(s, 1H), 9.63(s, 1H). | 4f(78%): 1H NMR(300 MHz, DMSO-d6) δ ppm: 1.25(s, 6H), 2.10(s, 6H), 2.15(s, 3H), 2.20-2.30(m, 2H), 2.36-2.46(m, 2H), 3.09(s, 1H). |
| 7 | 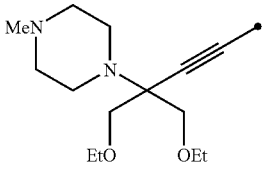 | 1g(44%): 1H NMR(270 MHz, DMSO-d6) δ ppm: 1.11(t, J=7.0 Hz, 6H), 2.11(s, 3H), 2.31(br s, 4H), 2.67(br s, 4H), 3.51(q, J=7.0 Hz, 4H), 3.67(s, 4H), 5.85(dd, J=10.0, 1.9 Hz, 1H), 6.32(dd, J=17.0, 1.9 Hz, 1H), 6.54(dd, J=17.0, 10.0 Hz, 1H), 7.44(t, J=8.9 Hz, 1H), 7.81(br s, 2H), 8.15(br d, J=6.8 Hz, 1H), 8.61(s, 1H), 8.73(s, 1H), 9.74(s, 1H), 10.00(s, 1H). | 2g(73%): 1H NMR(DMSO-d6) δ ppm: 1.15(t, J=7.0 Hz, 6H), 2.16(s, 3H), 2.38(br s, 4H), 2.71(br s, 4H), 3.53(q, J=7.0 Hz, 4H), 3.67(s, 4H), 5.71(s, 2H), 7.43(t, J=9.2 Hz, 1H), 7.50(s, 1H), 7.62(s, 1H), 7.81(m, 1H), 8.20(dd, J=7.0, 2.7 Hz, 1H), 8.38(s, 1H), 9.65(s, 1H). | 4g(83%): 1H NMR(300 MHz, DMSO-d6) δ ppm: 1.09(t, J=6.9 Hz, 6H), 2.14(S, 3H), 2.20-2.45(m, 4H), 2.50-2.70(m, 4H), 3.20(s, 1H), 3.45(q, J=6.9 Hz, 4H), 3.55-3.60(m, 4H). |
| 8 | 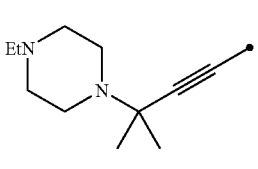 | 1h(50%): 1H NMR(270 MHz, DMSO-d6) δ ppm: 0.98(t, J=7.3 Hz, 3H), 1.43(s, 6H), 2.28(q, J=7.3 Hz, 2H), 2.38(br s, 4H), 2.64(br s, 4H), 5.83(dd, J=10.3, 1.9 Hz, 1H), 6.33(dd, J=17.0, 1.9 Hz, 1H), 6.58(dd, J=17.0, 10.3 Hz, 1H), 7.46(t, J=8.9 Hz, 1H), 7.84(br s,2H), 8.18(br d, J=6.5 Hz, 1H), 8.63(s, 1H), 8.69(s, 1H), 9.87(s, 1H), 10.01(s, 1H). | 2h(85%): 1H NMR(270 MHz, DMSO-d6) δ ppm: 1.00(t, J=7.0 Hz, 3H), 1.47(s, 6H), 2.33(q, J=7.0 Hz, 2H), 2.44(br s, 4H), 2.67(br s, 4H), 5.53(s, 2H), 7.42(t, J=9.2 Hz, 1H), 7.53(s, 1H), 7.65(s, 1H), 7.83(m, 1H), 8.21(dd, J=6.8, 2.4 Hz, 1H), 8.40(s, 1H), 9.63(s, 1H). | 4h(94%): 1H NMR(300 MHz, CDCl3) δ ppm: 1.07(t, J=7.2 Hz, 3H), 2.26(s, 1H), 2.40(q, J=7.2 Hz, 2H), 2.51(br s, 4H), 2.69(br s, 4H). |

TABLE 10-continued

| Ex. | R³ | Compound 1 (yield) | Compound 2 (yield) | Compound 4, R3—H |
|---|---|---|---|---|
| 9 | MeO-CH2CH2-N(Me)- (with dimethyl propargyl) | 1i(53%): 1H NMR(270 MHz, DMSO-d6) δ ppm: 1.42(s, 6H), 2.29(s, 3H), 2.64(t, J=6.2 Hz, 2H), 3.24(s, 3H), 3.40(t, J=6.2 Hz, 2H), 5.85(dd, J=10.0, 1.9 Hz, 1H), 6.33(dd, J=17.0, 1.9 Hz, 1H), 6.56(dd, J=17.0, 10.0 Hz, 1H), 7.46(t, J=8.9 Hz, 1H), 7.84(br s,2H), 8.19(br d, J=7.0 Hz, 1H), 8.63(s, 1H), 8.67(s, 1H), 9.89(s, 1H), 9.99(s, 1H). | 2i(71%): 1H NMR(270 MHz, DMSO-d6) δ ppm: 1.46(s, 6H), 2.32(s, 3H), 2.68(t, J=6.2 Hz, 2H), 3.26(s, 3H), 3.44(t, J=6.2 Hz, 2H), 5.57(s, 2H), 7.43(t, J=8.9 Hz, 1H), 7.51(s, 1H), 7.64(s, 1H), 7.82(m, 1H), 8.21(dd, J=6.8, 2.7 Hz, 1H), 8.39(s, 1H), 9.65(s, 1H). | 4i·HCl(56%): 1H NMR(300 MHz, DMSO-d6) δ ppm: 1.66(s, 1H), 2.79(S, 3H), 3.00-3.20(m, 1H), 3.31(s, 3H), 3.50-3.70(m, 1H), 3.70-3.95(m, 2H), 4.00(s, 1H), 11.11(br s, 1H). |
| 10 | MeN-piperazinyl | 1j(50%): 1H NMR(270 MHz, DMSO-d6) δ ppm: 1.43(s, 6H), 1.74(m, 2H), 2.22(s, 3H), 2.50(m, 4H), 2.83(m, 4H), 5.85(dd, J=10.0, 1.9 Hz, 1H), 6.33(dd, J=17.0, 1.9 Hz, 1H), 6.56(dd, J=17.0, 10.0 Hz, 1H), 7.46(t, J=9.2 Hz, 1H), 7.82(br s, 2H), 8.18(br d,J=6.8 Hz, 1H), 8.63(s, 1H), 8.67(s, 1H), 9.88(s, 1H), 9.99(s, 1H). | 2j(66%): 1H NMR(270 MHz, DMSO-d6) δ ppm: 1.43(s, 6H), 1.77(m, 2H), 2.24(s, 3H), 2.50(m, 4H), 2.85(m, 4H), 5.55(s, 2H), 7.43(t, J=8.9 Hz, 1H), 7.51(s, 1H), 7.62(s, 1H), 7.82(m, 1H), 8.21(dd, J=7.0, 2.4 Hz, 1H), 8.39(s, 1H), 9.65(s, 1H). | 4j·xHCl(71%: X=2ビτ): 1H NMR(300 MHz, DMSO-d6) δ ppm: 1.69(s, 6H), 2.32(br s, 2H), 2.79(s, 3H), 3.50-4.00(m, 8H), 4.01(s, 1H). |
| 11 | HO-piperidinyl | 1k(36%): 1H NMR(270 MHz, DMSO-d6) δ ppm: 1.37(m, 2H), 1.42(s, 6H), 1.72(m, 2H), 2.23(m, 2H), 2.94(m, 2H), 3.48(m, 1H), 4.54(d, J=4.3 Hz, 1H), 5.85(d, J=10.3 Hz, 1H), 6.31(d, J=17.3 Hz, 1H), 6.54(dd, J=17.3, 10.3 Hz,1H), 7.44(t, J=9.2 Hz, 1H), 7.82(br s, 2H), 8.17(br d, J=6.8 Hz, 1H), 8.61(s, 1H), 8.65(s, 1H), 9.87(s, 1H), 9.98(s, 1H). | 2k(63%): 1H NMR(270 MHz, DMSO-d6) δ ppm: 1.39(m, 2H), 1.47(s, 6H), 1.75(m, 2H), 2.30(m, 2H), 2.98(m, 2H), 3.48(m, 1H), 4.55(m, 1H), 5.53(s, 2H), 7.42(t, J=9.2 Hz, 1H), 7.51(s, 1H), 7.63(s, 1H), 7.82(m, 1H), 8.20(dd, J=6.8, 2.7 Hz, 1H), 8.39(s, 1H), 9.63(s, 1H). | 4k(54%): 1H NMR(300 MHz, CDCl3) δ ppm: 1.41(s, 6H), 1.52-1.63(m, 3H), 1.90-2.02(m, 2H), 2.29(s, 1H), 2.35(m, 2H), 2.95(m, 2H), 3.70(m, 1H). |
| 12 | O=piperidinyl | 1l(50%): 1H NMR(300 MHz, DMSO-d6) δ ppm: 1.52(s, 6H), 2.37(t, J=6.0 Hz, 4H), 2.92(t, J=6.0 Hz, 4H), 5.83(d, J=10.1 Hz, 1H), 6.31(d, J=17.1 Hz, 1H), 6.51(dd, J=10.1, 17.1 Hz, 1H), 7.45(t, J=9.1 Hz, 1H), 7.83(m, 1H), 7.87(s, 1H), 8.18(dd, J=2.3,6.8 Hz, 1H), 8.63(s, 2H), 9.98(s, 1H), 10.00(s, 1H). | 2l(98%): 1H NMR(300 MHz, DMSO-d6) δ ppm: 1.57(s, 6H), 2.41(t, J=5.8 Hz, 4H), 2.95(t, J=5.8 Hz, 4H), 5.55(br s, 2H), 7.42(t, J=9.1 Hz, 1H), 7.66(s, 1H), 7.80(m, 1H), 8.19(dd, J=2.6, 6.9 Hz, 1H), 8.31(s, 1H), 8.31(s, 1H), 8.38(s, 1H), 9.64(s, 1H). | 4l(56%): 1H NMR(300 MHz, CDCl3) δ ppm: 1.47(s, 6H), 2.32(s, 1H), 2.48(t, J=6.1 Hz, 4H), 2.93(t, J=6.1 Hz, 4H). |

TABLE 10-continued

| Ex. | R³ | Compound 1 (yield) | Compound 2 (yield) | Compound 4, R3—H |
|---|---|---|---|---|
| 13 | Me-SO2-piperazinyl-C(Me)2-C≡C- | 1m(52%):<br>1H NMR(270 MHz, DMSO-d6) δ ppm:<br>1.44(s, 6H), 2.71(br s, 4H), 2.86(s, 3H), 3.12(br s, 4H),<br>5.85(dd, J=10.3, 1.9 Hz, 1H),<br>6.31(dd, J=17.3, 1.9 Hz, 1H),<br>6.54(dd, J=17.3, 10.3 Hz, 1H),<br>7.44(t, J=9.2 Hz, 1H),<br>7.82(br s, 2H),<br>8.17(br d, J=6.8Hz, 1H),<br>8.61(s, 1H), 8.65(s, 1H),<br>9.87(s, 1H), 9.98(s, 1H). | 2m(51%):<br>1H NMR(270 MHz, DMSO-d6) δ ppm:<br>1.50(s, 6H), 2.76(br s, 4H),<br>2.89(s, 3H), 3.16(br s, 4H),<br>5.55(s, 2H),<br>7.42(t, J=9.2 Hz, 1H),<br>7.51(s, 1H), 7.66(s, 1H),<br>7.82(m, 1H),<br>8.20(dd, J=6.8, 2.7 Hz, 1H),<br>8.39(s, 1H), 9.64(s, 1H). | 4m(85%):<br>1H NMR(300 MHz, CDCl3) δ ppm:<br>1.43(s, 6H), 2.31(s, 1H),<br>2.79(s, 3H), 2.80(br s, 4H),<br>3.29(br s, 4H). |
| 14 | MeN-piperazinyl-C(Et)2-C≡C- | 1n(45%):<br>1H NMR(270 MHz, DMSO-d6) δ ppm:<br>0.89(t, J=7.2 Hz, 6H),<br>1.60-1.80(m, 4H),<br>2.13(s, 3H), 2.32(br s, 4H),<br>2.60(br s, 4H),<br>5.82(d, J=10.0 Hz, 1H),<br>6.30(d, J=17.0 Hz, 1H),<br>6.52(dd, J=17.0, 10.0 Hz, 1H),<br>7.44(t, J=9.2 Hz, 1H),<br>7.82(br s,2H),<br>8.17(br d, J=6.8 Hz, 1H),<br>8.62(s, 1H), 8.63(s, 1H),<br>9.88(s, 1H), 9.98(s, 1H). | 2n(77%):<br>1H NMR(270 MHz, DMSO-d6) δ ppm:<br>0.92(t, J=7.3 Hz, 6H),<br>1.65-1.97(m, 4H),<br>2.15(s, 3H), 2.37(br s, 4H),<br>2.62(br s, 4H), 5.47(s, 2H),<br>7.41(t, J=9.2 Hz, 1H),<br>7.52(s, 1H), 7.63(s, 1H),<br>7.80(m, 1H),<br>8.19(dd, J=6.9, 2.4 Hz, 1H),<br>8.38(s, 1H), 9.63(s, 1H). | 4n(32%):<br>1H NMR(300 MHz, CDCl3) δ ppm:<br>0.83(t, J=7.3 Hz, 6H),<br>1.43-1.70(m, 4H),<br>2.12(s, 3H), 2.17-2.37(m, 4H), 2.40-2.59(m, 4H),<br>3.13(d, J=1.7 Hz, 1H). |
| 15 | MeO-piperidinyl-C(Me)2-C≡C- | 1o(44%):<br>1H NMR(270 MHz, DMSO-d6) δ ppm:<br>1.42(br s, 8H), 1.86(m, 2H),<br>2.27(t, J=10.6 Hz, 2H),<br>2.93(m, 2H), 3.11(m, 1H),<br>3.20(s, 3H),<br>5.84(dd, J=10.0, 1.9 Hz, 1H),<br>6.32(dd, J=17.0, 1.9 Hz, 1H),<br>6.55(dd, J=17.0, 10.0 Hz, 1H),<br>7.44(t, J=9.2 Hz,1H),<br>7.82(br s, 2H),<br>8.17(br d, J=7.0 Hz, 1H),<br>8.61(s, 1H), 8.65(s, 1H),<br>9.90(s, 1H), 9.98(s, 1H). | 2o(62%):<br>1H NMR(270 MHz, DMSO-d6) δ ppm:<br>1.46(br s, 8H), 1.86(m, 2H),<br>2.33(t, J=10.0 Hz, 2H),<br>2.92(m, 2H), 3.17(m, 1H),<br>3.22(s, 3H), 5.53(s, 2H),<br>7.41(t, J=9.2 Hz, 1H),<br>7.49(s, 1H), 7.62(s, 1H),<br>7.80(m, 1H),<br>8.19(dd, J=6.8, 2.7 Hz, 1H),<br>8.37(s, 1H), 9.62(s, 1H). | 4o(51%):<br>1H NMR(300 MHz, DMSO-d6) δ ppm:<br>1.29(s, 6H), 1.25-1.55(m, 2H), 1.75-1.90(m, 2H), 2.20(m, 2H),<br>2.81(m, 2H), 3.12(m, 1H),<br>3.21(m, 3H), 3.33(s, 1H). |
| 16 | AcN-piperazinyl-C(Me)2-C≡C- | 1p(38%):<br>1H NMR(270 MHz, DMSO-d6) δ ppm:<br>1.44(s, 6H), 1.97(s, 3H),<br>2.55(br s, 2H), 2.61(br s, 2H),<br>3.42(br s, 4H),<br>5.82(dd, J=10.0, 1.9 Hz, 1H),<br>6.30(dd, J=17.0, 1.9 Hz, 1H),<br>6.51(dd, J=17.0, 10.0 Hz, 1H),<br>7.44(t, J=9.2 Hz,1H),<br>7.83(br s, 2H),<br>8.16(br d, J=6.8 Hz, 1H),<br>8.61(s, 1H), 8.63(s, 1H),<br>9.91(s, 1H), 9.98(s, 1H). | 2p(66%):<br>1H NMR(270 MHz, DMSO-d6) δ ppm:<br>1.49(s, 6H), 1.98(s, 3H),<br>2.58(br s, 2H), 2.64(br s, 2H),<br>3.46(br s, 4H), 5.53(s, 2H),<br>7.41(t, J=9.2 Hz, 1H),<br>7.49(s, 1H), 7.63(s, 1H),<br>7.80(m, 1H),<br>8.19(dd, J=6.8, 2.7 Hz, 1H),<br>8.37(s, 1H), 9.63(s, 1H). | 4p(49%):<br>1H NMR(300 MHz, DMSO-d6) δ ppm:<br>1.32(s, 6H), 1.99(s, 3H),<br>2.41-2.59(m, 4H),<br>3.18(s, 1H),<br>3.43(br t, J=4.4 Hz, 4H). |

TABLE 10-continued

| Ex. | R³ | Compound 1 (yield) | Compound 2 (yield) | Compound 4, R3—H |
|---|---|---|---|---|
| 17 | 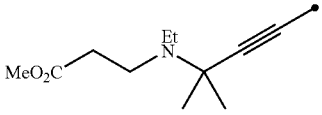 | 1q(64%):<br>1H NMR(270 MHz, DMSO-d6) δ ppm:<br>1.02(t, J=7.2 Hz, 3H),<br>1.43(s, 6H), 2.50(br s, 2H),<br>2.69(q, J=7.2 Hz, 2H),<br>2.92(t, J=7.2 Hz, 2H),<br>3.59(s, 3H),<br>5.84(d, J=10.0 Hz, 1H),<br>6.32(d, J=17.0 Hz, 1H),<br>6.55(dd, J=17.0, 10.0 Hz,1H),<br>7.46(t, J=9.2 Hz, 1H),<br>7.83(br s, 2H),<br>8.19(br d, J=6.8 Hz, 1H),<br>8.63(s, 1H), 8.67(s, 1H),<br>9.90(s, 1H), 9.99(s, 1H). | 2q(43%):<br>1H NMR(270 MHz, DMSO-d6) δ ppm:<br>1.05(t, J=7.0 Hz, 3H),<br>1.46(s, 6H), 2.49(br s, 2H),<br>2.71(q, J=7.0 Hz, 2H),<br>2.94(t, J=7.3 Hz, 2H),<br>3.58(s, 3H), 5.53(s, 2H),<br>7.41(t, J=9.2 Hz, 1H),<br>7.48(s, 1H), 7.61(s, 1H),<br>7.80(m, 1H),<br>8.19(dd, J=6.8, 2.4 Hz, 1H),<br>8.37(s, 1H), 9.62(s, 1H). | 4q(50%):<br>1H NMR(300 MHz, CDCl3) δ ppm:<br>1.08(t, J=7.2 Hz, 3H),<br>1.39(s, 6H), 2.23(s, 1H),<br>2.53(t, J=7.7 Hz, 2H),<br>2.67(q, J=7.2 Hz, 2H),<br>2.94(t, J=7.7 Hz, 2H),<br>3.67(s, 3H). |
| 18 | 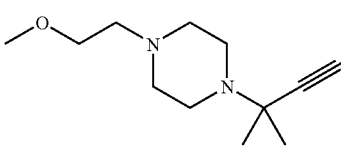 | 1r(38%):<br>1H NMR(270 MHz, DMSO-d6) δ ppm:<br>1.42(s, 6H),<br>2.43(brt, J=6.0 Hz, 6H),<br>2.62(br s, 4H), 3.22(s, 3H),<br>3.41(t, J=6.0 Hz, 2H),<br>5.84(d, J=10.3 Hz, 1H),<br>6.33(d, J=16.7 Hz, 1H),<br>6.57(dd, J=16.7, 10.3 Hz, 1H),<br>7.46(t, J=9.2 Hz, 1H),<br>7.84(br s, 2H),<br>8.19(br d,J=6.8 Hz, 1H),<br>8.63(s, 1H), 8.68(s, 1H),<br>9.87(s, 1H), 10.00(s, 1H). | 2r(53%):<br>1H NMR(270 MHz, DMSO-d6) δ ppm:<br>1.45(s, 6H),<br>2.43(t, J=6.0 Hz, 2H),<br>2.49(br s, 4H), 2.63(br s, 4H),<br>3.21(s, 3H),<br>3.41(t, J=6.0 Hz, 2H),<br>5.53(s, 2H),<br>7.41(t, J=9.2 Hz, 1H),<br>7.50(s, 1H), 7.62(s, 1H),<br>7.80(m, 1H),<br>8.19(dd, J=7.0, 2.7 Hz, 1H),<br>8.37(s, 1H), 9.63(s, 1H). | 4r: 1H NMR(300 MHz, CDCl3) δ ppm:<br>1.40(s, 6H), 2.27(s, 1H),<br>2.59(m, 6H), 2.72(br s, 4H),<br>3.35(s, 3H), 3.53(m, 2H). |
| 19 | 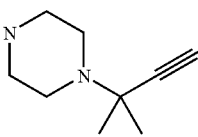 | 1s(48%):<br>1H NMR(270 MHz, DMSO-d6) δ ppm:<br>1.43(s, 6H), 2.46-2.57(m, 6H), 2.62-2.68(m, 6H),<br>5.86(dd, J=10.0, 1.9 Hz, 1H),<br>6.33(dd, J=16.7, 1.9 Hz, 1H),<br>6.57(dd, J=16.7, 10.0 Hz, 1H),<br>7.46(t, J=9.2 Hz, 1H),<br>7.84(br s, 2H),<br>8.19(br d, J=7.0 Hz, 1H),<br>8.63(s, 1H),8.67(s, 1H),<br>9.88(s, 1H), 10.00(s, 1H). | 2s(72%):<br>1H NMR(270 MHz, DMSO-d6) δ ppm:<br>1.46(s, 6H), 2.40-2.58(m, 6H), 2.60-2.75(m, 6H), 5.53(s, 2H),<br>7.41(t, J=9.2 Hz, 1H),<br>7.49(s, 1H), 7.62(s, 1H),<br>7.80(m, 1H),<br>8.19(dd, J=7.0, 2.7 Hz, 1H),<br>8.37(s, 1H), 9.63(s, 1H). | 4s: 1H NMR(300 MHz, CDCl3) δ ppm:<br>1.40(s, 6H), 2.30(s, 1H),<br>2.52(t, 2H), 2.45-2.65(m, 4H), 2.65-2.85(m, 6H). |
| 20 | 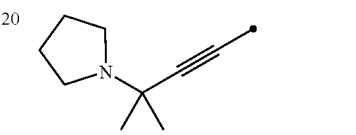 | 1t(46%):<br>1H NMR(270 MHz, DMSO-d6) δ ppm:<br>1.44(s, 6H), 1.68(br s, 4H),<br>2.68(br s, 4H),<br>5.85(dd, J=10.0, 1.9 Hz, 1H),<br>6.32(dd, J=17.0, 1.9 Hz, 1H),<br>6.54(dd, J=17.0, 10.0 Hz, 1H),<br>7.46(t, J=9.2 Hz, 1H),<br>7.84(br s, 2H),<br>8.19(br d, J=6.8 Hz,1H),<br>8.63(s, 1H), 8.65(s, 1H),<br>9.91(s, 1H), 9.99(s, 1H). | 2t(75%):<br>1H NMR(270 MHz, DMSO-d6) δ ppm:<br>1.47(s, 6H), 1.72(br s, 4H),<br>2.71(br s, 4H), 5.51(s, 2H),<br>7.41(t, J=9.2 Hz, 1H),<br>7.49(s, 1H), 7.62(s, 1H),<br>7.81(m, 1H),<br>8.19(dd, J=7.0, 2.7 Hz, 1H),<br>8.37(s, 1H), 9.62(s, 1H). | 4t(52%):<br>1H NMR(300 MHz, CDCl3) δ ppm:<br>1.42(s, 6H), 1.80(m, 4H),<br>2.24(s, 1H), 2.72(m, 4H). |

TABLE 10-continued

| Ex. | R³ | Compound 1 (yield) | Compound 2 (yield) | Compound 4, R3—H |
|---|---|---|---|---|
| 21 | 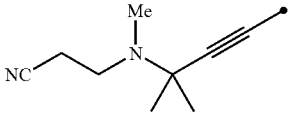 | 1u(33%):<br>¹H NMR(270 MHz, DMSO-d6) δ ppm: 1.45(s, 6H), 2.30(s, 3H), 2.65(t, J=5.8 Hz, 2H), 2.74(t, J=5.8 Hz, 2H), 5.85(d, J=10.0 Hz, 1H), 6.33(d, J=17.0 Hz, 1H), 6.56(dd, J=17.0, 10.0 Hz, 1H), 7.46(t, J=9.2 Hz, 1H), 7.87(br s,2H), 8.19(br d, J=6.8 Hz, 1H), 8.63(s, 1H), 8.66(s, 1H), 9.93(s, 1H), 10.00(s, 1H). | 2u(quant):<br>1H NMR(270 MHz, DMSO-d6) δ ppm: 1.49(s, 6H), 2.34(s, 3H), 2.65-2.80(m, 4H), 5.56(s, 2H), 7.43(t, J=9.2 Hz, 1H), 7.50(s, 1H), 7.66(s, 1H), 7.81(m, 1H), 8.20(dd, J=7.0, 2.4 Hz, 1H), 8.39(s, 1H), 9.64(s, 1H). | 4u·HCl(81%):<br>1H NMR(300 MHz, DMSO) δ ppm: 1.64(s, 6H), 2.75(s, 3H), 3.17(brt, J=6.8 Hz, 2H), 3.30-3.70(m, 2H), 3.98(s, 1H);<br>4u: 1H NMR(300 MHz, CDCl3) δ ppm: 1.38(s, 6H), 2.27(s, 1H), 2.30(s, 3H), 2.48(t, J=6.9 Hz, 2H), 2.78(t, J=6.9 Hz, 2H). |
| 22 | 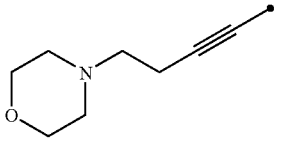 | 1v(72%):<br>¹H NMR(300 MHz, DMSO-d6) δ ppm: 2.20-2.50(m, 4H), 2.50-2.64(m, 2H), 2.64-2.75(m, 2H), 3.40-3.60(m, 4H), 5.83(dd, J=1.3, 10.2 Hz, 1H), 6.32(dd, J=1.3, 10.2 Hz, 1H), 6.62(dd, J=10.2, 17.1 Hz, 1H), 7.42(t,J=9.1 Hz, 1H), 7.70-7.82(m, 1H), 7.80(s, 1H), 8.11(dd, J=2.3, 6.8 Hz, 1H), 8.56(s, 1H), 8.74(s, 1H), 9.89(s, 1H), 9.98(s, 1H). | 2v(59%):<br>1H NMR(300 MHz, DMSO-d6) δ ppm: 2.15-2.50(m, 4H), 2.50-2.65(m, 2H), 2.65-2.80(m, 2H), 3.50-3.75(m, 4H), 5.91(s, 2H), 7.42(t, J=8.9 Hz, 1H), 7.44(s, 1H), 7.59(s, 1H), 7.80(m, 1H), 8.18(dd, J=2.4,6.7 Hz, 1H), 8.36(s, 1H), 9.61(s, 1H). | 4v·HCl(74%):<br>1H NMR(300 MHz, DMSO-d) δ ppm: 2.78(dt, J=2.4, 7.7 Hz, 2H), 3.00-3.20(m, 2H), 3.10(t, J=2.4 Hz, 1H), 3.20-3.35(m, 2H), 3.35-3.50(m, 2H), 3.70-3.88(m, 2H), 3.90-4.00(m, 2H), 11.47(br s, 1H). |
| 23 | 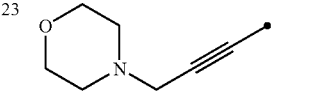 | 1x(59%):<br>1H NMR(300 MHz, DMSO-d6) δ ppm: 2.45-2.65(m, 4H), 3.50-3.70(m, 6H), 5.84(dd, J=1.4, 10.3 Hz, 1H), 6.33(dd, J=1.4, 17.0 Hz, 1H), 6.60(dd, J=10.3, 17.0 Hz, 1H), 7.46(t, J=9.1 Hz, 1H), 7.82(m, 1H),7.89(s, 1H), 8.18(dd, J=2.3, 6.7 Hz, 1H), 8.62(s, 1H), 8.72(s, 1H), 10.01(s, 1H), 10.02(s, 1H). | 2x(59%):<br>1H NMR(300 MHz, DMSO-d6) δ ppm: 2.50-2.70(m, 4H), 3.45-3.75(m, 6H), 5.68(br s, 2H), 7.43(t, J=9.1Hz, 1H), 7.49(s, 1H), 7.67(s, 1H), 7.76-7.86(m, 1H), 8.20(dd, J=2.2, 6.7 Hz, 1H), 8.38(s, 1H), 9.64(s, 1H). | 4x(98%):<br>1H NMR(300 MHz, CDCl₃) δ ppm: 2.28(t, J=2.2 Hz, 1H), 2.57(t, J=4.6 Hz, 4H), 3.30(d, J=2.2 Hz, 2H), 3.75(t, J=4.6 Hz, 4H). |
| 24 | 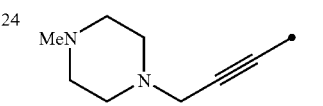 | 1y(39%):<br>1H NMR(300 MHz, DMSO-d6) δ ppm: 2.16(s, 3H), 2.34(br s, 4H), 2.56(br s, 4H), 3.60(s, 2H), 5.84(d, J=10.1 Hz, 1H), 6.33(d, J=16.9 Hz, 1H), 6.61(dd, J=16.9 Hz, 10.1 Hz, 1H), 7.46(t, J=9.0 Hz, 1H), 7.76-7.90(m, 1H), 7.87(s, 1H),8.17(m, 1H), 8.62,(s, 1H), 8.73(s, 1H), 9.98(s, 1H), 10.01(s, 1H). | 2y(93%):<br>1H NMR(300 MHz, DMSO-d6) δ ppm: 2.17(s, 3H), 2.10-2.40(m, 4H), 2.40-2.75(m, 4H), 3.65(s, 2H), 5.68(br s, 2H), 7.42(t, J=9.1Hz), 7.48(s, 1H), 7.66(s, 1H), 7.73-7.85(m, 1H), 8.18(dd, J=1.9, 6.6 Hz, 1H), 8.37(s, 1H), 9.64(s, 1H). | 4y(63%):<br>1H NMR(300 MHz, CDCl₃) δ ppm: 2.25(t, J=2.3 Hz, 1H), 2.30(s, 3H), 2.30-2.85(m, 8H), 3.30(d, J=2.3 Hz, 2H). |

TABLE 10-continued

| Ex. | R³ | Compound 1 (yield) | Compound 2 (yield) | Compound 4, R3—H |
|---|---|---|---|---|
| 25 | 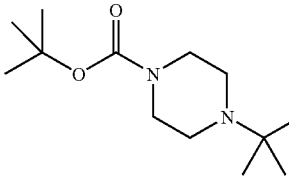 | 1z(58%):<br>1H NMR(270 MHz,<br>DMSO-d6) δ ppm:<br>1.38(s, 9H), 1.43(s, 6H),<br>2.49(br s, 4H), 2.56(br s, 4H),<br>5.82(dd, J=10.0, 1.9 Hz, 1H),<br>6.31(dd, J=16.7, 1.9 Hz, 1H),<br>6.52(dd, J=16.7,<br>10.0 Hz, 1H),<br>7.44(t, J=9.2 Hz, 1H),<br>7.83(br s, 2H),<br>8.17(br d,J=7.0 Hz, 1H),<br>8.61(s, 1H), 8.63(s, 1H),<br>9.92(s, 1H), 9.98(s, 1H). | 2z(79%):<br>1H NMR(270 MHz,<br>DMSO-d6) δ ppm:<br>1.39(s, 9H), 1.49(s, 6H),<br>2.51(br s, 4H), 2.60(br s, 4H),<br>5.53(s, 2H),<br>7.42(t, J=9.2 Hz, 1H),<br>7.50(s, 1H), 7.64(s, 1H),<br>7.81(m, 1H),<br>8.20(dd, J=6.8, 2.4 Hz, 1H),<br>8.39(s, 1H), 9.63(s, 1H). | 4z(49%):<br>1H NMR(300 MHz,<br>CDCl₃) δ ppm:<br>1.39(s, 6H), 1.46(s, 9H),<br>2.29(s, 1H),<br>2.58(t, J=5.1 Hz, 4H),<br>3.45(t, J=5.1 Hz, 4H). |

Synthetic Examples 7-12

Synthesis of acetylene 4

In the above-mentioned Examples 3-25, acetylene compound 4 used as the starting material was synthesized according to the method of Synthetic Example 1, except when shown in the following Synthetic Example. In some cases, the compound was converted to the corresponding hydrochloride (4N hydrochloric acid-ethyl acetate) and used. The yield and ¹H NMR spectrum data are shown in the Table.

Synthetic Example 7

4g: A solution (360 mL, 180 mmol) of ethynyl magnesium chloride in 0.5 M THF was stirred under ice-cooling and 1,3-diethoxyacetone (21.93 g, 150 mmol) was added dropwise. The mixture was stirred under ice-cooling for 30 min and acetic anhydride (18.4 mL, 195 mmol) was added dropwise. The mixture was stirred at room temperature for 1 hr. After the completion of the reaction, aqueous ammonium chloride solution was added, and the mixture was extracted with ethyl acetate. The organic layer was washed with saturated aqueous sodium hydrogen carbonate and saturated brine, dried over anhydrous magnesium sulfate and concentrated to give acetic acid 1,1-bis-ethoxymethyl-2-propynyl ester (31.36 g, 97%).

Acetic acid 1,1-bis(ethoxymethyl)-2-propynyl ester (15.00 g, 70 mmol), 1-methylpiperazine (8.41 g, 84 mmol), copper chloride (I) (350 mg) and triethylamine (9.7 mL, 70 mmol) were dissolved in THF (150 mL) and the mixture was heated under reflux for 2 hrs. After the completion of the reaction, ᵗBuOMe was added to the reaction mixture and the mixture was extracted with 3N hydrochloric acid. The extract was neutralized with 6N aqueous sodium hydroxide solution and extracted with ethyl acetate. The organic layer was washed with 7% aqueous ammonium chloride solution and water, dried over anhydrous magnesium sulfate and concentrated to give the title compound 4 g (15.30 g, 86%).

Synthetic Example 8

4o: 1-(1,1-Dimethyl-2-propynyl)piperidin-4-ol 4k [synthesized according to the method of Synthetic Example 1 using 4-hydroxypiperidine as a starting material; yield 54%] (6.0 g, 36.0 mmol) was dissolved in THF (100 mL) and NaH (1.73 g) and methyl iodide (7.7 g) were added. The mixture was stirred for one day at room temperature. The reaction mixture was concentrated and water was added, and the mixture was extracted with dichloromethane. The organic layer was dried over magnesium sulfate. The organic layer was concentrated and the residue was dissolved in ethyl acetate. 4N Hydrochloric acid-ethyl acetate (9 mL) was added dropwise under ice-cooling, and the produced precipitate was collected by filtration and dried to give 4o.HCl (4.0 g, 51%).

Synthetic Example 9

4m: A solution (60 mL) of 4-(1,1-dimethyl-2-propynyl)piperazine [synthesized according to the method of Synthetic Example 1 using an excess of piperazine (2.5 equivalent amount) as a starting material; yield 42%] (6.0 g, 40.0 mmol) and pyridine (3.50 mL) in dichloromethane was stirred under ice-cooling and methanesulfonyl chloride (5.6 g) was added. The mixture was gradually warmed to room temperature and water was added. The mixture was extracted with dichloromethane. The extract was washed with aqueous sulfuric acid copper solution, water and saturated brine and dried over magnesium sulfate. The organic layer was concentrated to give compound 4 m (7.80 g, 85%) as a pale-yellow solid.

Synthetic Example 10

4r: 1-(1,1-Dimethyl-2-propynyl)piperazine (5.0 g, 33 mmol), 2-chloroethyl methyl ether (4.7 g, 50 mmol), sodium iodide (35.0 g, 233 mmol) and potassium carbonate (9.2 g, 66 mmol) were suspended in methyl ethyl ketone (150 mL) and the reaction mixture was heated under reflux for three days. The solvent was evaporated under reduced pressure and ethyl acetate was added to the residue. The mixture was extracted with 3N hydrochloric acid. The extract was neutralized with 6N aqueous sodium hydroxide solution and extracted with dichloromethane. The organic layer was washed with water and dried over anhydrous magnesium sulfate. The solvent was evaporated under reduced pressure and the residue was dissolved in ethyl acetate. 4N Hydrochloric acid-ethyl acetate (17.0 mL) was added, and the precipitated crystals were collected by filtration and dried in vacuo to give compound 4r (7.44 g, 79%) as pale-yellow crystals.

Synthetic Example 11

4s: 1-(1,1-Dimethyl-2-propynyl)piperazine (5.0 g, 33 mmol) and acrylonitrile (2.6 g, 49 mmol) were dissolved in methanol (50 mL) and the mixture was stirred at room temperature for 3 hrs and at 55° C. for 4 hrs. The reaction mixture was concentrated and dried in vacuo to give compound 4s (6.51 g, 96%) as yellowish white crystals.

Synthetic Example 12

4v: A suspension (40 mL) of toluene-4-sulfonic acid 3-butynyl ester (4.0 g, 17.8 mmol), morpholine (2.94 mL, 26.7 mmol) and potassium carbonate (2.96 g, 21.4 mmol) in acetonitrile was refluxed for 2.5 hrs. After allowing to cool, the mixture was filtered and the residue was washed with $^t$BuOMe (20 mL). The filtrate was concentrated and $^t$BuOMe (40 mL) was added. The product was extracted with 3N hydrochloric acid (30 mL×1, 10 mL×1). 6N Aqueous sodium hydroxide solution was added to the extract until it showed basicity. The mixture was extracted with dichloromethane (40 mL×1, 20 mL×1). The organic layer was dried and concentrated to give compound 4v (2.44 g, 98%) as an oil. This oil 4v (3.94 g, 28.2 mmol) was dissolved in diethyl ether (20 mL) and 4N hydrochloric acid-ethyl acetate (7.8 mL, 31.2 mmol) was added dropwise with stirring on an ice bath. After stirring at room temperature for 30 min, the precipitate was collected by filtration. The residue was washed with diethyl ether and dried under reduced pressure to give compound 4v.HCl (3.78 g, 76%) as a white solid.

Example 26

1) To a solution (30 mL) of triethylamine (5.5 mL, 40 mmol) in ethanol were added dimethylamine hydrochloride (3.26 g, 40 mmol), titan tetraisopropoxide (11.8 mL, 40 mmol) and 1-(1,1-dimethyl-2-propynyl)piperidin-4-one (41) (3.3 g, 20 mmol) at room temperature. After stirring for 7 hrs, NaBH$_4$ (1.13 g, 30 mmol) was added and the mixture was stirred overnight at room temperature. The reaction mixture was poured into 5% aqueous ammonia (80 mL) and dichloromethane (100 mL) was added. The mixture was filtered through Celite and the filtration residue was washed with dichloromethane (30 mL×3). The organic layer was partitioned, dried and filtered through silica gel column (20 g). The filtrate was concentrated, and the obtained solid was subjected to sublimation (oil bath temperature about 100° C./0.1 mmHg) under reduced pressure to give [1-(1,1-dimethyl-2-propynyl)-4-piperidinyl]dimethylamine (4aa) as colorless crystals.

2) A solution of 7-bromo-N$^4$-(3-chloro-4-fluorophenyl)-4,6-quinazolinediamine (5) (557 mg, 1.52 mmol), compound 4aa (383 mg, 1.97 mmol) and triethylamine (12 mL) in DMF (2.4 mL) was subjected 3 times to the step of degassing under reduced pressure and displacement with nitrogen. Triphenylphosphine (24 mg, 0.09 mmol) and palladium (II) acetate (10 mg, 0.05 mmol) were added. The mixture was stirred at 80° C. for 3 hrs and allowed to cool to room temperature. The solvent was evaporated under reduced pressure and aqueous sodium hydrogen carbonate was added to the residue. The mixture was extracted with ethyl acetate, and the organic layer was washed successively with water (×3) and saturated brine, and dried over anhydrous sodium sulfate. The solvent was evaporated under reduced pressure to give an amino compound 2aa.

3) A solution of the amino compound 2aa (690 mg, 1.43 mmol), acrylic acid (0.49 mL, 7.2 mmol), triethylamine (0.30 mL, 2.15 mmol) and EDC (410 mg, 2.15 mmol) in DMF (8 mL).was stirred overnight at room temperature. The reaction mixture was evaporated under reduced pressure and the residue was extracted with ethyl acetate. The organic layer was washed successively with water (×3) and saturated brine and dried over anhydrous sodium sulfate, and the solvent was evaporated under reduced pressure. The purified crude substance was subjected to silica gel column chromatography (chloroform-methanol-triethylamine) and the obtained purified crude substance was recrystallized from water-ethanol to give the objective compound 1aa (127 mg, 16%).

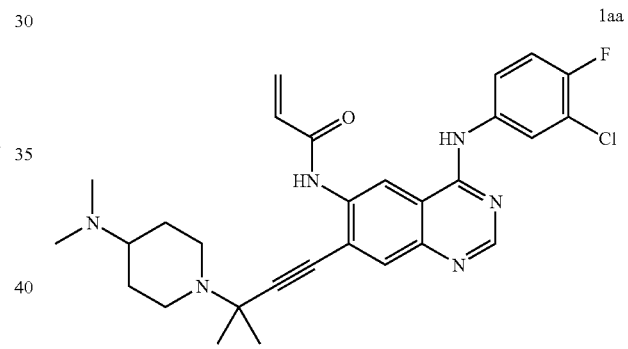

1aa

1aa: $^1$H NMR (270 MHz, DMSO-d$_6$) δ ppm: 1.32 (br d, 2H), 1.44 (s, 6H), 1.76 (br d, J=11.2 Hz, 2H), 1.99 (m, 1H), 2.15 (br s, 8H), 3.10 (br d, J=11.3 Hz, 2H), 5.84 (d, J=10.1 Hz, 1H), 6.33 (d, J=17.0 Hz, 1H), 6.56 (dd, J=17.0, 10.1 Hz, 1H), 7.46 (t, J=9.2 Hz, 1H), 7.84 (br s, 2H), 8.19 (br d, J=7.2 Hz, 1H), 8.63 (s, 1H), 8.66 (s, 1H), 9.91 (s, 1H), 9.99 (s, 1H).

Example 27

1) A solution (9 mL) of (7-bromo-6-nitro-4-quinazolinyl)-(3-chloro-4-fluorophenyl)amine (3.0 g, 7.55 mmol) obtained by a treatment, with triethylamine in water-methanol, of (7-bromo-6-nitro-4-quinazolinyl)-(3-chloro-4-fluorophenyl)amine hydrochloride produced according to the method described in Synthetic Example 4, acetylene 4ab (1.76 g, 9.06 mmol) synthesized according to the method of Synthetic Example 1 and triethylamine (60 mL) in DMF solution was subjected 3 times to the step of degassing under reduced pressure and displacement with nitrogen. Triphenylphosphine (118 mg, 0.46 mmol) and palladium (II) acetate (51 mg, 0.23 mmol) were added. The mixture was stirred at 80° C. for 3 hrs and allowed to cool to room temperature. The solvent was evaporated under reduced pressure and aqueous sodium hydrogen carbonate was added to the residue. The mixture was extracted with ethyl acetate, and the organic layer was washed successively with water (×3) and saturated brine, and dried over anhydrous sodium sulfate. The solvent was evaporated under reduced pressure to give a nitro compound 3ab.

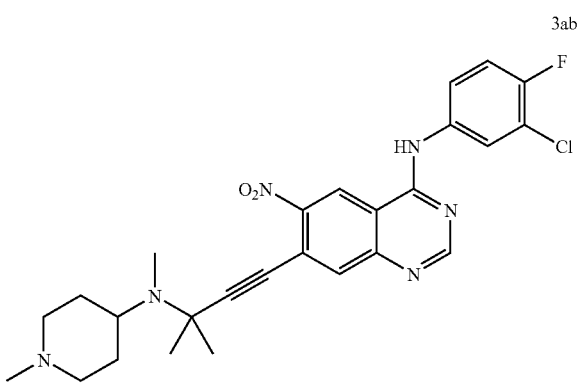

3ab

3ab: ¹H NMR (270 MHz, DMSO-d₆) δ ppm: 1.48 (s, 6H), 1.66 (m, 4H), 1.95 (m, 2H), 2.14 (s, 3H), 2.33 (s, 3H), 2.79 (br d, J=11.6 Hz, 2H), 2.97 (m, 1H), 7.48 (t, J=9.2 Hz, 1H), 7.80 (m, 1H), 7.88 (s, 1H), 8.16 (br d, J=7.0 Hz, 1H), 8.73 (s, 1H), 9.45 (s, 1H), 10.45-10.55 (br s, 1H).

4ab

4ab [synthesized according to the method of Synthetic Example 1; yield 69%]: ¹H NMR (300 MHz, DMSO-d₆) δ ppm: 1.31 (s, 6H), 1.45-1.72 (m, 4H), 1.77-1.93 (m, 2H), 2.11 (s, 3H), 2.21 (s, 3H), 2.70-2.95 (m, 3H), 3.10 (s, 1H).

2) A mixture of the nitro compound 3ab, 1N hydrochloric acid (22.5 mL, 22.5 mmol) and iron powder (2.09 g, 37.5 mmol) in ethanol (70 mL) was refluxed for 1.5 hrs. The reaction mixture was allowed to become 50° C. and 1N aqueous sodium hydroxide solution (22.5 mL, 22.5 mmol) was added. The mixture was stirred at 50° C. for 30 min. The reaction mixture was allowed to cool to room temperature and filtered through Celite. The residue was washed with ethyl acetate and the filtrate was concentrated. Aqueous sodium hydrogen carbonate was added to the residue and the mixture was extracted with ethyl acetate. The organic layer was washed successively with water (×3) and saturated brine and dried over anhydrous sodium sulfate. The solvent was evaporated under reduced pressure. The residue was suspended in acetonitrile and the mixture was stirred with heating under reflux. The mixture was allowed to reach room temperature and said residue was collected by filtration to give the objective amino compound 2ab (2.78 g, 76%).

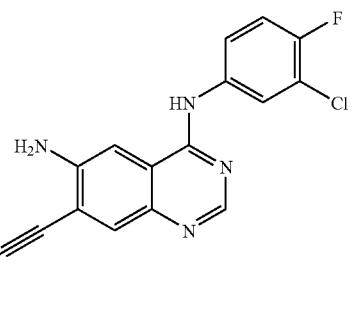

2ab

2ab: ¹H NMR (270 MHz, DMSO-d₆) δ ppm: 1.50 (s, 6H), 1.66 (m, 4H), 1.92 (m, 2H), 2.13 (s, 3H), 2.33 (s, 3H), 2.79 (br d, J=10.8 Hz, 2H), 2.99 (m, 1H), 5.53 (s, 2H), 7.42 (t, J=9.2 Hz, 1H), 7.50 (s, 1H), 7.57 (s, 1H), 7.80 (m, 1H), 8.21 (dd, J=7.0, 2.4 Hz, 1H), 8.39 (s, 1H), 9.63 (s, 1H).

3) In the same manner as in Example 26-3), the amino compound 2ab was converted to the objective compound 1ab (yield 33%).

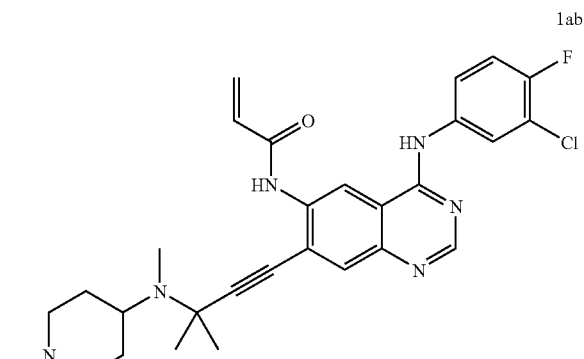

1ab

1ab: ¹H NMR (270 MHz, DMSO-d₆) δ ppm: 1.46 (s, 6H), 1.63 (m, 4H), 1.86 (m, 2H), 2.10 (s, 3H), 2.30 (s, 3H), 2.74 (br d, J=10.8 Hz, 2H), 2.92 (m, 1H), 5.85 (d, J=10.0 Hz, 1H), 6.33 (d, J=17.0 Hz, 1H), 6.56 (dd, J=17.0, 10.0 Hz, 1H), 7.46 (t, J=9.2 Hz, 1H), 7.78 (s, 1H), 7.81 (m, 1H), 8.18 (br d, J=6.6 Hz, 1H), 8.62 (s, 1H), 8.66 (s, 1H), 9.88 (s, 1H), 9.99 (s, 1H).

Example 28

Using 4ac (yield 80%) synthesized in the same manner as in Synthetic Example 12 from 1-methylpiperazine and toluene-4-sulfonic acid 3-butynyl ester, and (7-bromo-6-nitro-4-quinazolinyl)-(3-chloro-4-fluorophenyl)amine as starting materials, the converted compounds 3ac, 2ac and 1ac were obtained in the same manner as in the above-mentioned Example 27.

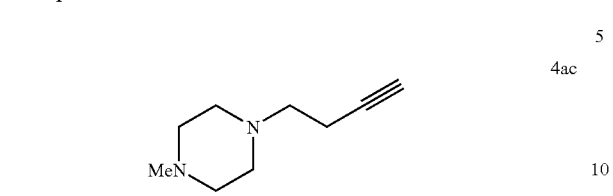
4ac

4ac: ¹H NMR (300 MHz, CDCl₃) δ ppm: 1.97 (t, J=2.6 Hz, 1H), 2.28 (s, 3H), 2.38 (dt, J=2.6, 7.7 Hz, 2H), 2.46 (br s, 4H), 2.53 (br s, 4H), 2.61 (t, J=7.7 Hz, 2H).

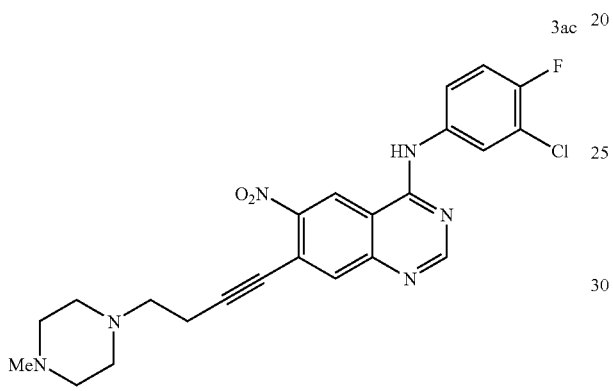
3ac

3ac: ¹H NMR (270 MHz, DMSO-d₆) δ ppm: 2.13 (s, 3H), 2.33 (br s, 4H), 2.47 (br s, 4H), 2.59-2.73 (m, 4H), 7.48 (t, J=9.2 Hz, 1H), 7.79 (m, 1H), 7.90 (s, 1H), 8.14 (dd, J=6.8,2.4 Hz, 1H), 8.72 (s, 1H), 9.38 (s, 1H), 10.42 (br s, 1H).

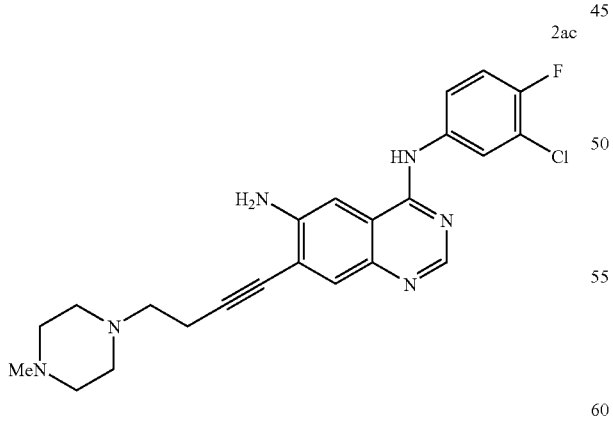
2ac

2ac: ¹H NMR (270 MHz, DMSO-d₆) δ ppm: 2.16 (s, 3H), 2.36 (br s, 4H), 2.47 (br s, 4H), 2.60 (t, J=6.5 Hz, 2H), 2.72 (t, J=6.5 Hz, 2H), 5.86 (s, 2H), 7.42 (t, J=9.2 Hz, 1H), 7.46 (s, 1H), 7.58 (s, 1H), 7.81 (m, 1H), 8.20 (dd, J=6.8, 2.7 Hz, 1H), 8.37 (s, 1H), 9.60 (s, 1H).

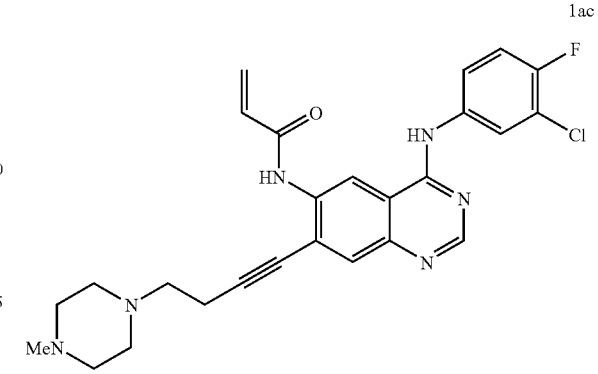
1ac

1ac: ¹H NMR (270 MHz, DMSO-d₆) δ ppm: 2.15 (s, 3H), 2.32 (br s, 4H), 2.46 (br s, 4H), 2.60-2.69 (m, 4H), 5.86 (d, J=10.0 Hz, 1H), 6.35 (d, J=17.0 Hz, 1H), 6.65 (dd, J=17.0, 10.0 Hz, 1H), 7.45 (t, J=9.2 Hz, 1H), 7.81 (br s, 2H), 8.16 (br d, J=7.0 Hz, 1H), 8.60 (s, 1H), 8.78 (s, 1H), 9.86 (s, 1H), 10.00 (s, 1H).

Example 29

A mixture of compound 2a (2.40 g, 5.3 mmol) and 10% palladium carbon (170 mg) in THF (15 mL)-ethanol (15 mL) was stirred under a hydrogen atmosphere at room temperature for 12 hrs. The reaction mixture was filtered through Celite and the filtrate was concentrated. The residue was subjected to silica gel chromatography (chloroform-methanol) to give an amino compound [m/z=455 (M+1)] (1.69 g, 70%). A solution (2 mL) of this amino compound (330 mg, 0.73 mmol), EDC (278 mg, 1.45 mmol), acrylic acid (99 µL) and triethylamine (200 µL) in DMF was stirred overnight at room temperature. Aqueous sodium hydrogen carbonate (40 mL) was added to the reaction mixture and the mixture was extracted with ethyl acetate (40 mL×1, 20 mL×1). The extract was dried and concentrated. The obtained crude purified substance was subjected to silica gel column (chloroform-methanol-triethylamine), and suspension-washed with acetonitrile to give the objective compound 1ad (200 mg, 54%).

1ad

1ad: ¹H NMR (300 MHz, DMSO-d₆) δ ppm: 0.96 (s, 6H), 1.99 (s, 3H), 2.00-2.25 (m, 4H), 2.25-2.60 (m, 4H), 5.73 (d, J=12.9 Hz, 1H), 5.81 (d, J=10.4 Hz, 1H), 6.30 (d, J=16.9 Hz, 1H), 6.48 (d, J=12.9 Hz, 1H), 6.59 (dd, J=10.4, 16.9 Hz, 1H), 7.45 (t, J=9.1 Hz, 1H), 7.80-7.92 (m, 1H), 7.90 (s, 1H), 8.20 (dd, J=2.2, 6.7 Hz, 1H), 8.61 (s, 1H), 9.80 (s, 1H), 9.92 (s, 1H).

Example 30

A mixture of compound 4ac (333 mg, 2.18 mmol), tributyltin hydride (764 mg, 2.62 mmol) and 2,2'-azobisisobutyronitrile (4 mg, 0.02 mmol) was stirred at 80° C. for 2 hrs. To this solution were added compound 5 (670 mg, 1.80 mmol), palladium (II) acetate (10 mg), triphenylphosphine (24 mg), DMF (1.3 mL) and triethylamine (7 mL), and the mixture was stirred at 80° C. for 4 hrs. To the reaction mixture was added $Pd_2(dba)_3$ (dba=dibenzylidenacetone) (15 mg) and the mixture was stirred under refluxing for 4 hrs. After allowing to stand to cool, aqueous potassium fluoride solution (50 mL) was added and the mixture was stirred at room temperature for a while. The product was extracted with ethyl acetate (50 mL×1, 20 mL×2). The organic layer was dried and concentrated. The residue was subjected to silica gel column chromatography (chloroform-methanol-triethylamine) to give an oil (1.02 g) containing the objective product. Using this oil (500 mg), EDC (345 mg, 1.8 mmol), acrylic acid (0.123 mL, 1.8 mmol), triethylamine (0.25 mL, 1.8 mmol) and DMF (4.0 mL) and in the same manner as in Example 1, the reaction was conducted. The purified crude substance was subjected to column chromatography (chloroform-methanol-triethylamine) and a small amount of acetonitrile was added to the obtained oil (180 mg) to allow crystallization. Acetonitrile (4 mL) was further added, and the mixture was stirred under reflux and cooled to room temperature. The precipitate was collected by filtration to give the objective compound 1ae (95 mg, theological yield 21%).

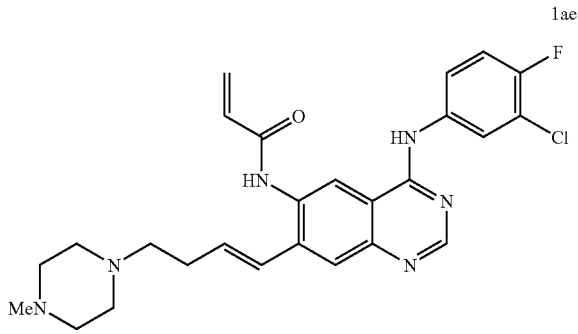

1ae

1ae: $^1$H NMR (300 MHz, DMSO-$d_6$) δ ppm: 2.14 (s, 3H), 2.10-2.50 (m, 12H), 5.82 (dd, J=1.5, 10.2 Hz, 1H), 6.29 (dd, J=1.5, 17.1 Hz, 1H), 6.52 (dt, J=6.0, 15.8 Hz, 1H), 6.58 (dd, J=10.2, 17.1 Hz, 1H), 6.67 (d, J=15.8 Hz, 1H), 7.42 (t, J=9.1 Hz, 1H), 7.80 (m, 1H), 7.90 (s, 1H), 8.15 (dd, J=2.6, 6.8 Hz, 1H), 8.51 (s, 1H), 8.56 (s, 1H), 9.88 (s, 1H), 10.03 (s, 1H).

Example 31

1a.ditosylate (1a.2TsOH)

The compound 1a (10.00 g) was added to ethanol-ethyl acetate solution (1:7, 140 mL) and stirred. This was filtered [washed with ethanol-ethyl acetate(1:7, 10 mL)] and a solution obtained by dissolving p-toluenesulfonic acid (TsOH). monohydrate (7.37 g) in ethanol-ethyl acetate solution (1:7, 20 mL) and filtering [washed with ethanol-ethyl acetate (1:7, 10 mL)] was added to the obtained solution at room temperature. After stirring at room temperature 3 hrs, the resulting solid was collected by filtration and dried under reduced pressure at 70° C. for 5 hrs to give the title compound as pale-yellow crystals (15.96 g).

1a.2TsOH: $^1$H NMR (DMSO-$d_6$) δ ppm: 1.49 (s, 6H), 2.27 (s, 6H), 2.59 (m, 2H), 2.81 (s, 3H), 3.06 (m, 2H), 3.28 (m, 2H), 3.48 (m, 2H), 5.91 (d, J=10.2 Hz, 1H), 6.38 (d, J=16.9 Hz, 1H), 6.62 (dd, J=10.2 Hz, 16.9 Hz, 1H), 7.10 (d, J=7.9 Hz, 2H), 7.49 (d, J=7.9 Hz, 2H), 7.57 (t, J=9.0 Hz, 1H), 7.72 (m, 1H), 7.93 (s, 1H), 8.05 (dd, J=2.5 Hz, 6.8 Hz, 1H), 8.88 (s, 1H), 8.94 (s, 1H), 9.39 (br s, 1H), 10.10 (s, 1H), 11.32 (br s, 1H).

Example 32

1a.trihydrochloride (1a.3HCl)

The compound 1a (1.549 g) was added to THF (40 mL), and the mixture was stirred and filtered [washed with THF (6.5 mL)]. The obtained solution was ice-cooled, and 4N hydrochloric acid-ethyl acetate solution (2.37 mL) was added dropwise. The mixture was stirred under ice-cooling for 5 hrs, and the resulting product was collected by filtration and dried under reduced pressure to give the title compound as a yellow solid (1.89 g).

1a.3HCl: $^1$H NMR (DMSO-$d_6$) δ ppm : 1.75 (s, 6H), 2.86 (s, 3H), 3.25-3.90 (m, 8H), 5.90 (dd, J=1.9, 10.3 Hz, 1H), 6.39 (dd, J=1.9, 17.0 Hz, 1H), 6.86 (dd, J=10.3, 17.0 Hz, 1H), 7.58 (t, J=9.2 Hz, 1H), 7.74 (m, 1H), 8.04 (dd, J=2.7, 6.8 Hz, 1H), 8.22 (s, 1H), 8.97 (s, 1H), 9.05 (s, 1H), 10.47 (s, 1H).

Example 33

1a.dihydrochloride (1a.2HCl)

The compound 1a (1.27 g) was added to and dissolved in THF (38 mL), and 4N hydrochloric acid-ethyl acetate solution (1.28 mL) was added dropwise with stirring. The mixture was stirred overnight at room temperature and collected by filtration. Drying gave the title compound as a white solid (1.17 g). This crude crystal (0.16 g) was suspended in isopropanol (IPA)-THF (1:1, 10 mL) and stirred in an oil bath at 70° C. The reaction mixture was allowed to stand to cool, and the product was collected by filtration and dried under reduced pressure to give the title compound as a crystalline powder (78 mg).

1a.2HCl: $^1$H NMR (DMSO-$d_6$) δ ppm: 1.55 (s, 6H), 2.80 (s, 3H), 2.90-3.80 (m, 8H), 5.90 (dd, 1H), 6.39 (dd, 1H), 6.70 (dd, 1H), 7.55 (t, 1H), 7.75 (m, 1H), 8.05 (dd, 1H), 8.08 (s, 1H), 8.91 (s, 2H), 10.30 (s, 1H).

Elemental analysis: (Calcd. for $C_{27}H_{30}Cl_3FN_6O.1.2IPA.0.5H_2O$) C, 55.11; H, 5.39; Cl, 17.88; N, 14.13; (analyzed value) C, 55.26; H, 5.19; Cl, 17.72; N, 14.12.

Example 34

1a.hydrochloride (1a.HCl)

The compound 1a (150 mg) was added to THF (3 mL) and the resulting solution was ice-cooled. 4N Hydrochloric acid-ethyl acetate solution (81 μL) was added dropwise with stirring. After stirring overnight at room temperature, the resulting product was collected by filtration and dried under reduced pressure to give the title compound as a white solid (140 mg).

1a.HCl: $^1$H NMR (DMSO-d$_6$) δ ppm: 1.45 (s, 6H), 2.78 (s, 3H), 2.61 (m, 2H), 3.02 (m, 2H), 3.10-3.75 (m, 4H), 5.85 (dd, 1H), 6.39 (dd, 1H), 6.70 (dd, 1H), 7.58 (t, 1H), 6.80 (m, 1H), 7.92 (s, 1H), 8.20 (m, 1H), 8.65 (s, 1H), 8.70(s, 1H), 10.10 (br. 3H).

Example 35

1a.dimesylate (1a.2MsOH)

The compound 1a (1.50 g) was added to and dissolved in THF (30 mL). 3N methanesulfonic acid (MsOH)-THF solution (1.99 mL) was added dropwise thereto with stirring at room temperature. After stirring overnight at room temperature, THF (15 mL) was added and the resulting product was collected by filtration and dried under reduced pressure to give the title compound as a white solid (1.98 g).

1a.2MsOH: $^1$H NMR (DMSO-d$_6$) δ ppm: 1.48 (s, 6H), 2.34 (s, 6H), 2.81 (s, 3H), 2.40-2.70 (m, 2H), 2.90-3.80 (m, 6H), 5.90 (dd, 1H), 6.39 (dd, 1H), 6.55 (m, 1H), 7.54 (t, 1H), 7.75 (m, 1H), 7.95 (s, 1H), 8.10 (m, 1H), 8.84. (s, 1H), 8.87 (br, 1H) 10.04 (s, 1H).

Example 36

1a.tosylate (1a.TsOH)

The compound 1a(1.00 g) was dissolved in ethyl acetate (70 mL) and 0.25N p-toluenesulfonic acid-ethyl acetate solution (8.27 mL) was added dropwise with stirring at room temperature. After stirring for 2 hrs at room temperature, and the resulting product was collected by filtration and dried under reduced pressure to give the title compound as a white solid (1.23 g).

1a.TsOH: $^1$H NMR (DMSO-d$_6$) δ ppm: 1.46 (s, 6H), 2.28 (s, 3H), 2.50 (m, 2H), 2.80 (s, 3H), 3.06 (m, 2H), 3.20-3.70 (m, 4H), 5.90 (d, 1H), 6.38 (d, 1H), 6.60 (dd, 1H), 7.10 (d, J=7.9 Hz, 2H), 7.40-7.60 (m, 3H), 7.80 (m, 1H), 7.92 (s, 1H), 8.10 (m, 1H), 8.70 (s, 1H), 8.79 (s, 1H), 9.35 (br, 1H), 9.98 (s, 1H), 10.20 (br, 1H).

Example 37

1a.ethanedisulfonate [1a.CH$_2$SO$_3$H)$_2$]

The compound 1a (100 mg) was dissolved in acetone (4 mL), and 0.5N ethanedisulfonate-acetone solution (0.4 mL) was added dropwise with stirring at room temperature. After stirring overnight at room temperature, the resulting product was collected by filtration and dried under reduced pressure to give the title compound as a white solid (89 mg).

1a.–(CH$_2$SO$_3$H)$_2$: $^1$H NMR (DMSO-d$_6$). δ ppm: 1.46 (s, 6H), 2.60 (m, 2H), 2.70-2.90 (m, 7H), 2.90-3.80 (m, 6H), 5.90 (d, 1H), 6.38 (d, 1H), 6.60 (dd, 1H), 7.50 (t, 1H), 7.86 (m, 1H), 7.97 (s, 1H), 8.12 (m, 1H), 8.76 (s, 2H), 9.40 (br, 1H), 10.03 (s, 1H), 10.50 (br, 1H).

Example 38

1a.diethanedisulfonate [1a.2CH$_2$SO$_3$H)$_2$]

The compound 1a (100 mg) was dissolved in acetone (2 mL) and 0.5N ethanedisulfonate-acetone solution (0.8 mL) was added dropwise with stirring at room temperature. After stirring overnight at room temperature, the resulting product was collected by filtration and dried under reduced pressure to give the title compound as a white solid (122 mg).

1a.2–(CH$_2$SO$_3$H)$_2$: $^1$H NMR (DMSO-d$_6$) δ ppm: 1.60 (d, J=2.6, 6H), 2.70-3.00 (m, 13H), 3.20 (m. 2H), 3.60 (m, 4H), 5.40 (d, 1H), 6.60 (dd, 1H), 7.60 (t, 1H), 7.70 (m, 1H), 8.00 (s, 1H), 8.10(d, 1H), 8.92 (s, 1H), 9.00 (s, 1H), 9.80 (br, 1H), 10.20 (s, 1H).

Example 39

1a.dibenzenesulfonate (1a.2PhSO$_3$H)

The compound 1a (100 mg) was dissolved in acetone (3 mL) and 0.5N benzenesulfonic acid-acetone solution (0.8 mL) was added dropwise with stirring at room temperature. After stirring overnight at room temperature, the resulting product was collected by filtration and dried under reduced pressure to give the title compound as a white solid (60 mg).

1a.2PhSO$_3$H: $^1$H NMR (DMSO-d$_6$) δ ppm: 1.49 (s, 6H), 2.60 (m, 2H), 2.81 (s, 3H), 3.10 (m, 2H), 3.30 (d, 2H) 3.50 (d, 2H), 5.90 (d, 1H), 6.39 (d, 1H), 6.60 (dd, 1H) 7.32 (m, 6H), 7.60 (m, 5H), 7.75 (m, 1H), 7.92 (s, 1H), 8.07 (m, 1H), 8.88 (s, 1H), 8.96 (s, 1H), 9.40 (br, 1H), 10.10 (s, 1H).

Example 40

Preparation (1) of 1a.½hydrate (1a.½H$_2$O) type A crystal form

Acetone (126 mL) was added to compound 1a (9.00 g) and the mixture was stirred with heating at an inner temperature of 53° C. After complete dissolution of the solid, the solution was cooled to an inner temperature of 24° C. over 7 hrs with stirring. The precipitate was collected by filtration, and the filtration residue was washed with acetone and dried under reduced pressure at 80° C. for 4 hrs to give the title compound as pale-yellow crystals (7.32 g, 81%).

The XRD pattern of this crystal is shown in FIG. 1, and this crystal is taken as type A crystal form. The characteristic peaks shown in FIG. 1 are as follows. characteristic peak (2θ, ±0.2°)

7.1°, 10.6°, 11.9°, 12.2°, 13.8°, 17.3°, 18.4°IR (KBr) ν cm$^{-1}$: 3376, 2809, 1676, 1628, 1562, 1535, 1497, 1421, 1213, 1177. melting point: 131-133° C.

Elemental analysis: (calcd. for C$_{27}$H$_{28}$ClFN$_6$O.½H$_2$O) C, 62.85; H, 5.66; N, 16.29; (analyzed value) C, 62.68; H, 5.58; N, 16.14.

Example 41

Preparation (2) of 1a.½H$_2$O type A crystal form

Toluene (3.0 mL) was added to compound 1a (150 mg) and the suspension was stirred at room temperature for 69 hrs. The suspension was filtered and the filtration residue was washed with toluene and dried under reduced pressure at 60° C. for 6 hrs to give the title compound as pale-yellowish white crystals (131 mg, 87%). The XRD pattern of this crystal showed a type A crystal form.

Example 42

Preparation (3) of 1a.½H$_2$O type a crystal form

THF (1.0 mL) was added to compound 1a (150 mg) and the mixture was heated to an inner temperature of about 70° C. After complete dissolution of the solid, heptane (1.3 mL) was gradually added dropwise with stirring, and the solution was cooled to room temperature. The precipitate was collected by filtration, and the filtration residue was washed with THF-heptane (1:2) and dried under reduced pressure at 60° C. for 6 hrs to give the title compound as pale-yellowish white crystals (90.5 mg, 59% The XRD pattern of this crystal showed a type A crystal form.

Elemental analysis: (calcd. for C$_{27}$H$_{28}$ClFN$_{60}$.1/2H$_2$O) C, 62.85; H, 5.66; N, 16.29; (analyzed value) C, 62.68; H, 5.58; N, 16.14.

Example 43

Preparation (4) of 1a.½H$_2$O type a crystal form

Ethyl acetate (2.0 mL) was added to compound 1a (200 mg) and the mixture was heated to an inner temperature of about 70° C. After complete dissolution of the solid, heptane (3.0 mL) was gradually added dropwise with stirring, and the solution was cooled to room temperature. The precipitate was collected by filtration, and the filtration residue was washed with ethyl acetate-heptane (1:2) and dried under reduced pressure at 60° C. for 6 hrs to give the title compound as pale-yellowish white crystals (119 mg, 79%). The XRD pattern of this crystal showed a type A crystal form.

Example 44

Preparation (1) of 1a.2TsOH type a crystal form

Ethanol (3.41 L) was added to the crude crystal (568.23 g) obtained by the method of Example 31 and the mixture was stirred with heating to an inner temperature of 70° C. After complete dissolution of the solid, the solution was cooled to an inner temperature of 26° C. over 16 hrs with stirring (rate of stirring about 90 rpm). The precipitate was collected by filtration, and the filtration residue was washed with ethanol and dried under reduced pressure at 60° C. for 20 hrs and at 75° C. for 12 hrs to give the title compound as pale-yellow crystals (488.57 g, 85%).

The XRD pattern of this crystal is shown in FIG. 2, and this crystal is taken as type A crystal form. The characteristic peaks shown in FIG. 2 are as follows. characteristic peak (2θ, ±0.2°)

3.3°, 6.6°, 7.5°, 9.4°, 13.9°, 17.4°, 19.1° melting point: 208.5-210° C.

Elemental analysis: [calcd. for C$_{41}$H$_{44}$ClFN$_6$O$_7$S$_2$.1/2H$_2$O (1a.2TsOH.½H$_2$O)] C., 57.23; H, 5.27; N, 9.77;S, 7.45 (analyzed value) C, 57.05; H, 5.09; N, 9.74.; S,7.45

Example 45

Preparation (2) of 1a.2TsOH type a crystal form

Isopropyl alcohol (5.0 mL) was added to the crude crystal (148 mg) obtained by the method of Example 31 and the mixture was stirred with heating to an inner temperature of 80° C. After complete dissolution of the solid, the solution was cooled to room temperature with stirring. The precipitate was collected by filtration, and the filtration residue was washed with isopropyl alcohol and dried under reduced pressure at 60° C. for 6 hrs to give the title compound as pale-yellow crystals (133 mg, 90%). The XRD pattern of this crystal showed a type A crystal form.

Example 46

Preparation (3) of 1a.2TsOH type a crystal form

THF (8.0 mL) was added to the crude crystal (107 mg) obtained by the method of Example 31 and the suspension was stirred at room temperature for 65 hrs. The suspension was filtered and the filtration residue was washed with THF and dried under reduced pressure at 60° C. for 3 hrs to give the title compound as pale-yellow crystals (97 mg, 90%). The XRD pattern of this crystal showed a type A crystal form.

Example 47

Preparation (4) of 1a.2TsOH type a crystal form

Acetonitrile (6.5 mL) was added to the crude crystal (147 mg) obtained by the method of Example 31 and the mixture was heated to an inner temperature of about 70° C. with stirring. After complete dissolution of the solid, the solution was cooled to room temperature with stirring. The precipitate was collected by filtration, and the filtration residue was washed with acetonitrile and dried under reduced pressure at 60° C. for 6 hrs to give the title compound as pale-yellow crystals (113 mg, 77%). The XRD pattern of this crystal showed a type A crystal form.

Example 48

Preparation (5) of 1a.2TsOH type a crystal form

Ethanol (2.5 mL) was added to the crude crystal (158 mg) obtained by the method of Example 31 and the mixture was heated to an inner temperature of about 80° C. with stirring. After complete dissolution of the solid, ethyl acetate (8.0 mL) was added dropwise with stirring and the solution was cooled to room temperature. The precipitate was collected by filtration, and the filtration residue was washed with ethanol:ethyl acetate (1:5) and dried under reduced pressure at 60° C. for 6 hrs to give the title compound as pale-yellow crystals (125 mg, 79%). The XRD pattern-of this crystal showed a type A crystal form.

Example 49

Preparation (1) of 1a.3HCl.4H$_2$O type A crystal form

Methanol (310 mL) was added to the crude crystal (12.73 g) obtained by the method of Example 32 and the mixture was heated to an oil bath temperature of about 70°0 C. with stirring. After complete dissolution of the solid, ethyl acetate (120 mL) was gradually added dropwise with stirring at the same temperature, and the solution was gradually cooled to room temperature with stirring. The precipitate was collected by filtration, and dried under reduced pressure at 50° C. for 4 hrs. The obtained crystals were pulverized in a mortar and maintained under 75% humidity at room temperature for three days to give the title compound (10.00 g) as colorless crystals.

The XRD pattern of this crystal is measured and this crystal shape is taken as type A crystal form.

Elemental analysis: [calcd. for $C_{27}H_{39}Cl_4FN_6O_5$ (1a.3HCl.4H$_2$O)] C, 47.10; H, 5.71; N, 12.21; Cl, 20.60; (analyzed value) C, 47.29; H, 4.67; N, 12.31; Cl, 20.45. moisture analysis (Karl-Fisher method): (calcd.) 10.46%; (analyzed value) 10.20% (moisture vaporization—coulometric titration); 10.15% (volumetric method).

Example 50

Preparation (2) of 1a.3HCl.4H$_2$O type A crystal form

Methanol (17 mL) was added to the crude crystal (0.400 g) obtained by the method of Example 32 and the mixture was heated to an oil bath temperature of about 70° C. with stirring. After complete dissolution of the solid, the solution was gradually cooled to room temperature with stirring. The precipitate was collected by filtration, and dried under reduced pressure at 80° C. for 7 hrs to give the title compound (0.242 g) as pale-yellow crystals. The XRD pattern of this crystal showed a type A crystal form.

Example 51

Preparation (3) of 1a.3HCl.4H$_2$O type A crystal form

Water (8.0 mL) was added to the crude crystal (0.400 g) obtained by the method of Example 32 and the mixture was stirred at room temperature. After complete dissolution of the solid, acetone (50 mL) was added at room temperature with stirring. The precipitate was collected by filtration and dried under reduced pressure at 80° C. for 7 hrs to give the title compound as colorless crystals (0.143 g). The XRD pattern of this crystal showed a type A crystal form.

Example 52

Preparation (4) of 1a.3HCl.4H$_2$O type A crystal form

Acetonitrile (6 mL) was added to the crude crystal (0.400 g) obtained by the method of Example 32 and the mixture was stirred at room temperature for 2 hrs. The suspension was filtered and the obtained crystals were dried under reduced pressure at 80° C. for 7 hrs to give the title compound (0.300 g) as colorless crystals. The XRD pattern of this crystal showed a type A crystal form.

Example 53

Preparation (5) of 1a.3HCl.4H$_2$O type A crystal form

Water (2.0 mL) was added to the crude crystal (0.400 g) obtained by the method of Example 32 and the mixture was heated to an oil bath temperature at 70° C. with stirring. After complete dissolution of the solid, this solution was added dropwise to acetone (30 mL). The precipitate was collected by filtration and dried under reduced pressure at 80° C. for 7 hrs to give the title compound as colorless crystals (0.313 g). The XRD pattern of this crystal showed a type A crystal form.

Example 54

1a.H$_2$SO$_4$

Ethyl acetate (80 mL) was added to 1a (1.09 g, 2.15 mmol) for dissolution and a solution (4.31 mL, 2.15 mmol), wherein ethyl acetate had been added to concentrated sulfuric acid (0.68 ml L, 12.5 mmol) to the total amount of 25 mL, was added thereto. The mixture was stirred at room temperature for 15 hrs. The precipitated crystals were collected by filtration, and the crystals were washed with ethyl acetate and dried in vacuo at 60° C. for 4 hrs to give pale-yellow crude crystals (1.27 g, 97.8%)

$^1$H NMR (270 MHz, DMSO-d$_6$) δ ppm: 1.45 (s, 6H), 2.79 (s, 3H), 2.90-3.50 (m, 8H), 5.86 (dd, 1H), 6.34 (dd, 1H), 6.59 (dd, 1H), 7.46 (t, 1H), 7.80-7.86 (m, 1H), 7.92 (s, 1H), 8.18 (dd, 1H), 8.63 (s, 1H), 8.69 (s, 1H), 9.95 (s, 1H), 10.01 (br s, 1H).

Example 55

1a.1.5H$_2$SO$_4$.H$_2$O

Ethyl acetate (80 mL) was added to 1a(1.08 g, 2.14 mmol) for dissolution and a solution (6.42 mL, 3.21 mmol), wherein ethyl acetate had been added to concentrated sulfuric acid (0.68 ml L, 12.5 mmol) to the total amount of 25 mL, was added thereto. The mixture was stirred at room temperature for 18 hrs. The precipitated crystals were collected by filtration, and the crystals were washed with ethyl acetate and dried under reduced pressure at 70° C. for 3 hrs to give yellow crude crystals (1.34 g, 95.9%). To this crude crystal (889 mg, 1.36 mmol) was added methanol (44.4 mL), and the mixture was heated under reflux to allow dissolution. After stirring at room temperature for 3 hrs, the mixture was allowed to cool to room temperature. The precipitated crystals were collected by filtration and the obtained crystals were washed with methanol and dried under reduced pressure at 70° C. for 2 hrs to give yellow crystals (604 mg, 68.0%).

$^1$H NMR (270 MHz, DMSO-d$_6$) δ ppm: 1.42 (s, 6H), 2.46-2.64 (m, 2H), 2.80 (s, 3H), 2.95-3.11 (m, 2H), 3.16-3.34 (m, 2H), 3.40-3.54 (m, 2H), 5.89 (dd, 1H), 6.36 (dd, 1H), 6.61 (dd, 1H), 7.52 (t, 1H), 7.73-7.79 (m, 1H), 7.94 (s, 1H), 8.10 (dd, 1H), 8.80 (s, 2H), 10.04 (s, 1H), 10.75 (br s, 1H).

Elemental analysis: (calcd. for 1a.1.5H$_2$SO$_4$.H$_2$O) C, 48.25; H, 4.95; N, 12.50; S, 7.16; (analyzed value) C, 48.47; H, 4.95; N, 12.56; S, 7.11.

Synthetic Example 13

Synthesis of trifluoromethanesulfonic acid 4-(3-acetylphenylamino)-7-methoxy-6-quinazolinyl ester (6a)

1) A solution (200 mL) of acetic acid 4-chloro-7-methoxy-6-quinazolinyl ester [described in U.S. Pat. Nos. 5,770,599 and 5,770,603] (3.74 g, 14.8 mmol) and 3-aminoacetophenone (2.0 g, 14.8 mmol) in isopropanol was heated under reflux for 5 hrs. After allowing to stand to cool, the precipitate was collected by filtration to give acetic acid 4-(3-acetylphenylamino)-7-methoxy-6-quinazolinyl ester hydrochloride (4.78 g, yield as monohydrochloride 83%). To a solution (100 mL) of this compound (3.0 g, 7.74 mmol) in methanol was added 28% aqueous ammonia (2 mL), and the mixture was stirred at room temperature for 4 hrs and then refluxed. The produced precipitate was collected by filtration and dried under reduced pressure to give 1-[3-(6-hydroxy-7-methoxy-4-quinazolinylamino)phenyl]ethanone (2.07 g, 87%).

2) A solution (20 mL) of 1-[3-(6-hydroxy-7-methoxy-4-quinazolinylamino)phenyl]ethanone (870 mg, 2.8 mmol) and pyridine (0.34 mL, 4.2 mmol) in acetonitrile was stirred on an ice bath and trifluoromethanesulfonic acid anhydride (0.57 mL, 3.4 mmol) was added dropwise. The reaction solution was gradually warmed up to room temperature and, after stirring at room temperature for 2 hrs, the mixture was concentrated. Aqueous sodium hydrogen carbonate was added to the residue and the mixture was stirred at room temperature for 30 min. The product was filtered and dried under reduced pressure to give the title compound 6a (1.20 g, 98%).

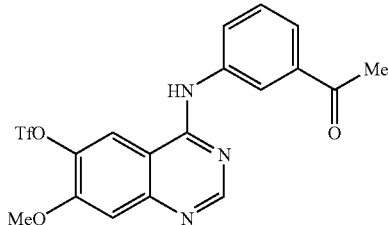

6a $^1$H NMR (300 MHz, CDCl$_3$) δ ppm: 2.65 (s, 3H), 4.06 (s, 3H), 7.40 (s, 1H), 7.53 (t, J=7.9 Hz, 1H), 7.76 (br d, J=7.8 Hz, 1H), 7.72-7.83 (m, 1H), 7.91 (br s, 1H), 8.16 (br d, J=8.9 Hz, 1H), 8.24 (t, J=1.8 Hz, 1H), 8.75 (s, 1H).

Synthetic Example 14

Synthesis of trifluoromethanesulfonic acid 4-(3-chloro-4-fluorophenylamino)-7-methoxy-6-quinazolinyl ester (6b)

In the same manner as in-Synthetic Example 13-2) and using 4-(3-chloro-4-fluorophenylamino)-7-methoxyquinazolin-6-ol, the objective 6-triflate compound 6b was obtained.

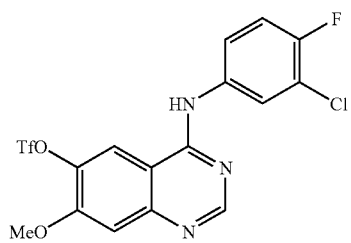

6b

6b: $^1$H NMR (300 MHz, DMSO-d$_6$) δ ppm: 4.07 (s, 3H), 7.45 (t, J=9.1 Hz, 1H), 7.51 (s, 1H), 7.76 (m, 1H), 8.09 (dd, J=2.5, 6.8 Hz, 1H), 8.64 (s, 1H), 8.68 (s, 1H), 9.94 (s, 1H).

Synthetic Example 15

Synthesis of trifluoromethanesulfonic acid 4-(3-methoxyphenylamino)-7-methoxy-6-quinazolinyl ester (6c)

In the same manner as in Synthetic Example 13-2) and using 4-(3-methoxyphenylamino)-7-methoxyquinazolin-6-ol, the objective 6-triflate compound 6c (quantitative) was obtained.

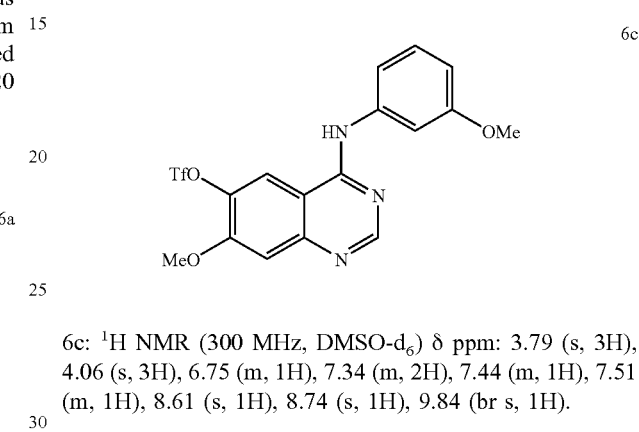

6c

6c: $^1$H NMR (300 MHz, DMSO-d$_6$) δ ppm: 3.79 (s, 3H), 4.06 (s, 3H), 6.75 (m, 1H), 7.34 (m, 2H), 7.44 (m, 1H), 7.51 (m, 1H), 8.61 (s, 1H), 8.74 (s, 1H), 9.84 (br s, 1H).

Synthetic Example 16

Synthesis of trifluoromethanesulfonic acid 4-(3-chloro-4-fluorophenylamino)-6-methoxy-7-quinazolinyl ester (6d)

1) Using 7-benzyloxy-4-chloro-6-methoxyquinazolin hydrochloride [described in Hennequin et al., *J. Med. Chem.* 1999, 42 (26), 5369-5389] and 3-chloro-4-fluoroaniline and in accordance with the above-mentioned method of Hennequin et al. or the method of Synthetic Example 13, the compound was converted to 7-benzyloxy-6-methoxy-4-quinazolinyl)-(3-chloro-4-fluorophenyl)amine hydrochloride (yield 83%). Trifluoroacetic acid (7 mL) was added to this compound (412 mg) and the mixture was heated under reflux for 90 min. After allowing to stand to cool, the reaction mixture was poured into ice water. The precipitate was collected by filtration, and the filtration residue was dissolved in methanol and dilute aqueous ammonia was added until alkalified. The precipitate was collected by filtration, washed with water and diethyl ether and dried under reduced pressure to give 4-(3-chloro-4-fluorophenylamino)-6-methoxyquinazolin-7-ol (quantitative). This compound was reacted in the same manner as in Synthetic Example 13-2). After the completion of the reaction, the reaction mixture was poured into 1N aqueous hydrochloric acid and extracted with ethyl acetate. The organic layer was washed with water, aqueous sodium hydrogen carbonate and saturated brine, and dried over anhydrous magnesium sulfate. The solvent was evaporated under reduced pressure. The residue was purified by silica gel column chromatography (hexane-ethyl acetate) to give the objective 7-triflate compound 6d (66%).

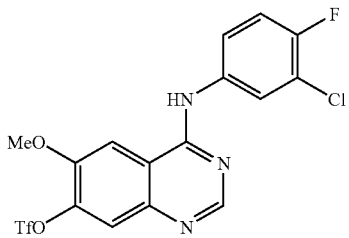

6d: ¹H NMR (300 MHz, DMSO-d₆) δ ppm: 4.09 (s, 3H), 7.49 (t, J=9.1 Hz, 1H), 7.78 (m, 1H), 7.91 (s, 1H), 8.10 (dd, J=2.5, 6.8 Hz, 1H), 8.20 (s, 1H), 8.61 (s, 1H), 9.92 (s, 1H).

Synthetic Example 17

Synthesis of trifluoromethanesulfonic acid 4-(3-chloro-4-fluorophenylamino)-7-ethoxy-6-quinazolinyl ester (6e)

1) 6,7-Diethoxy-3H-quinazolin-4-one (120.9 g, 516 mmol) was added to methanesulfonic acid (723 mL), and L-methionine (88.53 g, 593 mmol) was gradually added over 10 min period at an inner temperature of 59 to 71° C. After stirring at 80° C. to 104° C. for 11 hrs, the mixture was allowed to stand to cool. Water (3 L) and then 48% aqueous sodium hydroxide solution (930 g) were added. The precipitate was collected by filtration and washed with water (200 mL×2) to give 7-ethoxy-6-hydroxy-3H-quinazolin-4-one (97.45 g, 473 mmol, 92%).

2) 7-Ethoxy-6-hydroxy-3H-quinazolin-4-one (106.4 g, 516 mmol) was added to acetic anhydride (825 mL) and the mixture was stirred at an inner temperature of 88° C. Pyridine (107 mL) was added dropwise over 10 min, and the mixture was then stirred at an inner temperature of 98° C. to 103° C. for 1.5 hrs. After allowing to stand to cool, ice water (3 L) was added, and the product was collected by filtration and washed with water (50 mL×4). Methanol (400 mL) and 1N sodium hydroxide (100 mL) were added to the crystal and the mixture was stirred for 5 min. The resulting crystals were collected by filtration and combined with the crystals obtained by the first filtration to give the objective acetic acid 7-ethoxy-4-oxo-3,4-dihydroquinazolin-6-yl ester (49.3 g, 39%).

3) To the above-mentioned ester compound (60.14 g, 242 mmol) were added dropwise thionyl chloride (810 mL) and DMF (16.8 mL) at an inner temperature of 16° C. to 21° C. and the mixture was stirred at an inner temperature of 63° C. to 65° C. for 2 hrs. After allowing to stand to cool, the reaction mixture was concentrated, and toluene (500 mL) was added and the mixture was concentrated. This step was repeated twice. The residue was dissolved in chloroform (300 mL), washed with saturated aqueous sodium hydrogen carbonate (250 mL×1, 300 mL×1) and dried. The solvent was evaporated under reduced pressure and the residue was purified by silica gel column chromatography to give acetic acid 4-chloro-7-ethoxy-6-quinazolinyl ester (29.2 g, 45%).

4) Isopropanol (250 mL) and 3-chloro-4-fluoroaniline (5.86 g, 40.3 mmol) were added to acetic acid 4-chloro-7-ethoxy-6-quinazolinyl ester (10 g, 40.3 mmol) and the mixture was stirred at an oil bath temperature of 90° C. for 2 hrs. After allowing to stand to cool, the product was collected by filtration, dried and added to methanol (120 mL). 28% Aqueous ammonia (12 mL) was added, and after stirring at room temperature, water (200 mL) was added. The precipitated product was collected by filtration, washed with water (100 mL), and dried under reduced pressure to give 4-(3-chloro-4-fluoro-phenylamino)-7-ethoxyquinazolin-6-ol (10.65 g, 79%).

¹H NMR (300 MHz, DMSO-d₆) δ ppm: 1.44 (t, J=6.9 Hz, 3H), 4.34 (q, J=6.9 Hz, 2H), 7.19 (s, 1H), 7.41 (t, J=6.9 Hz, 1H), 7.80 (s, 1H), 7.83 (m, 1H), 8.22 (dd, J=2.5, 6.9 Hz, 1H), 8.47 (s, 1H), 9.48 (s, 1H), 9.60 (br s, 1H).

5) A solution (350 mL) of 4-(3-chloro-4-fluoro-phenylamino)-7-ethoxyquinazolin-6-ol (10.5 g, 31.5 mmol) in acetonitrile was stirred on an ice bath, and pyridine (4.13 mL, 51.1 mmol) and trifluoromethanesulfonic anhydride (7.95 mL, 47.3 mmol) were added. The mixture was stirred at room temperature for 15 hrs.

The mixture was concentrated under reduced pressure to an about half amount and water (700 mL) and methanol (200 mL) were added. The resulting solid was collected by filtration and dried under reduced pressure to give the title compound 6e (9.8 g, 67%) as a white solid.

6e: ¹H NMR (300 MHz, DMSO-d₆) δ ppm: 1.42 (t, J=6.9 Hz, 3H) 4.35 (q, J=6.9 Hz, 2H), 7.48 (t, J=9.1 Hz, 1H), 7.50 (s, 1H), 7.76 (m, 1H), 8.11 (m, 1H), 8.65 (s, 1H), 8.70 (s, 1H), 9.98 (s, 1H).

Example 56

Nitrogen was bubbled into a solution (20 mL) of 6-triflate compound 6b (5.63 g, 12.46 mmol) and compound 4a (2.49 g, 14.95 mmol) in DMF for 10 min. and triethylamine (4.30 mL, 31.15 mmol), tetrakis(triphenylphosphine)palladium (283 mg) and copper iodide(I) (95 mg) were added. The mixture was stirred at 50° C. for 1 hr. The mixture was concentrated under reduced pressure, and the residue was purified by silica gel column (chloroform-methanol) and recrystallized from acetonitrile-water to give the objective coupling compound 1ba (2.71 g, 46%) as white crystals.

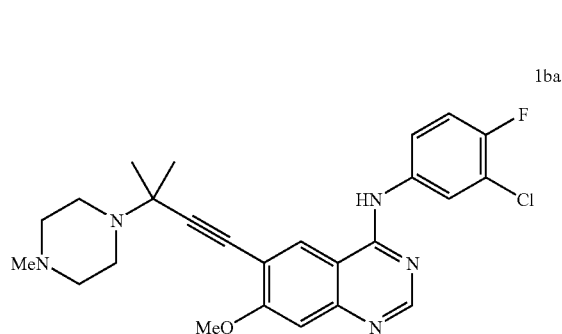

1ba

1ba: ¹H NMR (300MHz, CDCl₃) δ ppm: 1.52 (s, 6H), 2.32 (s, 3H), 2.57 (br s, 4H), 2.85 (br s, 4H), 3.98 (s, 3H), 7.16 (t, J=8.7 Hz, 1H), 7.18 (s, 1H), 7.61 (m, 1H), 7.97 (dd, J=2.6, 6.6 Hz, 1H), 8.06 (br s, 1H), 8.18 (s, 1H), 8.65 (s, 1H).

Example 57

Using 6-triflate compound 6b and compound 4c and in the same manner as in Example 56, compound 1bb (yield 66%) was obtained as a white-pale pink crystalline powder.

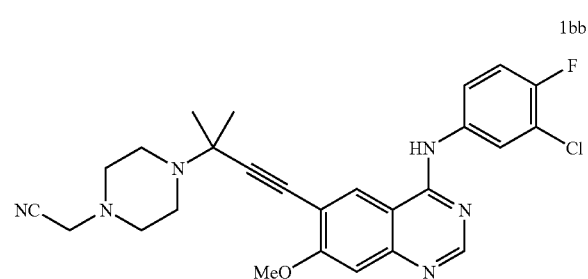

1bb

1bb: ¹H NMR (300 MHz, CDCl₃) δ ppm: 1.52 (s, 6H), 1.87 (s, 3H), 2.60-2.80 (m, 8H), 3.54 (s, 2H), 3.98 (s, 3H), 7.17 (t, J=8.6 Hz, 1H), 7.19 (s, 1H), 7.54 (m, 1H), 7.60 (br s, 1H), 7.94 (dd, J=2.6, 6.5 Hz, 1H), 8.00 (s, 1H), 8.67 (s, 1H).

Example 58

Using 6-triflate compound 6b and 4-(1,1-dimethyl-2-propynyl)piperazine (see Synthetic Example 9) and in the same manner as in Example 56, the reaction was carried out. The reaction mixture was concentrated under reduced pressure and partitioned between chloroform-aqueous sodium hydrogen carbonate. The organic layer was concentrated under reduced pressure. The purified crude substance was suspended in acetonitrile, stirred and the obtained solid collected by filtration was purified by silica gel column chromatography to give the objective compound 1bc (yield 73%).

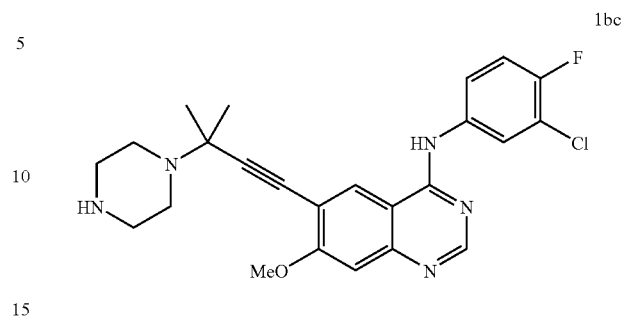

1bc

1bc: ¹H NMR (300 MHz, DMSO-d₆) δ ppm: 1.45 (s, 6H), 2.83 (br s, 4H), 3.11 (br s, 4H), 3.97 (s, 3H), 7.22 (s, 1H), 7.42 (t, J=9.1 Hz, 1H), 7.81 (m, 1), 8.16 (m, 1H), 8.56 (s, 1H), 8.58 (s, 1H), 9.83 (s, 1H).

4-(1,1-dimethyl-2-propynyl)piperazine (synthesized according to the method of Synthetic Example 1 using an excess of piperazine (2.5 equivalent amount) as a starting material, yield 42%): ¹H NMR (300 MHz, DMSO-d₆) δ ppm: 1.39 (s, 6H), 2.30 (s, 1H), 2.61 (br s, 4H), 2.93 (m, 4H).

Example 59

A solution (5 mL) of compound 1bc (200 mg, 0.44 mmol), propyl bromide (40 µL, 0.44 mmol) and potassium carbonate (183 mg, 1.32 mmol) in DMF was stirred with heating at 60 to 70° C. Propyl bromide was sequentially added (16 µL×2), and after stirring with heating for the total of 3 hrs, ethyl acetate and aqueous ammonium chloride solution were added. The organic layer was dried and the solvent was evaporated under reduced pressure. The residue was purified by silica gel column chromatography (chloroform-methanol). A fraction containing the product was concentrated and suspended in acetonitrile-water, and after stirring, the resulting product was collected by filtration to give the objective compound 1bd (173 mg, 79%).

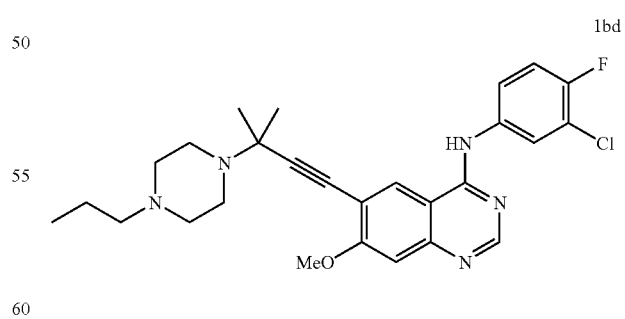

1bd

1bd: ¹H NMR (300 MHz, DMSO-d₆) δ ppm: 0.85 (t, J=7.4 Hz, 3H), 1.30-1.50 (m, 2H), 1.42 (s, 6H), 2.21 (t, J=7.4 Hz, 2H), 2.41 (br s, 4H), 2.69 (br s, 4H), 3.97 (s, 3H), 7.22 (s, 1H), 7.44 (t, J=9.3 Hz, 1H), 7.83 (m, 1H), 8.18 (dd, J=2.4, 6.9 Hz, 1H), 8.57 (s, 1H), 8.57 (s, 1H), 9.86 (br s, 1H).

Example 60

Using compound 1bc and isobutyl iodide and in the same manner as in Example 59, the compound was converted to the objective compound 1b (yield 48%).

1be

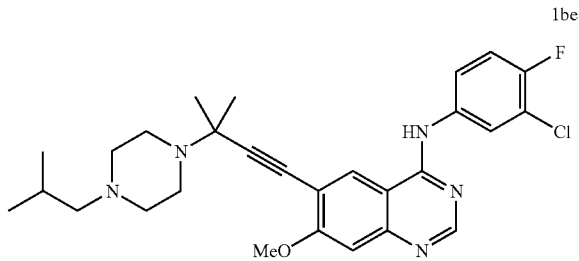

1be: $^1$H NMR (300 MHz, DMSO-d$_6$) δ ppm: 0.85 (d, J=6.3 Hz, 6H), 1.43 (s, 6H), 1.76 (m, 1H), 2.04 (m, 2H), 2.39 (br s, 4H), 2.70 (br s, 4H), 2.70 (br s, 4H), 4.02 (s, 3H), 7.22 (s, 1H), 7.44 (t, J=9.0 Hz, 1H), 7.84 (m, 1H), 8.19 (m, 1H), 8.57 (s, 2H), 9.86 (s, 1H).

Example 61

A solution (5 mL) of compound 4a (0.44 g, 2.65 mmol) in dichloromethane was stirred under ice-cooling and a 1M solution (2.7 mL, 2.7 mmol) of 4,4,5,5-tetramethyl-1,3,2-dioxaborolane (pin-BH) in THF and RhCl(PPh$_3$)$_3$ (25 mg) were added thereto. After stirring at room temperature for 7 hrs, a 1M THF solution (2.7 mL, 2.7 mmol) of pin-BH was added. After stirring overnight, a 1M THF solution (2.7 mL, 2.7 mmol) of pin-BH was added. After stirring for 9 hrs, the mixture was cooled to −10° C. and aqueous sodium hydrogen carbonate was added. The mixture was extracted with diethyl ether (40 mL×1, 10 mL×1), dried and concentrated. The compound 6d (452 mg, 1.0 mmol), PdCl$_2$ (dppf).CH$_2$Cl$_2$ [dppf=1,1'-bis(diphenylphosphino)ferrocene] (27 mg, 0.03 mmol), 2M aqueous sodium carbonate solution (4.5 mL) and DMF (6 mL) were added to the obtained oil (1.08 g). This mixture was subjected several times to the step of degassing and displacement with nitrogen. The mixture was stirred at 80° C. for 1 hr. The reaction mixture was allowed to warm to room temperature, and water (30 mL) was added. The product was extracted with ethyl acetate (30 mL×3). The organic layer was washed with saturated brine (20 mL), dried and concentrated. Diethyl ether was added to the residue and insoluble material was filtered off. The filtrate was concentrated to give the objective 1bf (115 mg, 25%) as an oil. This was dissolved in diethyl ether (4 mL) and 4N hydrochloric acid/ethyl acetate (61 μL) was added under ice-cooling. The mixture was stirred at room temperature for a while and the precipitate was collected by filtration to give 1bf.hydrochloride (68 mg, yield 55% as monohydrochloride) as a pale-yellow powder.

1bf

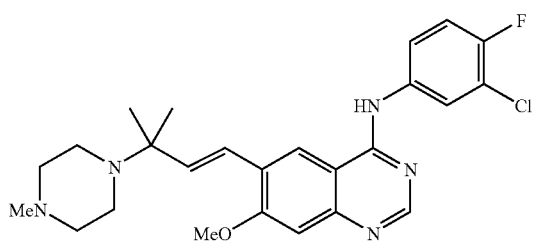

1bf.HCl: $^1$H NMR (300 MHz, CDCl$_3$+D$_2$O) δ ppm: 1.50 (s, 6H), 2.70 (s, 3H), 2.80-3.60 (m, 8H), 3.97 (s, 3H), 6.67 (d, J=16.2 Hz, 1H), 6.90 (d, J=16.2 Hz, 1H), 7.12 (t, J=8.8 Hz, 1H), 7.30 (s, 1H), 7.71 (m, 1H), 8.02 (dd, J=2.4, 6.6 Hz, 1H), 8.57 (s, 1H), 8.72 (s, 1H), 9.70 (br s, 1H).

Example 62

Using compound 6a and compound 4a and in the same manner as in Example 56, the objective product compound 1bg (yield 59%) was obtained.

1bg

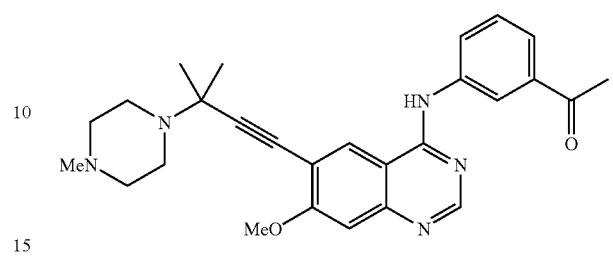

1bg: $^1$H NMR (300 MHz, CDCl$_3$) δ ppm: 1.53 (s, 6H), 2.31 (s, 3H), 2.55 (br s, 4H), 2.65 (s, 3H), 2.84 (br s, 4H), 3.99 (s, 3H), 7.20 (s, 1H), 7.52 (t, J=7.9 Hz, 1H), 7.74 (br d, J=7.7 Hz, 1H), 7.78 (br s, 1H), 8.05 (s, 1H), 8.16 (dd, J=2.1, 8.1 Hz, 1H), 8.69 (s, 1H).

Example 63

Using compound 6c and compound 4a and in the same manner as in Example 56, the objective product compound 1bh (yield 68%) was obtained.

1bh

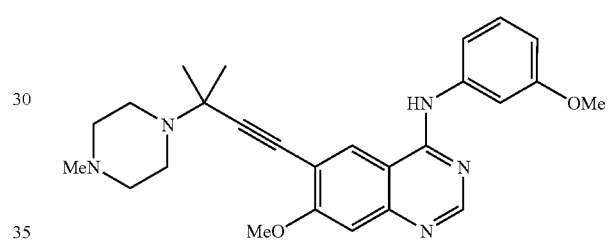

1bh: $^1$H NMR (300 MHz, DMSO-d$_6$) δ ppm: 1.43 (s, 6H), 2.16 (s, 3H), 2.37 (br s, 4H), 2.69 (br s, 4H), 3.78 (s, 3H), 3.96 (s, 3H), 6.70 (dd, J=2.2, 8.2 Hz, 1H), 7.20 (s, 1H), 7.28 (t, J=8.2 Hz, 1H), 7.42-7.55 (m, 2H), 8.54 (s, 1H), 8.60 (s, 1H), 9.72 (br s, 1H).

Examples 64, 65

Using compound 6d and compounds 4a and 4c and in the same manner as in Example 56, they were converted to the objective product compounds 1bi, 1bj, respectively.

Example 64

1bi

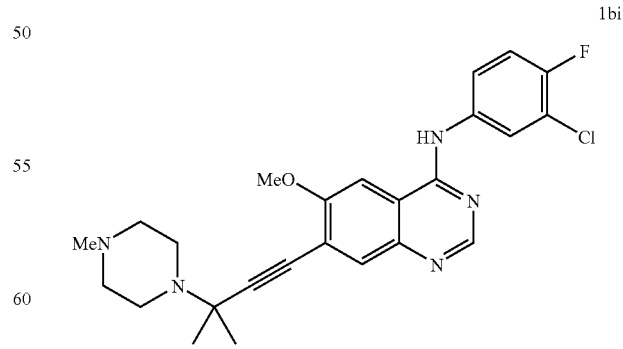

1bi: yield 78%; $^1$H NMR (300 MHz, DMSO-d$_6$) δ ppm: 1.43 (s, 6H), 2.18 (s, 3H), 2.40 (br s, 4H), 2.68 (br s, 4H), 4.00 (s, 3H), 7.47 (t, J=9.2 Hz, 1H), 7.75 (S, 1H), 7.81 (m, 1H), 7.88 (s, 1H), 8.13 (dd, J=2.7, 6.6 Hz, 1H), 8.54 (s, 1H), 9.77 (s, 1H).

Example 65

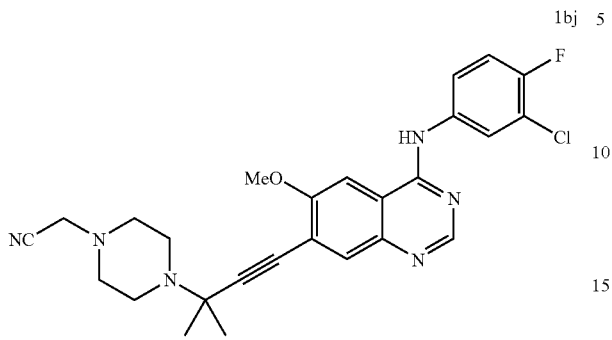

1bj

1bj: yield 78%; ¹H NMR (300 MHz, DMSO-d$_6$) δ ppm: 1.44 (s, 6H), 2.56 (br s, 4H), 2.73 (br s, 4H), 3.73 (s, 2H), 4.00 (s, 3H), 7.47 (t, J=9.2 Hz, 1H), 7.76 (s, 1H), 7.81 (m, 1H), 7.88 (s, 1H), 8.13 (dd, J=2.4, 6.9 Hz, 1H), 8.54 (s, 1H), 9.77 (s, 1H).

Example 66

A solution of amino compound 2c (700 mg, 1.46 mmol) obtained by the method of Example 3 in pyridine (7 mL) was cooled to 0° C. to 50° C. and methanesulfonyl chloride (125 μL, 1.61 mmol) was gradually added dropwise. The reaction vessel was naturally warmed while placed in an ice bath, and the reaction mixture was poured into aqueous sodium hydrogen carbonate. The precipitated solid was collected by filtration and washed with cold water. The obtained purified crude substance was subjected to silica gel column chromatography (chloroform-methanol) and the obtained compound was suspension-washed with acetonitrile. The product was collected by filtration and dried under reduced pressure to give the objective compound 1ca (552 mg, 68%).

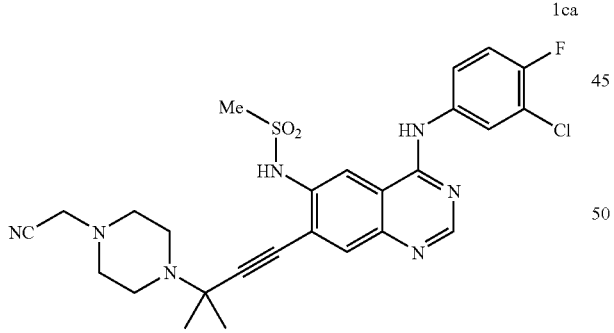

1ca

1ca: yield 68%; ¹H NMR (270 MHz, DMSO-d$_6$) δ ppm: 1.48 (s, 6H), 2.55 (br s, 4H), 2.74 (br s, 4H), 3.12 (s, 3H), 3.73 (s, 2H), 7.47 (t, J=9.2 Hz, 1H), 7.80 (m, 1H), 7.85 (s, 1H), 8.13 (dd, J=2.7, 7.0 Hz, 1H), 8.46 (s, 1H), 8.62 (s, 1H), 10.09 (s, 1H).

Examples 67-77

In the same manner as in Example 66, the compounds were synthesized from the corresponding amino compound 2.

Example 67

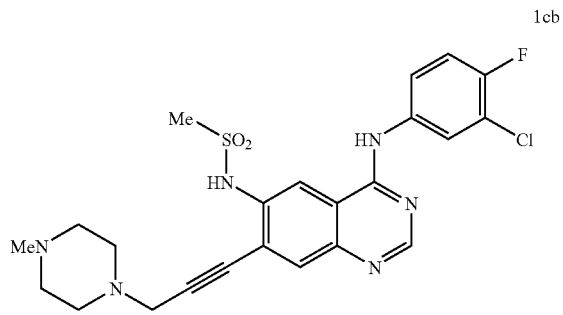

1cb

1cb: yield 24%; ¹H NMR (300 MHz, DMSO-d$_6$) δ ppm: 2.20 (s, 3H), 2.40 (br s, 4H), 2.60 (br s, 4H), 3.11 (s, 3H), 3.61 (s, 2H), 7.47 (t, J=9.1 Hz, 1H), 7.79 (m, 1H), 7.86 (s, 1H), 8.12 (dd, J=2.4, 6.8 Hz, 1H), 8.42 (s, 1H), 8.60 (s, 1H), 10.07 (s, 1H).

Example 68

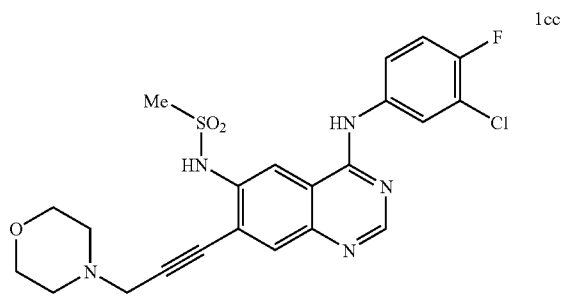

1cc

1cc: yield 45%; ¹H NMR (300 MHz, DMSO-d$_6$) δ ppm: 2.59 (m, 4H), 3.13 (s, 3H), 3.63 (m, 6H), 7.47 (t, J=9.1 Hz, 1H), 7.79 (m, 1H), 7.89 (s, 1H), 8.13 (dd, J=2.4, 6.8 Hz, 1H), 8.45 (s, 1H), 8.62 (s, 1H), 10.10 (s, 1H).

Example 69

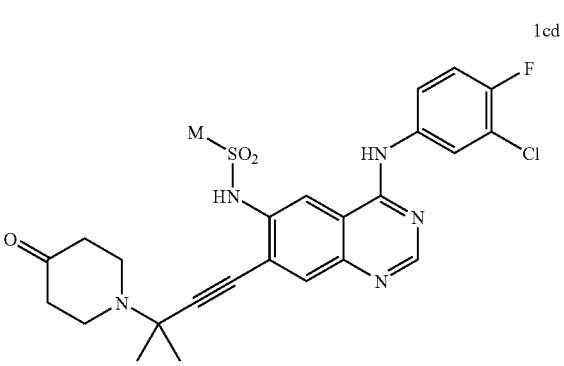

1cd

1cd: yield 32%; ¹H NMR (300 MHz, DMSO-d$_6$) δ ppm: 1.55 (s, 6H), 2.40 (m, 4H), 3.00 (m, 4H), 3.12 (s, 3H), 7.47 (t, J=9.0 Hz, 1H), 7.79 (m, 1H), 7.88 (s, 1H), 8.12 (br d, J=6.3 Hz, 1H), 8.45 (s, 1H), 8.62 (s, 1H), 10.10 (s, 1H).

Example 70

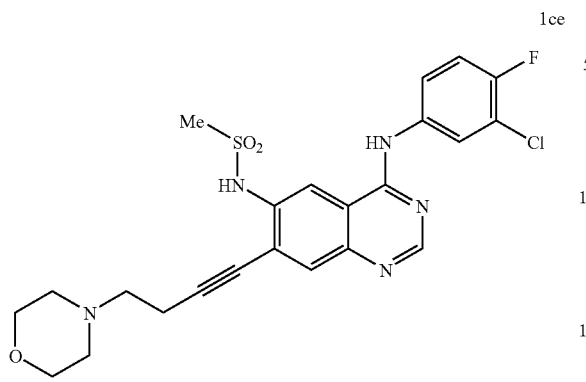

1ce

1ce: yield 49%; $^1$H NMR (300 MHz, DMSO-d$_6$) δ ppm: 2.25-2.80 (m, 8H), 3.11 (s, 3H), 3.58 (br s, 4H), 7.44 (t, J.=8.9 Hz, 1H), 7.79 (m, 2H), 8.11 (m, 2H), 8.43 (s, 1H), 8.58 (s, 1H), 10.06 (s, 1H).

Example 71

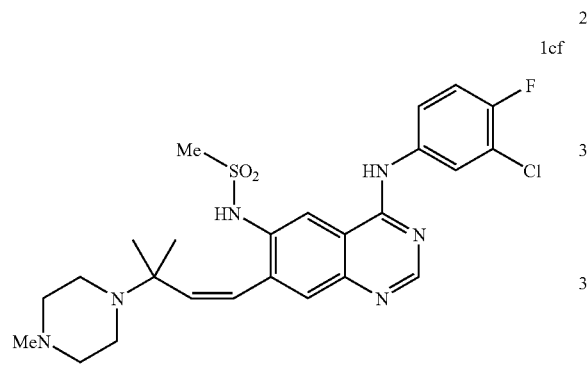

1cf

1cf: yield 54%; $^1$H NMR (300 MHz, DMSO-d$_6$) δ ppm: 1.02 (s, 6H), 2.05 (s, 3H), 2.18 (br s, 4H), 2.51 (br s, 4H), 3.06 (s, 3H), 5.89 (d, J=12.9 Hz, 1H), 6.67 (d, J=12.9 Hz, 1H), 7.47 (t, J=9.0 Hz, 1H), 7.81 (m, 1H), 7.95 (s, 1H), 8.14 (br d, J=6.5 Hz, 1H), 8.34 (s, 1H), 8.60 (s, 1H), 9.99 (s, 1H).

Example 72

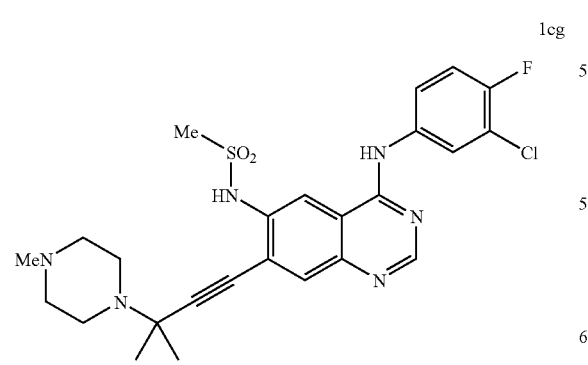

1cg

1cg: yield 62%; $^1$H NMR (270 MHz, DMSO-d$_6$) δ ppm: 1.46 (s, 6H), 2.20 (s, 3H), 2.43 (br s, 4H), 2.71 (br s, 4H), 3.10 (s, 3H), 7.46 (t, J=9.2 Hz, 1H), 7.79 (m, 1H), 7.82 (s, 1H), 8.13 (dd, J=2.4, 6.8 Hz, 1H), 8.41 (s, 1H), 8.60 (s, 1H), 10.06 (s, 1H).

Example 73

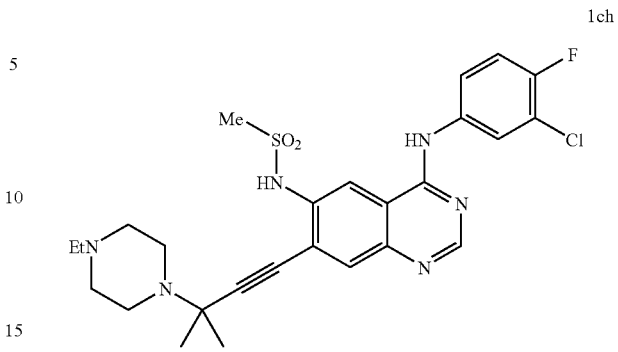

1ch

1ch: yield 29%; $^1$H NMR (270 MHz, DMSO-d$_6$) δ ppm: 1.01 (t, J=7.3 Hz, 3H), 1.46 (s, 6H), 2.35 (q, J=7.3 Hz, 2H), 2.50 (br s, 4H), 2.72 (br s, 4H), 3.09 (s, 3H), 7.46 (t, J=9.2 Hz, 1H), 7.81 (br s, 2H), 8.12 (dd, J=2.4, 6.5 Hz, 1H), 8.38 (s, 1H), 8.59 (s, 1H), 10.04 (s, 1H).

Example 74

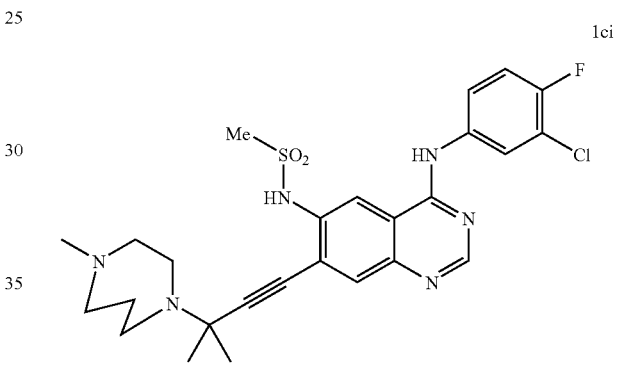

1ci

1ci: yield 56%; $^1$H NMR (270 MHz, DMSO-d$_6$) δ ppm: 1.45 (s, 6H), 1.82 (m, 2H), 2.36 (s, 3H), 2.70 (m, 4H), 2.91 (m, 4H), 3.06 (s, 3H), 7.45 (t, J=9.2 Hz, 1H), 7.77 (br s, 2H), 8.11 (br d, J=7.0 Hz, 1H), 8.29 (s, 1H), 8.55 (s, 1H), 9.98 (s, 1H).

Example 75

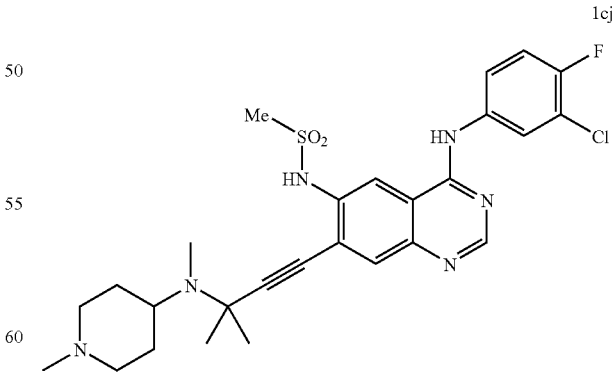

1cj

1cj: yield 46%; $^1$H NMR (270 MHz, DMSO-d$_6$) δ ppm: 1.49 (s, 6H), 1.71 (m, 4H), 2.03 (m, 2H), 2.19 (s, 3H), 2.34 (s, 3H), 2.85 (br d J=11.3 Hz, 2H), 3.00 (m, 1H), 3.07 (s, 3H), 7.46 (t, J=9.2 Hz, 1H), 7.73 (s, 1H), 7.80 (m, 1H), 8.12 (br d, J=6.8 Hz, 1H), 8.34 (s, 1H), 8.58 (s, 1H), 10.02 (s, 1H).

Example 7.6

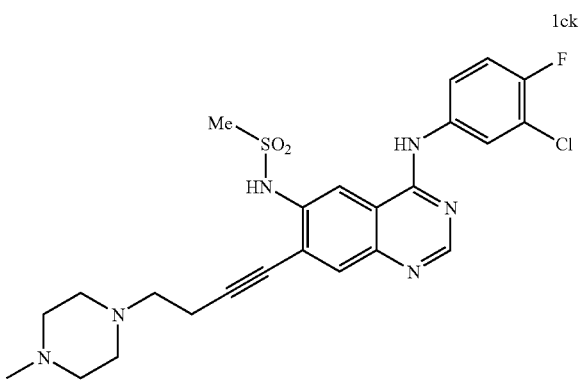

1ck: yield 24%; $^1$H NMR (270 MHz, DMSO-$d_6$) δ ppm: 2.17 (s, 3H), 2.36 (br s, 4H), 2.50 (br s, 4H), 2.69 (m, 4H), 3.10 (s, 3H), 7.46 (t, J=9.2 Hz, 1H), 7.80 (br s, 2H), 8.13 (dd, J=2.4, 6.8 Hz, 1H), 8.42 (s, 1H), 8.59 (s, 1H), 10.06 (s, 1H).

Example 77

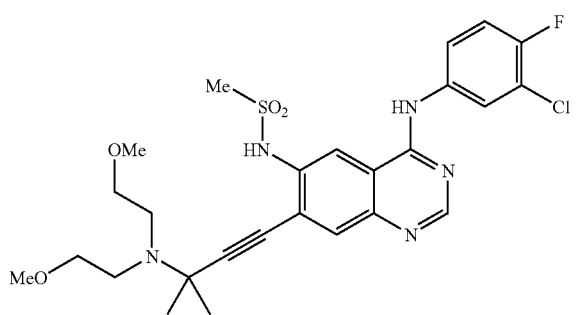

1cl: yield 31%; $^1$H NMR (270 MHz, DMSO-$d_6$) δ ppm: 1.47 (s, 6H), 2.87 (t, J=6.6 Hz, 4H), 3.11 (s, 3H), 3.26 (s, 6H), 3.25-3.51 (m, 4H), 7.47 (t, J=9.2 Hz, 1H), 7.80 (m, 1H), 7.84 (s, 1H), 8.13 (dd, J=2.7, 7.0 Hz, 1H), 8.45 (s, 1H), 8.62 (s, 1H), 9.40-9.60 (br s, 1H), 10.09 (s, 1H).

Example 78

1) Formamidine acetate (4.51 g, 43.3 mmol) and methoxyethanol (60 mL) were added to 5-bromo-4-nitroanthranyl acid (described in JP-A-2000-169451) (5.65 g, 21.7 mmol) and the mixture was refluxed for 4 hrs. Water was added until the reaction mixture becomes about 200 mL and the precipitate was filtered and washed with water. The precipitate was dried under reduced pressure to give 6-bromo-7-nitro-3H-quinazolin-4-one (5.21 g, 64%). To a solution (20 mL) of 6-bromo-7-nitro-3H-quinazolin-4-one (1.34 g, 5.0 mmol) in toluene were added phosphorous oxychloride (0.70 mL, 7.5 mmol) and diisopropylethylamine (1.29 mL, 7.5 mmol), and the mixture was stirred at 80° C. for 5 hrs. A solution (5 mL) of 3-chloro-4-fluoroaniline (1.09 g, 7.5 mmol) in isopropanol was added at room temperature, and the mixture was stirred overnight. The reaction mixture was poured into hexane (30 mL) and the mixture was stirred at room temperature for 30 min. The product was collected by filtration and dried. To this compound were added reduced iron (1.10 g, 20.0 mmol), 1N hydrochloric acid (10 mL) and ethanol (30 mL) and the mixture was refluxed for 1 hr. 1N Aqueous sodium hydroxide solution (10 mL) was added and the mixture was stirred at 50° C. for 30 min. Saturated brine was added and the mixture was extracted with ethyl acetate. The organic layer was concentrated and the residue was suspension-washed with acetonitrile (10 mL) to give 6-bromo-N$^4$-(3-chloro-4-fluorophenyl)-4,7-quinazolinediamine (5') (987 mg, 54%).

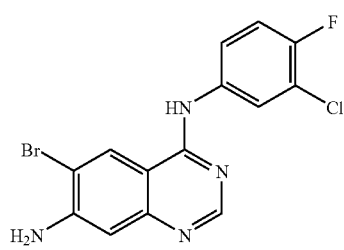

5': $^1$H NMR (300 MHz, DMSO-$d_6$) δ ppm: 6.24 (br s, 2H), 7.00 (s, 1H), 7.42 (br t, 1H), 7.79 (br s, 1H), 8.17 (br s, 1H), 8.43 (s, 1H), 8.68 (s, 1H), 9.64 (s, 1H).

2) Using this compound 5' and compound 4a and in the same manner as in Example 3, N$^4$-(3-chloro-4-fluorophenyl)-6-[3-methyl-3-(4-methyl-1-piperazinyl)-1-butynyl]-4,7-quinazolinediamine (2a') (yield 68%) was obtained.

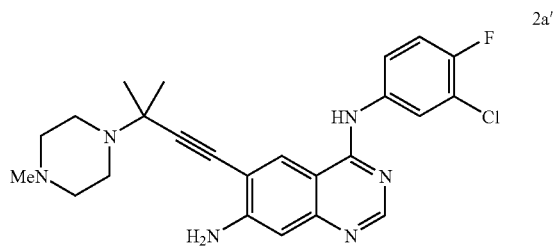

2a': $^1$H NMR (300 MHz, DMSO-$d_6$) δ ppm: 1.47 (s, 6H), 2.67 (s, 3H), 5.99 (s, 1H), 6.90 (s, 1H), 7.38 (t, J=9.2 Hz, 1H), 7.80 (m, 1H), 8.15 (dd, J=2.6, 6.8 Hz, 1H), 8.37 (s, 1H), 8.44 (s, 1H), 9.65 (br s, 1H).

3) To a solution (4 mL) of 2a' (200 mg, 0.44 mmol) in pyridine was added methanesulfonyl chloride (80 µL, 1.0 mmol) and the mixture was stirred at room temperature for 4.5 hrs. Then, methanesulfonyl chloride (80 µL, 1.0 mmol) was added. After stirring overnight, methanesulfonyl chloride (80 µL, 1.0 mmol) was further added, and 6 hrs later, the mixture was concentrated. Water was added and the mixture was extracted with ethyl acetate (30 mL×2), dried and concentrated. The obtained solid was suspension-washed with acetonitrile, and collected by filtration to give compound 1cg' (145 mg, 55%).

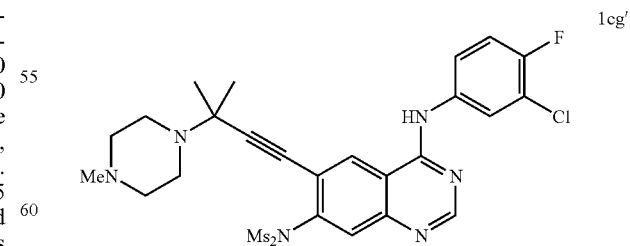

1cg': TOF Mass: m/z=609 [M+1];
$^1$H NMR (300 MHz, DMSO-$d_6$) δ ppm: 1.41 (s, 6H), 2.11 (s, 3H), 2.33 (br s, 4H), 2.66 (br s, 4H), 3.61 (s, 6H), 7.46 (t, J=9.1 Hz, 1H), 7.78 (m, 1H), 8.02 (s, 1H), 8.11 (m, 1H), 8.66 (s, 1H), 8.74 (s, 1H), 10.20 (br s, 1H).

Example 79

A solution of amino compound 2a (453 mg, 1.00 mmol) obtained by the method of Synthetic Example 2, 3-methylthiopropionic acid chloride (152 mg, 1.20 mmol) and triethylamine (167 μL, 1.20 mmol) in DMF (4.5 mL) was stirred at room temperature for 19 hrs and then at 40° C. for 6 hrs. The reaction mixture was poured into aqueous sodium hydrogen carbonate (100 mL) and the mixture was extracted with ethyl acetate (100 mL×2). The obtained organic layer was washed with saturated brine (100 mL×2) and dried over anhydrous sodium sulfate. The solvent was evaporated under reduced pressure. The residue was subjected to silica gel column chromatography (methylene chloride-methanol) and recrystallized from ethyl acetate to give the objective coupling compound 1af (120 mg, 22%).

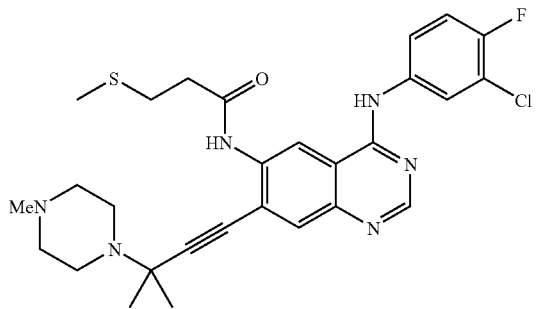

1af

1af: $^1$H NMR (300 MHz, DMSO-d$_6$) δ ppm: 1.46 (s, 6H), 2.12 (s, 3H), 2.17 (s, 3H), 2.38 (br s, 4H), 2.67 (br s, 4H), 2.74-2.83 (m, 4H), 7.46 (t, J=9.0 Hz, 1H), 7.80-7.85 (m, 2H), 8.17 (dd, J=6.9, 2.4 Hz, 1H), 8.62 (br s, 2H), 9.66 (s, 1H), 10.03 (s, 1H).

Example 80

A solution of amino compound 2a (452 mg, 1.00 mmol) obtained by the method of Synthetic Example 2, tetronic acid (126 mg, 1.50 mmol), sodium hydrogen carbonate (423 mg, 5.00 mmol) and HATU (701 mg, 1.84 mmol) in DMF (1.0 mL) was stirred at room temperature for 20 hrs. The reaction mixture was poured into aqueous sodium hydrogen carbonate (100 mL) and the mixture was extracted with ethyl acetate (50 mL×2). The obtained organic layer was washed with saturated brine (50 mL×2) and dried over anhydrous sodium sulfate. The solvent was evaporated under reduced pressure and the residue was subjected to silica gel column chromatography (methylene chloride-methanol), and suspension-washed with ethyl acetate to give the objective coupling compound 1ag (71 mg, 14%).

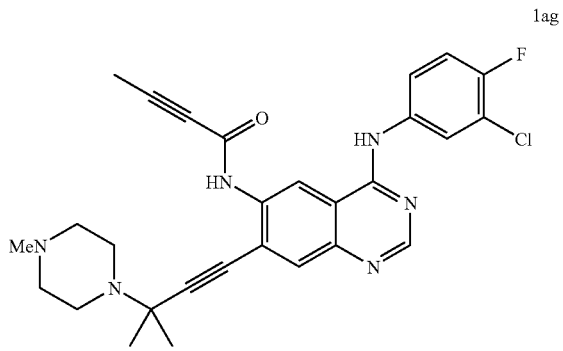

1ag

1ag: $^1$H NMR (300 MHz, DMSO-d$_6$) δ ppm: 1.45 (s, 6H), 2.06 (s, 3H), 2.15 (s, 3H), 2.37 (br s, 4H), 2.67 (br s, 4H), 7.46 (t, J=9.0 Hz, 1H), 7.81-7.85 (m, 2H), 8.19 (dd, J=6.3, 1.8 Hz, 1H), 8.54 (s, 1H), 8.63 (s, 1H), 9.98 (s, 1H), 10.26 (s, 1H).

Example 81

A solution of amino compound 2a (452 mg, 1.00 mmol) obtained by the method of Synthetic Example 2, and ketene dimer (220 mg, 2.61 mmol) in toluene (15 mL) were refluxed at room temperature for 1.5 hrs. The reaction mixture was concentrated and subjected to silica gel column chromatography (methylene chloride-methanol) to give the objective coupling compound 1ah (110 mg, 20%).

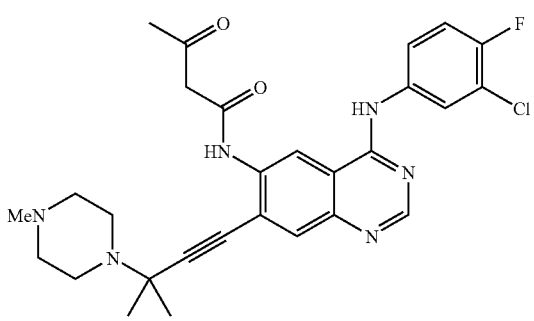

1ah

1ah: $^1$H NMR (300 MHz, DMSO-d$_6$) δ ppm: 1.46 (s, 6H), 2.21 (s, 3H), 2.27 (s, 3H), 2.44 (br s, 4H), 2.67 (br s, 4H), 3.17 (s, 2H), 7.45 (t, J=9.3 Hz, 1H), 7.78-7.83 (m, 2H), 8.14 (dd, J=6.9, 2.4 Hz, 1H), 8.60 (s, 1H), 8.71 (s, 1H), 9.93 (s, 1H), 10.01 (s, 1H).

Example 82

A solution of amino compound 2a (452 mg, 1.00 mmol) obtained by the method of Synthetic Example 2, cyanoacetic acid (425 mg, 5.00 mmol), triethylamine (209 μL, 1.50 mmol) and EDC (288 mg, 1.5 mmol) in DMF (5.0 mL) was stirred at room temperature for 14 hrs. The reaction mixture was poured into aqueous sodium hydrogen carbonate (100 mL) and extracted with ethyl acetate (50 mL×2). The obtained organic layer was washed with saturated brine (50 mL×2) and dried over anhydrous sodium sulfate. The solvent was evaporated under reduced pressure. The residue was subjected to silica gel column chromatography (methylene chloride-methanol) and further recrystallized from methanol to give the objective coupling compound 1ai (189 mg, 37%).

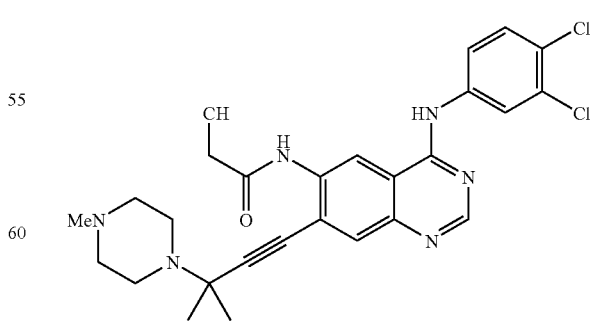

1ai

1ai: $^1$H NMR (300 MHz, DMSO-d$_6$) δ ppm: 1.46 (s, 6H), 2.34 (s, 3H), 2.64 (br s, 4H), 2.74 (br s, 4H), 4.14 (s, 2H), 7.46 (t, J=9.0 Hz, 1H), 7.80-7.86 (m, 2H), 8.19 (dd, J=6.6, 2.1 Hz, 1H), 8.59 (s, 1H), 8.64 (s, 1H), 10.10 (s, 1H), 10.31 (s, 1H).

Example 83

A solution of amino compound 2a (905 mg, 2.00 mmol) obtained by the method of Synthetic Example 2 and 2-chloroethanesulfonyl chloride (840 μL, 8.00 mmol) in pyridine (5.0 mL) was stirred at room temperature for 1 hr. The reaction mixture was poured into saturated brine (200 mL) and extracted with ethyl acetate (200 mL×2). The obtained organic layer was washed with saturated brine (300 mL×3) and dried over anhydrous sodium sulfate. The solvent was evaporated under reduced pressure. The residue was subjected to silica gel column chromatography (methylene chloride-methanol) and further subjected to pTLC (methylene chloride-methanol) to give the objective coupling compound 1aj (9 mg, 0.8%).

1aj: $^1$H NMR (300 MHz, DMSO-d$_6$) δ ppm: 1.46 (s, 6H), 2.29 (s, 3H), 2.55 (br s, 4H), 2.77 (br s, 4H), 5.75 (s, 1H), 5.91 (d, j=9.9 Hz, 1H), 6.01 (d, J=16.5 Hz, 1H), 6.85 (dd, J=16.4, 9.9 Hz), 7.45 (t, J=9.1 Hz, 1H), 7.74-7.83 (m, 2H), 8.13 (dd, J=6.8, 2.2 Hz, 1H), 8.35 (s, 1H), 8.57 (s, 1H), 10.00 (s, 1H).

Examples 84-87

Using mixtures (about 3:1) of 7-bromo-6-nitro-3H-quinazolin-4-one and 7-bromo-8-nitro-3H-quinazolin-4-one and various anilines as starting materials and according to the method of Synthetic Example 2-1), the method of Example 3-1) (simultaneously using compound 4a), the method of Synthetic Example 5, and the method of Example 3-2), compounds 1ak-1an were synthesized (Scheme 6).

Scheme 6

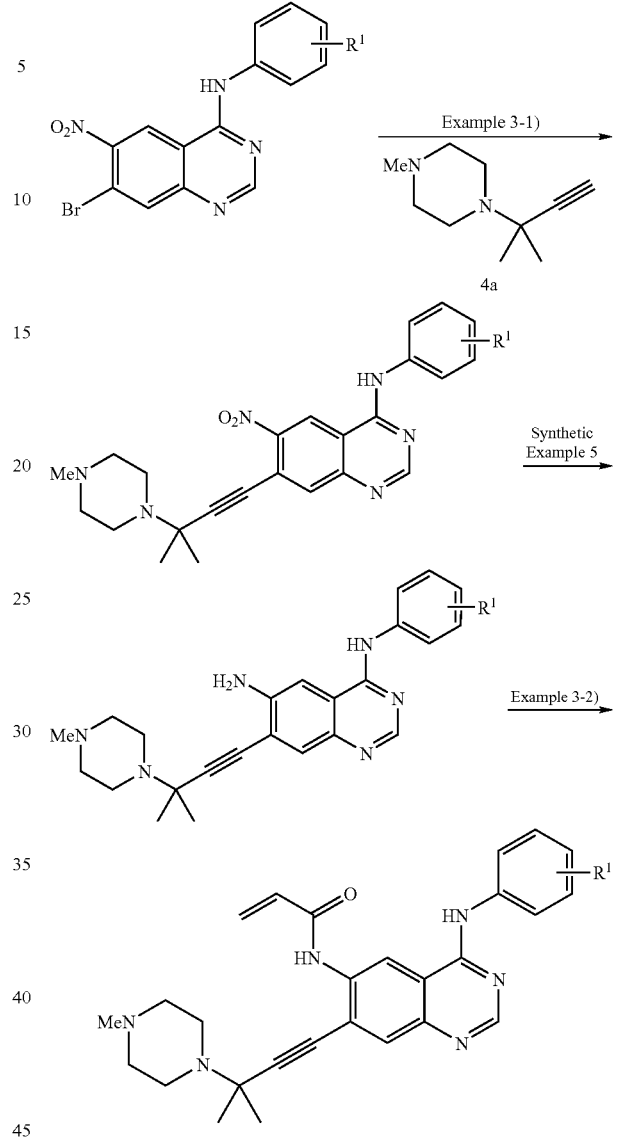

wherein R$^1$ denotes a substituent such as m-OMe, m-CN, p-NMe$_2$, m-Me and the like.

Example 84

Using 3-methoxyaniline as aniline, the compound was converted to the objective compound 1ak (yield 40%).

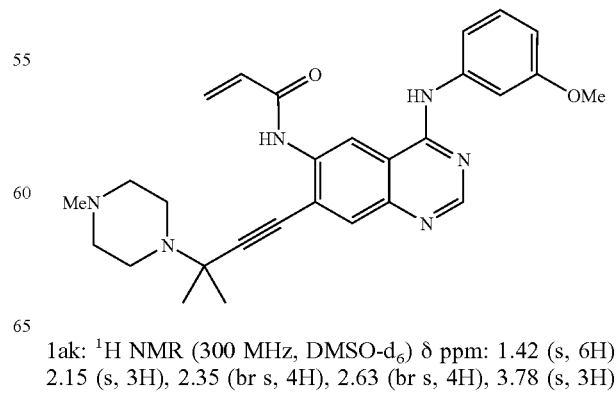

1ak: $^1$H NMR (300 MHz, DMSO-d$_6$) δ ppm: 1.42 (s, 6H), 2.15 (s, 3H), 2.35 (br s, 4H), 2.63 (br s, 4H), 3.78 (s, 3H), 5.83 (dd, J=10.3, 1.7 Hz, 1H), 6.32 (dd, J=17.0, 1.7 Hz, 1H), 6.57 (dd, J=17.0, 10.1 Hz, 1H), 6.72 (dd, J=7.8, 2.2 Hz, 1H), 7.29 (t, J=8.2 Hz, 1H), 7.48-7.55 (m, 2H), 7.81 (s, 1H), 8.60 (s, 1H), 8.71 (s, 1H), 9.81 (s, 1H), 9.83 (s, 1H).

Example 85

Using 3-aminobenzonitrile as aniline, the compound was converted to the objective compound 1al (yield 11%).

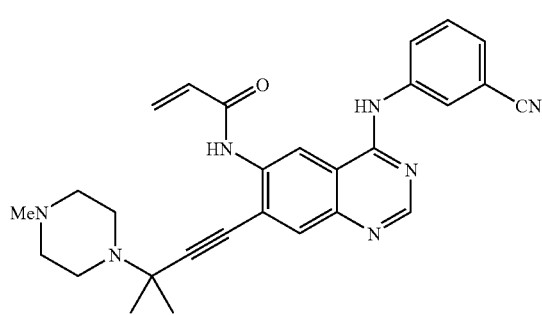

1al

1al: $^1$H NMR (300 MHz, DMSO-$d_6$) δ ppm: 1.43 (s, 6H), 2.14 (s, 3H), 2.34 (br s, 4H), 2.63 (br s, 4H), 5.84 (dd, J=10.3, 1.5 Hz, 1H), 6.33 (dd, J=17.1, 1.5 Hz, 1H), 6.58 (dd, J=17.0, 10.1 Hz, 1H), 7.57-7.64 (m, 2H), 7.85 (s, 1H), 8.16 (d, J=7.1 Hz, 1H), 8.42 (s, 1H), 8.67 (s, 1H), 8.71 (s, 1H), 9.88 (s, 1H), 10.12 (s, 1H).

Example 86

Using N,N'-dimethylbenzene-1,4-diaminobenzene as aniline, the compound was converted to the-objective compound 1am (yield 72%).

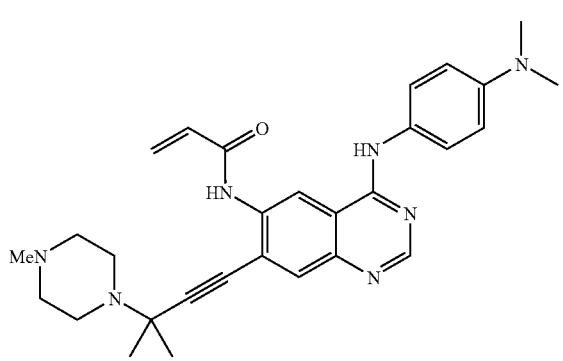

1am

1am: $^1$H NMR (270 MHz, DMSO-$d_6$) δ ppm: 1.42 (s, 6H), 2.14 (s, 3H), 2.35 (br s, 4H), 2.63 (br s, 4H), 2.90 (s, 6H), 5.82 (br d, J=10.0 Hz, 1H), 6.31 (br d, J=17.0 Hz, 1H), 6.57 (dd, J=17.0, 10.0 Hz, 1H), 6.76 (d, J=9.2 Hz, 2H), 7.56 (d, J=9.2 Hz, 2H), 7.75 (s, 1H), 8.46 (s, 1H), 8.63 (s, 1H), 9.70 (s, 1H), 9.82 (s, 1H).

Example 87

Using m-tolylamine as aniline, the compound was converted to the objective compound 1an (yield 63%).

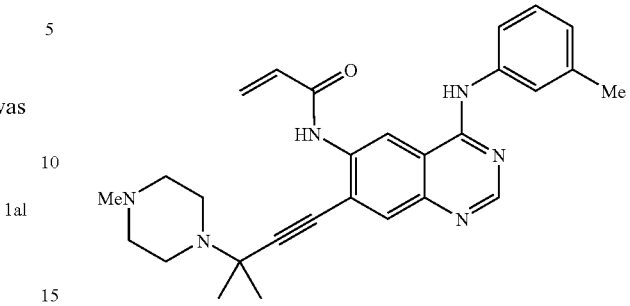

1an

1an: $^1$H NMR (270 MHz, DMSO-$d_6$) δ ppm: 1.42 (s, 6H), 2.14 (s, 3H), 2.34 (br s, 7H), 2.62 (br s, 4H), 5.83 (dd, J=10.0, 1.9 Hz, 1H), 6.31 (dd, J=17.3, 1.9 Hz, 1H), 6.58 (dd, J=17.3, 10.0 Hz, 1H), 6.96 (d, J=7.0 Hz, 1H), 7.27 (m, 1H), 7.63 (br s, 2H), 7.80 (s, 1H), 8.57 (s, 1H), 8.70 (s, 1H), 9.81 (s, 1H), 9.84 (s, 1H).

Example 88

To the triflate compound 6e (1.00 g, 2.15 mmol) prepared in Synthetic Example 17 were added compound 4b (395 mg, 2.58 mmol), triethylamine (16 mL) and DMF (4 mL), and the mixture was repeatedly subjected to the step of degassing and displacement with nitrogen. Palladium (II) acetate (48.2 mg) and triphenylphosphine (67.9 mg) were added. The mixture was stirred at 80° C. for 5 hrs and concentrated under reduced pressure. 5% Aqueous sodium hydrogen carbonate and saturated brine were added to the residue and the mixture was extracted with ethyl acetate. After drying and concentration, the residue was purified [silica gel column chromatography, suspension-washed with ethanol-water, and recrystallized from THF-water] to give the objective coupling compound 1bk (434 mg, 43%) as colorless crystals.

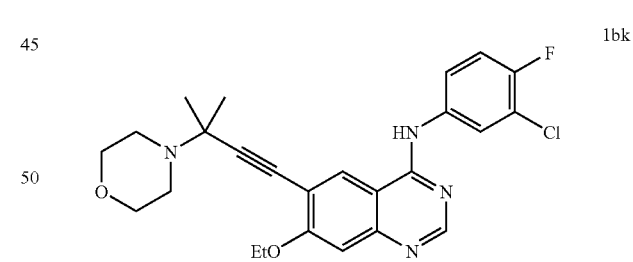

1bk

1bk: $^1$H NMR (270 MHz, CDCl$_3$) δ ppm: 1.51 (s, 6H), 1.53 (t, J=7.0 Hz, 3H), 2.80 (m, 4H), 3.80 (m, 4H), 4.18 (q, J=7.0 Hz, 2H), 7.17 (s, 1H), 7.17 (t, J=8.8 Hz, 1H), 7.40 (br s, 1H), 7.54 (m, 1H), 7.92 (s, 1H), 7.95 (dd, J=2.6, 6.3 Hz, 1H), 8.68 (s, 1H).

Examples 89-111

Using triflate compound 6e and various compounds 4, and in the same manner as in Example 88, compounds 1 bi-1bah were synthesized. The structure, yield and spectrum data of the compounds are shown in the following.

Example 89

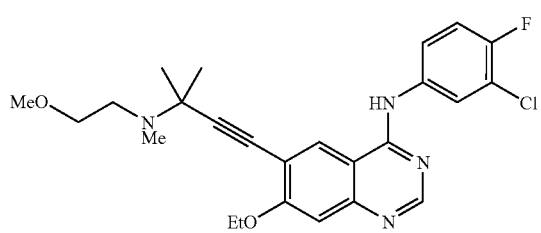

1bl (yield 70%): ¹H NMR (270 MHz, CDCl₃) δ ppm: 1.51 (s, 6H), 1.51 (t, J=7.0 Hz, 3H), 2.43 (s, 3H), 2.82 (t, J=6.1 Hz, 2H), 3.39 (s, 3H), 3.54 (t, J=6.1 Hz, 2H), 4.17 (q, J=7.0 Hz, 2H), 7.15 (s, 1H), 7.16 (t, J=8.8 Hz, 1H), 7.52 (br s, 1H), 7.56 (m, 1H), 7.92 (s, 1H), 7.95 (dd, J=2.7, 6.5 Hz, 1H), 8.66 (s, 1H).

Example 90

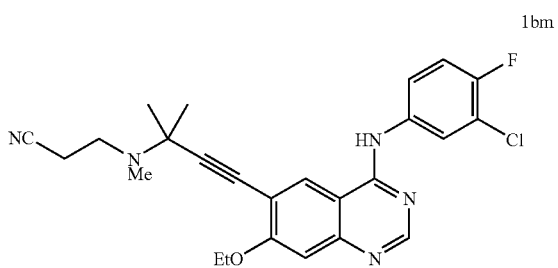

1bm (yield 53%): ¹H NMR (270 MHz, CDCl₃) δ ppm: 1.51 (s, 6H), 1.53 (t, J=6.9 Hz, 3H), 2.42 (s, 3H), 2.59 (t, J=6.5 Hz, 2H), 3.01 (t, J=6.5 Hz, 2H), 4.21 (q, J=6.9 Hz, 2H), 7.16 (t, J=8.8 Hz, 1H), 7.18 (s, 1H), 7.54 (br s, 1H), 7.56 (m, 1H), 8.00 (dd, J=2.6, 6.3 Hz, 1H), 8.12 (s, 1H), 8.67 (s, 1H).

Example 91

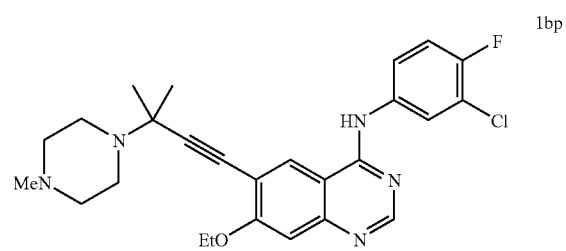

1bn (yield 55%): ¹H NMR (270 MHz, CDCl₃) δ ppm: 1.40-1.60 (m, 11H), 1.60-1.75 (m, 4H), 2.74 (m, 4H), 4.19 (q, J=6.9 Hz, 2H), 7.17 (t, J=8.6 Hz, 1H), 7.17 (s, 1H), 7.34 (br s, 1H), 7.52 (m, 1H), 7.91 (br s, 1H), 7.95 (dd, J=2.7, 6.5 Hz, 1H), 8.67 (s, 1H).

Example 92

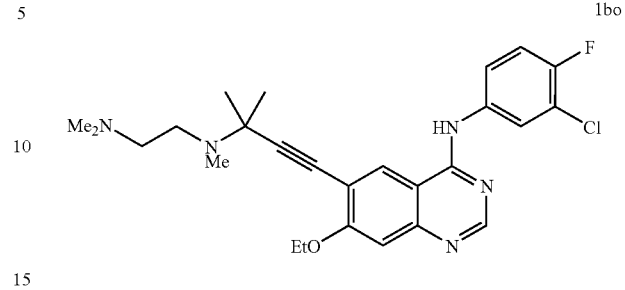

1bo.nHCl [1bo was converted to its hydrochloride with hydrochloric acid/ethyl acetate (3 equivalent amount) in methanol-ethyl acetate (1:2)] (yield 41% when n=3): ¹H NMR (270 MHz, CDCl₃) δ ppm: 1.48 (t, J=6.9 Hz, 3H), 1.82 (br s, 6H), 2.89 (s, 6H), 2.92 (br s, 3H), 3.70 (br s, 1H), 4.30 (q, J=6.9 Hz, 2H), 7.47 (s, 1H), 7.55 (t, J=9.0 Hz, 1H), 7.83 (m, 1H), 8.11 (dd, J=2.6, 2.7 Hz, 1H), 8.94 (s, 1H), 9.52 (br s, 1H).

Example 93

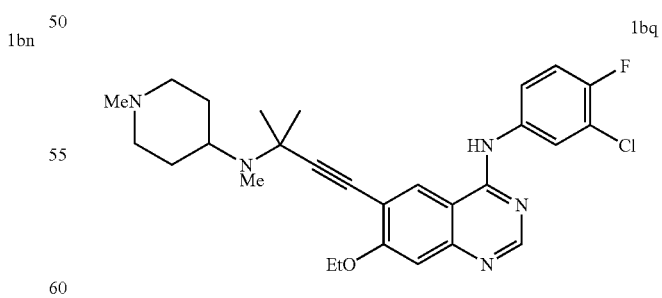

1bp (yield 48%): ¹H NMR (270 MHz, DMSO-d₆) δ ppm: 1.43-1.47 (m, 3H), 1.43 (s, 6H), 2.15 (s, 3H), 2.37 (br s, 4H), 2.71 (br s, 4H), 4.21 (q, J=6.8 Hz, 2H), 7.17 (s, 1H), 7.44 (t, J=9.2 Hz, 1H), 7.82 (m, 1H), 8.20 (dd, J=2.7, 7.0 Hz, 1H), 8.55 (s, 1H), 8.56 (s, 1H), 9.84 (s, 1H).

Example 94

1bq (yield 23%): ¹H NMR (270 MHz, CDCl₃) δ ppm: 1.52 (t, J=7.0 Hz, 3H), 1.55 (s, 6H), 1.79 (m, 4H), 1.97 (m, 2H), 2.25 (s, 3H), 2.45 (s, 3H), 2.90 (m, 2H), 3.01 (m, 1H), 4.19 (q, J=7.0 Hz, 2H), 7.17 (t, J=8.8 Hz, 1H), 7.17 (s, 1H), 7.36 (br s, 1H), 7.53 (m, 1H), 7.86 (s, 1H), 7.94 (dd, J=2.7, 6.5 Hz, 1H), 8.67 (s, 1H).

Example 95

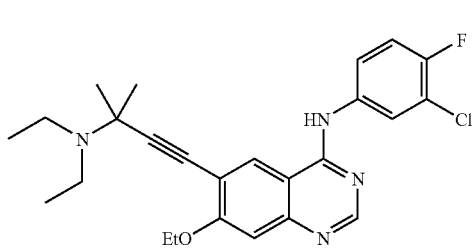

1br (yield 55%): $^1$H NMR (270 MHz, CDCl$_3$) δ ppm: 1.00-1.20 (m, 6H), 1.40-1.60 (m, 9H), 2.80 (q, J=7.0 Hz, 4H), 4.18 (q, J=7.0 Hz, 2H), 7.16 (t, J=8.8 Hz, 1H), 7.16 (s, 1H), 7.38 (br s, 1H), 7.51 (m, 1H), 7.88 (s, 1H), 7.94 (dd, J=2.7, 6.5 Hz, 1H), 8.66 (s, 1H).

Example 96

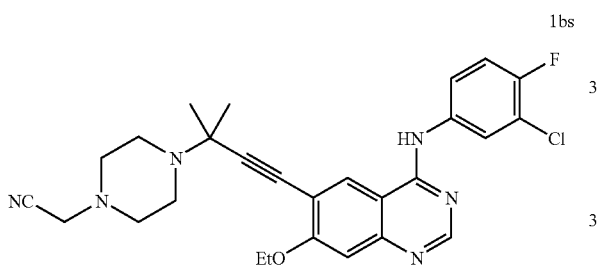

1bs (yield 31%): $^1$H NMR (270 MHz, CDCl$_3$) δ ppm: 1.53 (s, 6H), 1.53 (t, J=7.0 Hz, 3H), 2.73(m, 4H), 2.88 (m, 4H), 3.53 (s, 2H), 4.19 (q, J=7.0 Hz, 2H), 7.13 (t, J=8.9 Hz, 1H), 7.13 (s, 1H), 7.39 (br s, 1H), 7.53 (m, 1H), 7.93 (s, 1H), 7.95 (dd, J=2.7, 6.8 Hz, 1H), 8.67 (s, 1H).

Example 97

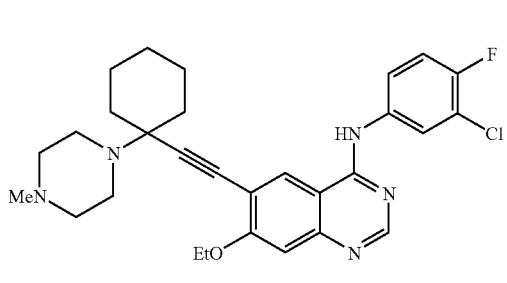

1bt (yield 14%): $^1$H NMR (270 MHz, CDCl$_3$) δ ppm: 1.26 (m, 1H), 1.50 (m, 2H), 1.53 (t, J=7.0 Hz, 3H), 1.77(m, 5H), 2.17 (m, 2H), 2.32 (s, 3H), 2.57(br s, 4H), 2.88(br s, 4H), 4.19 (q, J=7.0 Hz, 2H), 7.15 (s, 1H), 7.17 (t, J=8.9 Hz, 1H), 7.65 (m, 1H), 8.01 (m, 2H), 8.17 (s, 1H), 8.65 (s, 1H).

Example 98

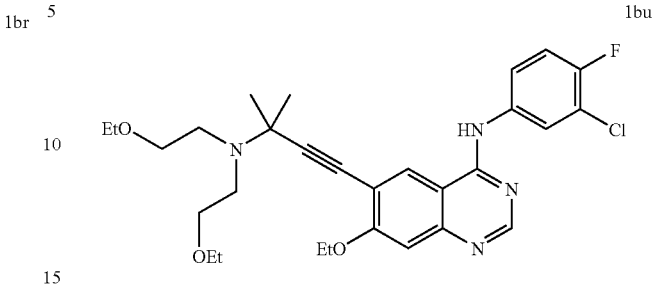

1bu (yield 48%): $^1$H NMR (270 MHz, CDCl$_3$) δ ppm: 1.52 (s, 6H), 1.52 (t, J=7.0 Hz, 3H), 2.96 (t, J=6.8 Hz, 4H), 3.37(s, 6H), 3.51 (t, J=6.8 Hz, 4H), 4.18 (q, J=7.0 Hz, 2H), 7.16 (s, 1H), 7.17 (t, J=8.9 Hz, 1H), 7.44 (br s, 1H), 7.56 (m, 1H), 7.90 (s, 1H), 7.96 (dd, J=2.7, 6.8 Hz, 1H), 8.66 (s, 1H).

Example 99

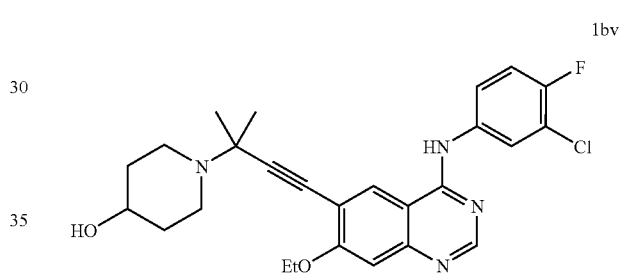

1bv (yield 23%): $^1$H NMR (270 MHz, DMSO-d$_6$) δ ppm: 1.44 (m, 11H), 1.77 (m, 2H), 2.35 (m, 2H), 2.99 (m, 2H), 3.40-3.50 (m, 1H), 4.21 (q, J=7.0 Hz, 2H), 4.58 (d, J=4.3 Hz, 1H), 7.17 (s, 1H), 7.43 (t, J=9.2 Hz, 1H), 7.84 (m, 1H), 8.20 (dd, J=2.7, 6.8 Hz, 1H), 8.54 (s, 1H), 8.56 (s, 1H), 9.83 (s, 1H).

Example 100

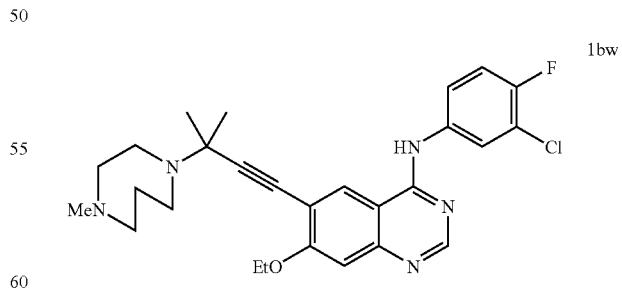

1bw (yield 50%): $^1$H NMR (270 MHz, CDCl$_3$) δ ppm: 1.50 (s, 6H), 1.52 (t, J=6.8 Hz, 3H), 1.88 (m, 2H), 2.37 (s, 3H), 2.65(m, 4H), 2.97 (m, 4H), 4.18 (q, J=6.8 Hz, 2H), 7.15 (s, 1H), 7.16 (t, J=8.9 Hz, 1H), 7.56 (m, 1H), 7.72 (br s, 1H), 7.96 (dd, J=2.7, 6.8 Hz, 1H), 8.01 (s, 1H), 8.65 (s, 1H).

Example 101

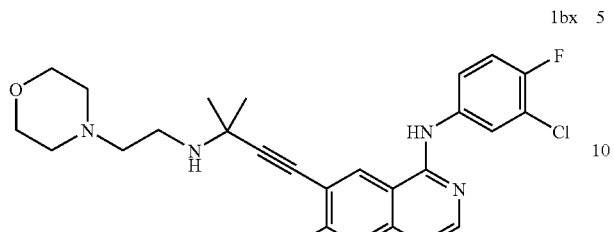

1bx (yield 59%): ¹H NMR (270 MHz, CDCl₃) δ ppm: 1.51 (s, 6H), 1.53 (t, J=7.0 Hz, 3H), 2.49 (m, 4H), 2.58 (t, J=6.1 Hz, 2H), 2.99 (t, J=6.1 Hz, 2H), 3.68 (m, 4H), 4.20 (q, J=7.0 Hz, 2H), 7.17 (t, J=8.9 Hz, 1H), 7.18 (s, 1H), 7.48 (br s, 1H), 7.54 (m, 1H), 7.92 (s, 1H), 7.94 (dd, J=2.7, 6.8 Hz, 1H), 8.68 (s, 1H).

Example 102

1by (yield 76%): ¹H NMR (270 MHz, CDCl₃) δ. ppm: 1.23 (t, J=7.0 Hz, 6H), 1.50 (t, J=7.0 Hz, 3H), 2.29 (s, 3H), 2.50-2.60 (br s, 4H), 2.89 (br s, 4H), 3.57-3.82 (m, 8H), 4.16 (q, J=7.0 Hz, 2H), 7.11 (s, 1H), 7.15(t, J=8.9 Hz, 1H), 7.62 (m, 1H), 7.99 (dd, J=2.7, 6.8 Hz, 1H), 8.27 (s, 1H), 8.30 (s, 1H), 8.62 (s, 1H).

Example 103

1bz (yield 64%): ¹H NMR (270 MHz, CDCl₃) δ ppm: 1.14 (t, J=7.0 Hz, 3H), 1.52 (s, 6H), 1.53 (t, J=7.0 Hz, 3H), 2.46 (q, J=7.0 Hz, 2H), 2.50-2.60 (br s, 4H), 2.88 (br s, 4H), 4.19 (q, J=7.0 Hz, 2H), 7.14 (s, 1H), 7.16(t, J=8.9 Hz, 1H), 7.67 (m, 1H), 8.00 (dd, J=2.7, 6.5 Hz, 1H), 8.17 (s, 1H), 8.24 (s, 1H), 8.64 (s, 1H).

Example 104

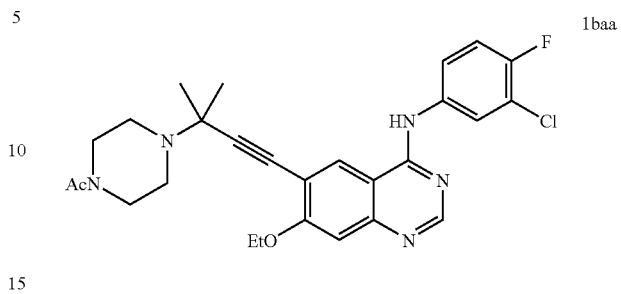

1baa (yield 76%): ¹H NMR (270 MHz, CDCl₃) δ ppm: 1.49 (t, J=7.0 Hz, 3H), 1.51 (s, 6H), 2.10 (s, 3H),2.74 (m, 4H), 3.53 (m, 2H), 3.68 (m, 2H), 4.14 (q, J=7.0 Hz, 2H), 7.15 (s, 1H), 7.16(t, J=8.9 Hz, 1H), 7.58 (m, 1H), 7.92 (br s, 1H), 7.96 (dd, J=2.4, 6.5 Hz, 1H), 7.98 (s, 1H), 8.66 (s, 1H).

Example 105

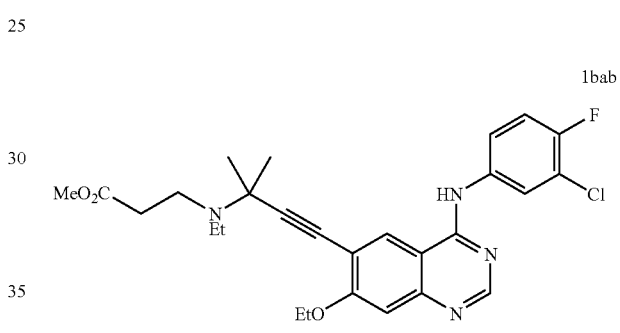

1bab (yield 47%): ¹H NMR (270 MHz, CDCl₃) δ ppm: 1.14 (t, J=7.0 Hz, 3H), 1.50 (s, 6H), 1.52 (t, J=7.0 Hz, 3H), 2.68 (m, 2H), 2.75 (q, J=7.0 Hz, 2H), 3.13 (m., 2H), 3.71 (s, 3H), 4.19 (q, J=7.0 Hz, 2H), 7.16 (s, 1H), 7.16(t, J=8.9 Hz, 1H), 7.68 (m, 1H), 7.79 (br s, 1H), 7.98 (dd, J=2.7, 6.5 Hz, 1H), 8.10 (s, 1H), 8.67 (s, 1H).

Example 106

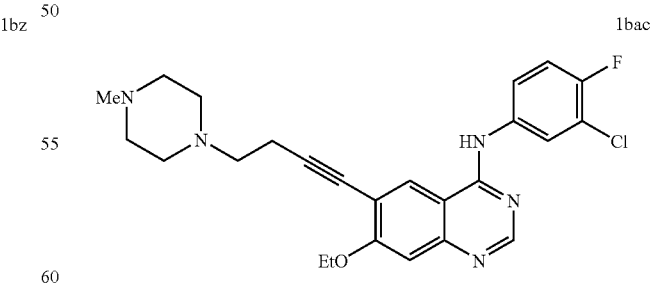

1bac (yield 8%): ¹H NMR (270 MHz, CDCl₃) δ ppm: 1.53 (t, J=7.0 Hz, 3H), 2.30 (s, 3H), 2.49 (br s, 4H), 2.64 (br s, 4H), 2.73 (m, 4H), 4.21 (q, J=7.0 Hz, 2H), 7.16 (s, 1H), 7.17(t, J=8.8 Hz, 1H), 7.54 (m, 1H), 7.58 (br s, 1H), 7.95 (dd, J=2.7, 6.5 Hz, 1H), 7.97 (s, 1H), 8.65 (s, 1H).

Example 107

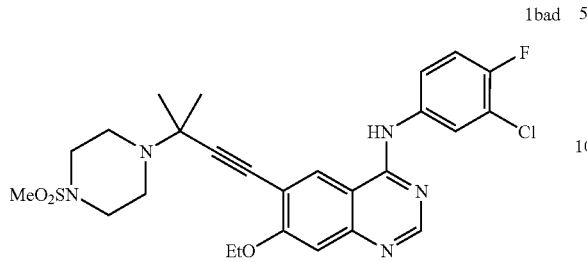

1bad (yield 65%): $^1$H NMR (270 MHz, DMSO-d$_6$) δ ppm: 1.44 (t, J=7.0 Hz, 3H), 1.47 (s, 6H), 2.83 (br s, 4H), 2.89 (s, 3H), 3.17 (br s, 4H), 4.22 (q, J=7.0 Hz, 2H), 7.18 (s, 1H), 7.44 (t, J=9.2 Hz, 1H), 7.82 (m, 1H), 8.20 (dd, J=2.7, 6.8 Hz, 1H), 8.57 (s, 2H), 9.83 (s, 1H).

Example 108

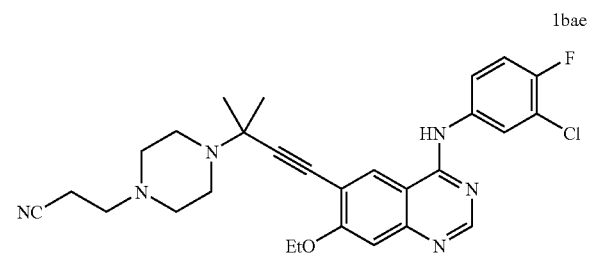

1bae (yield 39%): $^1$H NMR (270 MHz, DMSO-d$_6$) δ ppm: 1.44 (s, 6H), 1.46 (t, J=7.0 Hz, 3H), 2.50 (br s, 4H), 2.54 (t, J=5.9 Hz, 2H), 2.67 (t, J=5.9 Hz, 2H), 2.73 (br s, 4H), 4.21 (q, J=7.0 Hz, 2H), 7.18 (s, 1H), 7.44 (t, J=9.1 Hz, 1H), 7.82 (m, 1H), 8.20 (dd, J=2.7, 6.8 Hz, 1H), 8.57 (s, 2H), 9.84 (s, 1H).

Example 109

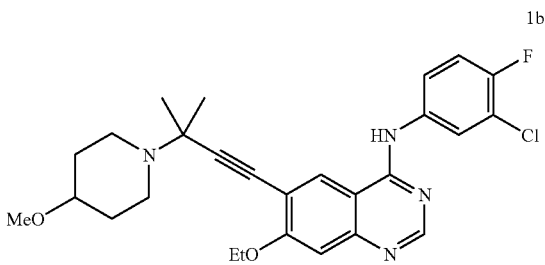

1baf (yield 49%): $^1$H NMR (270 MHz, DMSO-d$_6$) δ ppm: 1.45 (m, 11H), 1.89 (m, 2H), 2.40 (m, 2H), 2.98 (m, 2H), 3.16 (m, 1H), 3.23 (s, 3H), 4.22 (q, J=7.0 Hz, 2H), 7.18 (s, 1H), 7.44 (t, J=9.2 Hz, 1H), 7.83 (m, 1H), 8.20 (dd, J=2.7, 6.8 Hz, 1H), 8.55(s, 1H), 8.56 (s, 1H), 9.83 (s, 1H).

Example 110

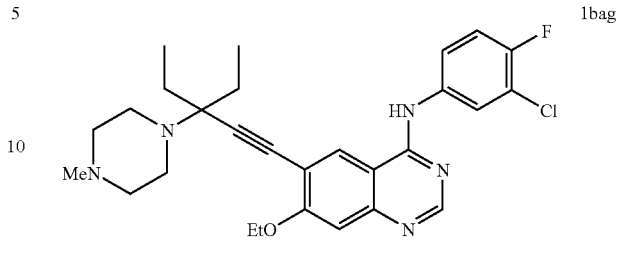

1bag (yield 64%): $^1$H NMR (270 MHz, DMSO-d$_6$) δ ppm: 0.97 (t, J=7.0 Hz, 6H), 1.42 (t, J=7.0 Hz, 3H), 1.71 (m, 4H), 2.15 (s, 3H), 2.35 (br s, 4H), 2.69 (br s, 4H), 4.21 (q, J=7.0 Hz, 2H), 7.17 (s, 1H), 7.44 (t, J=9.2 Hz, 1H), 7.81 (m, 1H), 8.17 (dd, J=2.7, 6.8 Hz, 1H), 8.54 (s, 1H), 8.55 (s, 1H), 9.87 (s, 1H).

Example 111

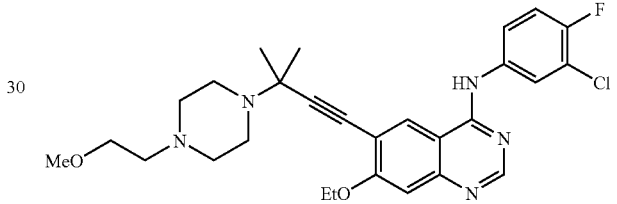

1bah (yield 29%): $^1$H NMR (270 MHz, DMSO-d$_6$) δ ppm: 1.43 (s, 6H), 1.45 (t, J=7.0 Hz, 3H), 2.42-2.52 (m, 4H), 2.44 (t, J=5.8 Hz, 2H), 2.71 (br s, 4H), 3.22 (s, 3H), 3.41 (t, J=5.8 Hz, 2H), 4.21 (q, J=7.0 Hz, 2H), 7.17 (s, 1H), 7.44 (t, J=8.9 Hz, 1H), 7.83 (m, 1H), 8.20 (dd, J=2.7, 7.0 Hz, 1H), 8.56 (s, 1H), 8.57 (s, 1H), 9.84 (s, 1H).

Synthetic Example 18

Synthesis of trifluoromethanesulfonic acid 7-ethoxy-4-[3-(3-hydroxy-3-methyl-1-butynyl)phenylamino]-6-quinazolinyl ester (6f)

Isopropanol (10 mL)-dichloromethane (2 mL) was added to acetic acid 4-chloro-7-ethoxy-6-quinazolinyl ester (400 mg, 1.50 mmol) with stirring, and 4-(3-aminophenyl)-2-methyl-3-butyn-1-ol (290 mg, 1.65 mmol) was added. After 1.5 hours, hexane (50 mL) was added and the mixture was concentrated. Isopropanol (10 mL)-dichloromethane (2 mL) was added to the residue and hexane (30 mL) was slowly added dropwise. The mixture was stirred under ice-cooling for 15 min. The product was collected by filtration and dried under reduced pressure to give acetic acid (7-ethoxy-4-[3-(3-hydroxy-3-methyl-1-butynyl)phenylamino]-6-quinazolinyl ester (547 mg, 83%) as a yellow solid.

This ester compound (513 mg, 1.16 mmol) was dissolved in methanol (5 mL) and 28% aqueous ammonia (1 mL) was added at room temperature. The mixture was stirred and water (10 mL) was added. After stirring for 30 min, the product was collected by filtration and dried under reduced pressure to give 7-ethoxy-4-[3-(3-hydroxy-3-methyl-1-bu tynyl)phenylamino]quinazolin-6-ol (392 mg, 93%) as a colorless solid.

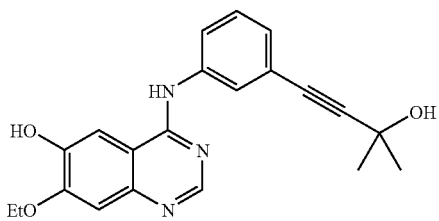

¹H NMR (270 MHz, DMSO-d₆) δ ppm: 1.44 (t, J=7.0 Hz, 3H), 1.48 (s, 6H), 4.24 (q, J=7.0 Hz, 2H), 5.51 (s, 1H), 7.08 (d, J=7.8 Hz, 1H), 7.18 (s, 1H), 7.34 (t, J=8.0 Hz, 1H), 7.80 (s, 1H), 7.88 (d, J=8.4 Hz, 1H), 7.99 (s, 1H), 8.47 (s, 1H), 9.37 (s, 1H), 9.56 (br s, 1H).

In the same manner as in Synthetic Example 13-2), this compound was converted to the title compound (6f) (quantitative).

6f

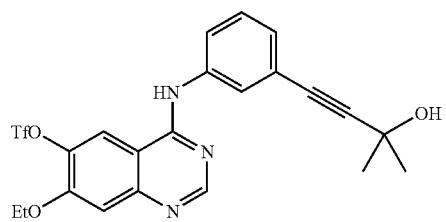

6f: ¹H NMR (270 MHz, DMSO-d₆) δ ppm: 1.46 (t, J=7.0 Hz, 3H), 1.48 (s, 6H), 4.41 (q, J=7.0 Hz, 2H), 7.35 (d, J=7.6 Hz, 1H), 7.46 (s, 1H), 7.51 (t, J=8.0 Hz, 1H), 7.69 (d, J=8.1 Hz, 1H), 7.76 (s, 1H), 8.88 (s, 1H), 8.96 (s, 1H), 11.19 (br s, 1H).

Example 112

Using compound 6f and compound 4c and in the same manner as in Example 88, a coupling compound was obtained (yield 76%). A suspension (21 mL) of this coupling compound (565 mg, 1.05 mmol) and potassium hydroxide (299 mg, 5.33 mmol) in toluene was stirred at 80° C. for 1 hr and under reflux for 1.5 hrs. The reaction mixture was concentrated and water was added to the residue. The mixture was extracted with ethyl acetate and the extract was dried and concentrated and subjected to silica gel column chromatography (ethyl acetate). The obtained solid was recrystallized from ethanol-water to give a compound 1bai (162 mg, 32%).

1bai

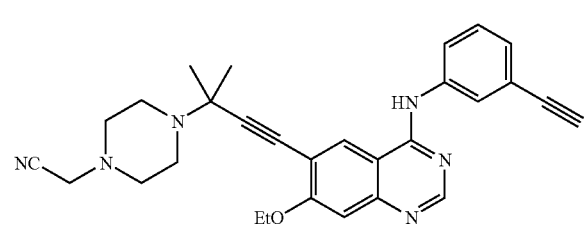

1bai : ¹H NMR (270 MHz, DMSO-d₆) δ ppm: 1.40-1.50 (m, 9H), 2.56 (br s, 4H), 2.77 (br s, 4H), 3.72 (s, 2H), 4.20 (s, 1H), 4.21 (q, J=7.0 Hz, 2H), 7.17 (s, 1H), 7.22 (d, J=7.8 Hz, 1H), 7.40 (t, J=8.0 Hz, 1H), 7.92 (d, J=8.1 Hz, 1H), 8.07 (m, 1H), 8.56 (s, 1H), 8.60 (s, 1H), 9.78 (br s, 1H), Examples 113-117

Using triflate compound 6f and various compounds 4, and in the same manner as in Example 112, compounds 1baj-1ban were synthesized. The structure and spectrum data of the compounds are shown in the following.

Example 113

1baj

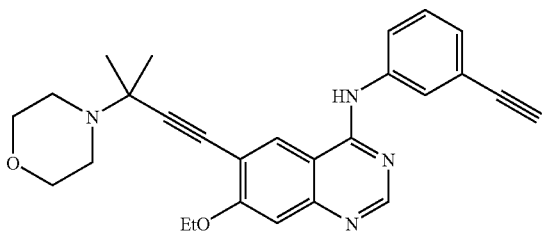

1baj : ¹H NMR (300 MHz, DMSO-d₆) δ ppm: 1.44 (s, 6H), 1.45 (t, J=7.1 Hz, 3H), 2.71 (m, 4H), 3.65 (m, 4H), 4.21 (s, 1H), 4.22 (q, J=7.1 Hz, 2H), 7.18 (s, 1H), 7.22 (d, 1H), 7.40 (t, J=8.1 Hz, 1H), 7.90 (d, 1H), 8.07 (s, 1H), 8.57 (s, 1H), 8.60 (s, 1H), 9.79 (s, 1H).

Example 114

1bak

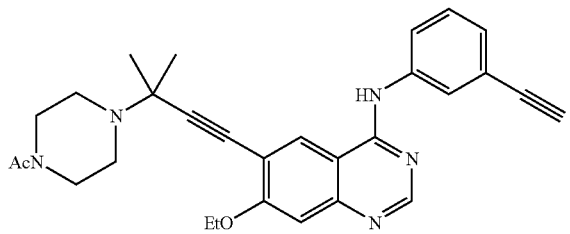

1bak: ¹H NMR (270 MHz, DMSO-d₆) δ ppm: 1.40 (t, J=7.0 Hz, 3H), 1.53 (s, 6H), 2.01 (s, 3H), 2.81 (br s, 4H), 3.55 (br s, 4H), 4.21 (d, J=7.0 Hz, 2H), 4.21 (s, J=7.0 Hz, 1H), 7.19 (s, 1H), 7.24 (d, J=7.8 Hz, 1H), 7.41 (t, J=7.9 Hz, 1H), 7.91 (d, J=8.6 Hz, 1H), 8.06 (s, 1H), 8.60 (s, 1H), 8.67 (s, 1H), 9.91 (br s, 1H).

Example 115

1bal

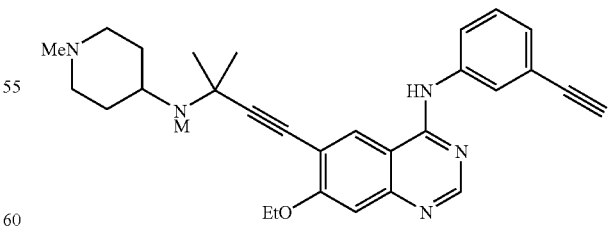

1bal: ¹H NMR (270 MHz, DMSO-d₆) δ ppm: 1.42 (t, J=6.8 Hz, 3H), 1.49 (s, 6H), 1.52-1.90 (m, 6H), 2.11 (s, 3H), 2.37 (s, 3H), 2.77 (br d, J=11.1 Hz, 2H), 2.95 (s, 1H), 4.21 (s, 1H), 4.22 (q, 2H), 7.17 (s, 1H), 7.21 (d, J=7.8 Hz, 1H), 7.40 (t, J=8.0 Hz, 1H), 7.91 (d, J=8.4 Hz, 1H), 8.07 (br s, 1H), 8.56 (s, 2H), 9.78 (br s, 1H).

Example 116

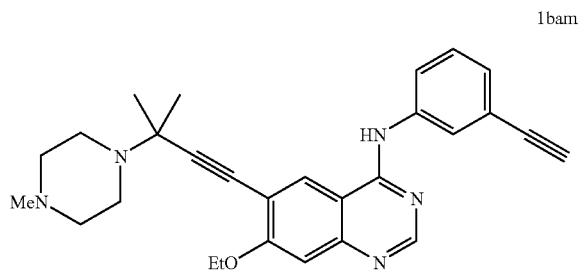

1bam

1bam: $^1$H NMR (300 MHz, DMSO-$d_6$) δ ppm: 1.52 (s, 6H), 1.52 (t, J=7.0 Hz, 3H), 2.31 (s, 3H), 2.55 (br s, 4H), 2.87 (br s, 4H), 3.09 (s, 1H), 4.19 (q, J=7.0 Hz, 2H), 7.15 (s, 1H), 7.28 (d, 1H), 7.28 (d, 1H), 7.36 (t, 1H), 7.80 (d, 1H), 7.91 (br s, 1H), 7.96 (s, 1H), 8.12 (s, 1H), 8.66 (s, 1H).

Example 117

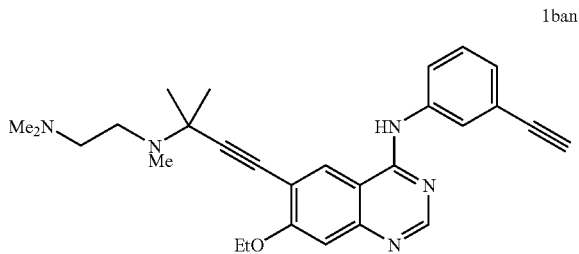

1ban

1ban: $^1$H NMR (270 MHz, DMSO-$d_6$) δ ppm: 1.44 (m, 9H), 2.15 (s, 6H), 2.25-2.40 (m, 5H), 2.62 (t, J=7.2 Hz, 2H), 4.21 (s, 1H), 4.22 (q, 2H), 7.17 (s, 1H), 7.22 (d, J=7.6 Hz, 1H), 7.40 (t, J=8.0 Hz, 1H), 7.92 (d, J=8.4 Hz, 1H), 8.08 (s, 1H), 8.56 (s, 1H), 8.60 (s, 1H), 9.79 (br s, 1H).

Examples 118-130

Synthesized from the corresponding amino compound 2 in the same manner as in Example 66.

Example 118

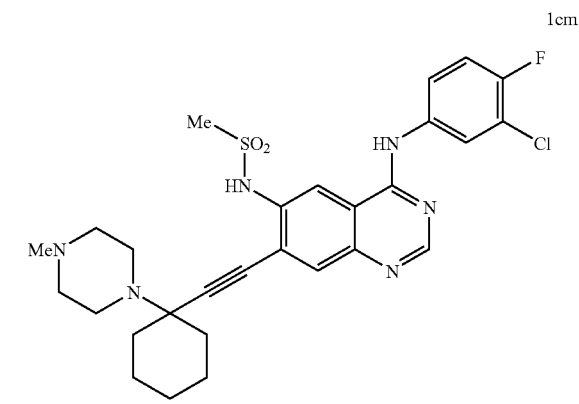

1cm

1cm: yield 57%; $^1$H NMR (270 MHz, DMSO-$d_6$) δ ppm: 1.33 (m, 1H), 1.63 (m, 7H), 2.00 (m, 2H), 2.21 (s, 3H), 2.44 (br s, 4H), 2.71 (br s, 4H), 3.10 (s, 3H), 7.46 (t, J=9.2 Hz, 1H), 7.79 (m, 1H), 7.83(s, 1H), 8.12 (dd, J=2.7, 6.8 Hz, 1H), 8.39 (s, 1H), 8.60 (s, 1H), 10.06 (s, 1H).

Example 119

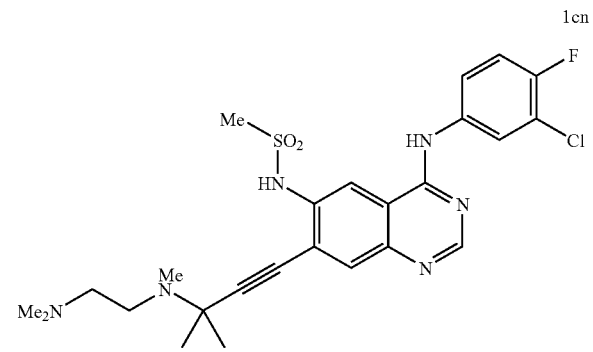

1cn

1cn: yield 62%; $^1$H NMR (270 MHz, DMSO-$d_6$) δ ppm: 1.44 (s, 6H), 2.30 (s, 3H), 2.38 (s, 6H), 2.61(t, J=6.3 Hz, 2H), 2.83 (t, J=6.3 Hz, 2H), 2.99 (s, 3H), 7.45 (t, J=9.2 Hz, 1H), 7.77 (s, 1H), 7.79(m, 1H), 8.11 (dd, J=2.7, 7.0 Hz, 1H), 8.27 (s, 1H), 8.54 (s, 1H), 9.97 (s, 1H).

Example 120

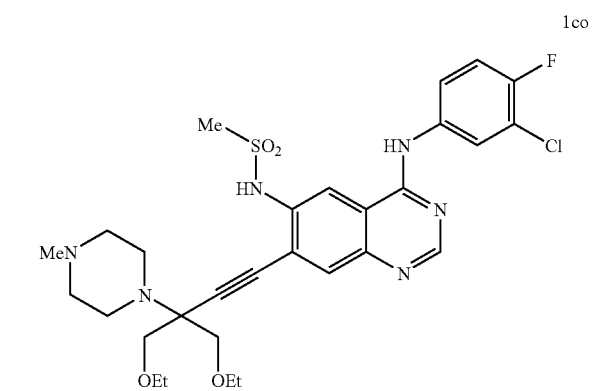

1co

1co: yield 41%; $^1$H NMR (270 MHz, DMSO-$d_6$) δ ppm: 1.13 (t, J=7.0 Hz, 6H), 2.17 (s, 3H), 2.39 (br s, 4H), 2.75 (br s, 4H), 3.08 (s, 3H), 3.52 (q, J=7.0 Hz, 4H), 3.67 (m, 4H), 7.45 (t, J=9.2 Hz, 1H), 7.78 (m, 1H), 7.82 (s, 1H), 8.11 (dd, J=2.7, 7.0 Hz, 1H), 8.40 (s, 1H), 8.59 (s, 1H), 10.07 (s, 1H).

Example 121

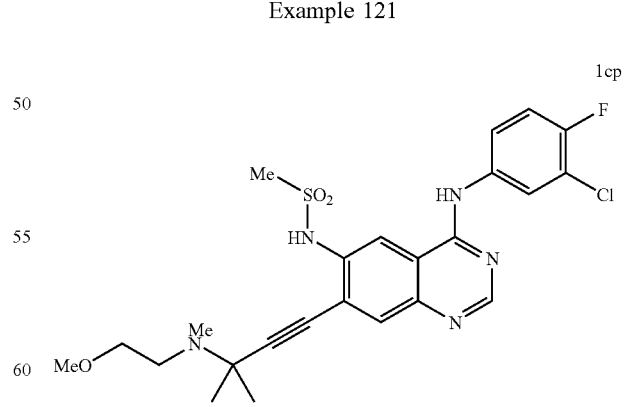

1cp

1cp: yield 56%; $^1$H NMR (270 MHz, DMSO-$d_6$) δ ppm: 1.45 (s, 6H), 2.34 (s, 3H), 2.71(t, J=6.3 Hz, 2H), 3.12(s, 3H), 3.26 (s, 3H), 3.43 (t, J=6.3 Hz, 2H), 7.47 (t, J=9.1 Hz, 1H), 7.81 (m, 1H), 7.84(s, 1H), 8.13 (dd, J=2.6, 6.9 Hz, 1H), 8.45 (s, 1H), 8.62 (s, 1H), 10.08 (s, 1H).

Example 122

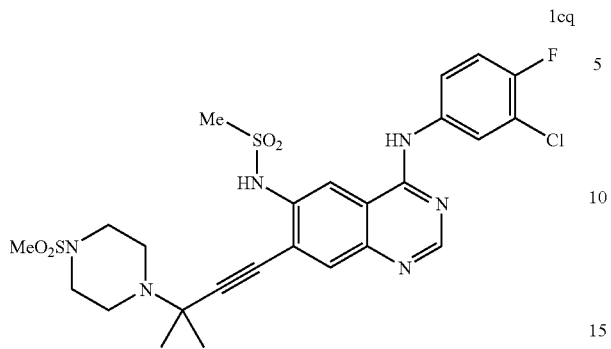

1cq: yield 63%; ¹H NMR (270 MHz, DMSO-d$_6$) δ ppm: 1.48 (s, 6H), 2.78 (br s, 4H), 2.87 (s, 3H), 3.10 (s, 3H), 3.15 (br s, 4H), 7.46 (t, J=9.2 Hz, 1H), 7.79 (m, 1H), 7.87(s, 1H), 8.12 (dd, J=2.4, 7.0 Hz, 1H), 8.45 (s, 1H), 8.61 (s, 1H), 9.57 (br s, 1H),10.09 (s, 1H).

Example 123

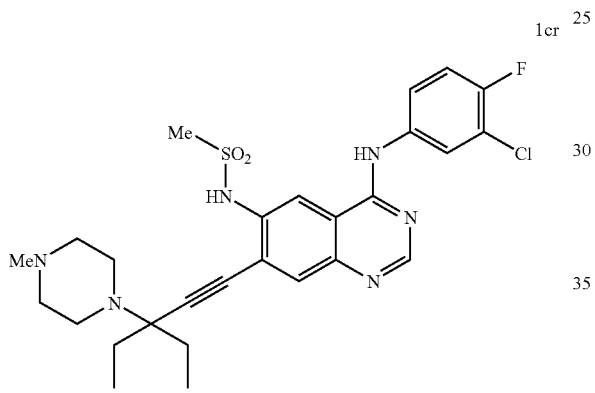

1cr: yield 55%; ¹H NMR (270 MHz, DMSO-d6) δ ppm: 0.93 (t, J=7.3 Hz, 6H), 1.74 (m, 4H), 2.19 (s, 3H), 2.41 (br s, 4H), 2.68(br s, 4H), 3.08 (s, 3H), 7.45 (t, J=9.2 Hz, 1H), 7.77 (m, 1H), 7.81(s, 1H), 8.10 (dd, J=2.4, 7.0 Hz, 1H), 8.37 (s, 1H), 8.58 (s, 1H), 10.04 (s, 1H).

Example 124

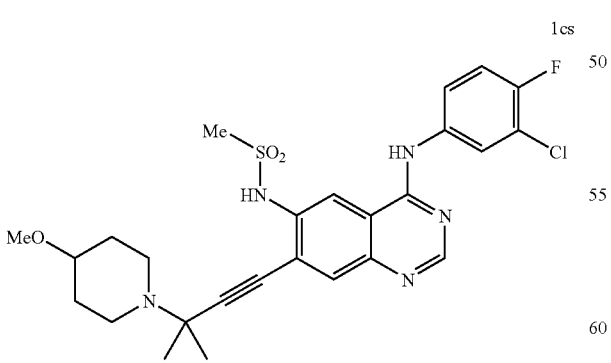

1cs: yield 49%; ¹H NMR (270 MHz, DMSO-d$_6$) δ ppm: 1.42 (m, 2H), 1.46 (s, 6H), 1.89 (m, 2H), 2.37 (m, 2H), 2.97(m, 2H), 3.10 (S, 3H), 3.22(s, 3H), 3.00-4.00 (m, 1H), 7.46 (t, J=9.2 Hz, 1H), 7.79 (m, 1H), 7.83(s, 1H), 8.11 (dd, J=2.7, 7.0 Hz, 1H), 8.44 (s, 1H), 8.61 (s, 1H), 10.08 (s, 1H).

Example 125

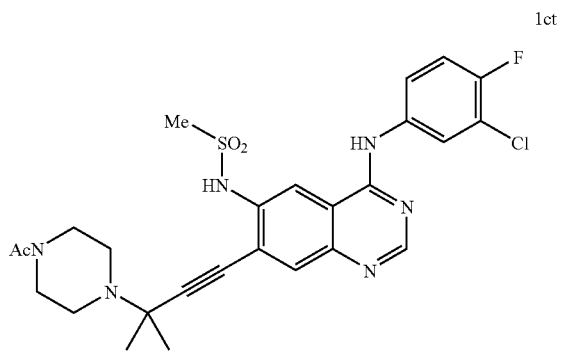

1ct: yield 34%; 1H NMR (270 MHz, DMSO-d$_6$) δ ppm: 1.47 (s, 6H), 1.99 (s, 3H), 2.61 (br s, 2H), 2.68 (br s, 2H), 3.09(s, 3H), 3.44 (br s, 4H), 7.45 (t, J=9.2 Hz, 1H), 7.78 (m, 1H), 7.84(s, 1H), 8.11 (dd, J=2.7, 7.0 Hz, 1H), 8.44 (s, 1H), 8.60 (s, 1H), 10.08 (s, 1H).

Example 126

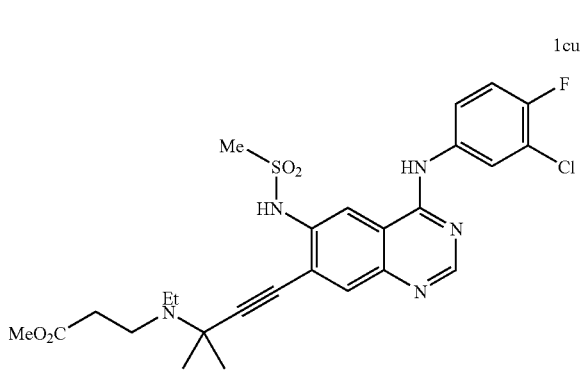

1cu: yield 69%; ¹H NMR (270 MHz, DMSO-d$_6$) δ ppm: 1.06 (t, J=7.0 Hz, 3H), 1.47 (s, 6H), 2.50 (m, 2H), 2.75 (q, J=7.0 Hz, 2H), 2.98 (t, J=7.0 Hz, 2H), 3.11 (s, 3H), 3.59(s, 3H), 7.47 (t, J=9.2 Hz, 1H), 7.80 (m, 1H), 7.83(s, 1H), 8.13 (dd, J=2.7, 7.0 Hz, 1H), 8.45 (s, 1H), 8.62 (s, 1H), 9.52 (br s, 1H), 10.09 (s, 1H).

Example 127

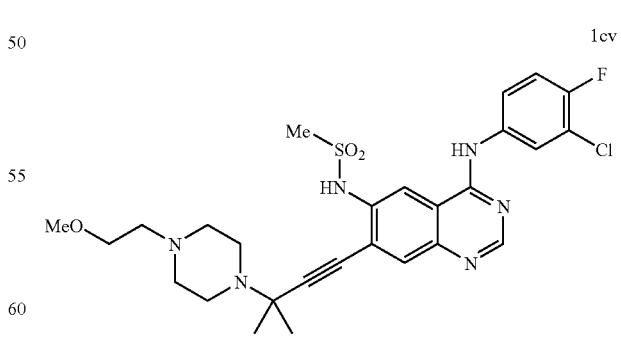

1cv: yield 53%; ¹H NMR (270 MHz, DMSO-d$_6$) δ ppm: 1.46 (s, 6H), 2.50 (br s, 6H), 2.69 (br s, 4H), 3.11 (s, 3H), 3.23 (s, 3H), 3.43(m, 2H), 7.47 (t, J=9.2 Hz, 1H), 7.80 (m, 1H), 7.84(s, 20 1H), 8.13 (dd, J=2.4, 6.8 Hz, 1H), 8.44 (s, 1H), 8.62 (s, 1H), 10.08 (s, 1H).

Example 128

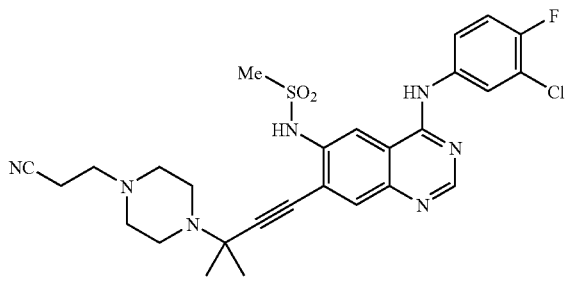

1cw: yield 48%; ¹H NMR (270 MHz, DMSO-d₆) δ ppm: 1.47 (s, 6H), 2.50-2.58 (m, 6H), 2.65-2.70 (m, 6H), 3.12 (s, 3H), 7.47 (t, J=9.2 Hz, 1H), 7.81 (m, 1H), 7.84(s, 1H), 8.14 (dd, J=2.7, 7.0 Hz, 1H), 8.47 (s, 1H), 8.62 (s, 1H), 9,59 (br s, 1H),10.10 (s, 1H).

Example 129

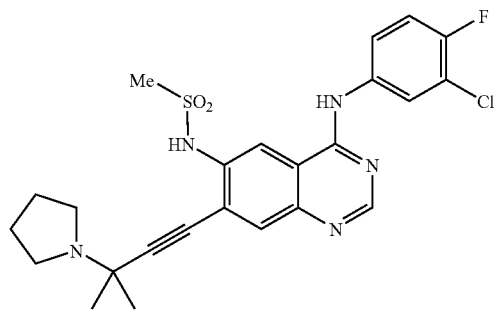

1cx: yield 45%; ¹H NMR (270 MHz, DMSO-d₆) δ ppm: 1.48 (s, 6H), 1.74 (br s, 4H), 2.76 (br s, 4H), 3.12(s, 3H), 7.47 (t, J=9.2 Hz, 1H), 7.79 (m, 1H), 7.84(s, 1H), 8.13 (dd, J=2.4, 7.0 Hz, 1H), 8.45 (s, 1H), 8.62 (s, 1H), 10.09 (s, 1H).

Example 130

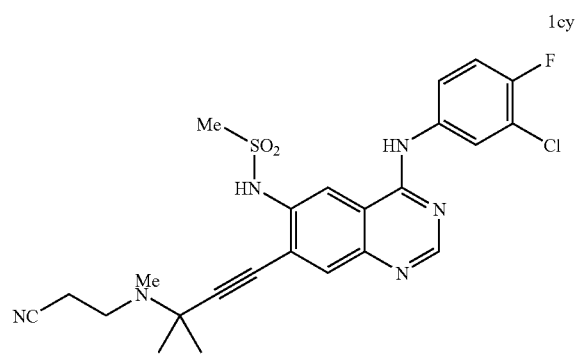

1cy: yield 42%; ¹H NMR (270 MHz, DMSO-d₆) δ ppm: 1.48 (s, 6H), 2.36 (s, 3H), 2.68 (t, J=6.4 Hz, 2H),-2.82 (t, J=6.4 Hz, 2H), 3.12 (s, 3H), 7.47 (t, J=9.0 Hz, 1H), 7.81 (m, 1H), 7.88(s, 1H), 8.13 (dd, J=2.4, 7.0 Hz, 1H), 8.46 (s, 1H), 8.62 (s, 1H), 9.57 (s, 1H), 10.09 (s, 1H).

Example 131

Using N⁴-(3-chloro-4-fluorophenyl)-6-[3-methyl-3-(4-methyl-1-piperazinyl)-1-butynyl]-4,7-quinazolinediamine (2a') synthesized in Example 78 and in the same manner as in Example 1, the compound was converted to compound 1a'. The crude product was left standing for three days and compound 1a' (containing about 0.9 equivalent amount of DMF) was obtained as needle crystals (yield 20%).

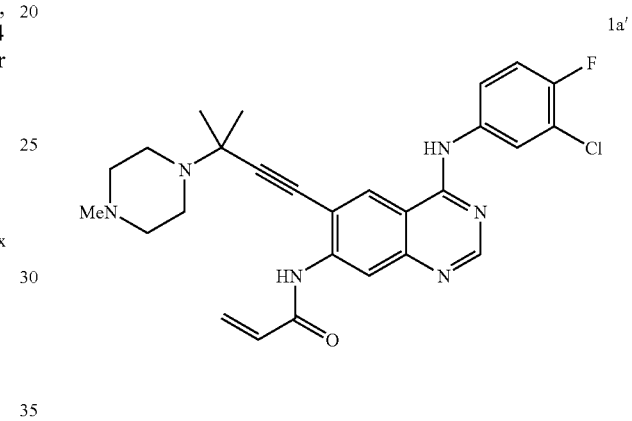

1a': ¹H NMR (300 MHz, DMSO-d₆) δ ppm: 1.48 (s, 6H), 1.99 (s, 3H), 2.15 (br s, 4H), 2.68 (br s, 4H), 5.88 (d, J=10.4 Hz, 1H), 6.36 (d, J=17.1 Hz, 1H), 6.61 (dd, J=10.4, 17.1 Hz, 1H), 7.46 (t, J=9.1 Hz, 1H), 7.84 (m, 1H), 8.20 (dd, J=2.5, 6.8 Hz, 1H), 8.32 (s, 1H), 8.61 (s, 1H), 8.67 (s, 1H), 9.38 (s, 1H), 9.99 (s, 1H).

Example 132

Using 4ao (yield 60%) synthesized in the same manner as in Synthetic Example 7 using 4-oxotetrahydropyran and 7-bromo-N⁴-(3-chloro-4-fluorophenyl)-4,6-quinazolinediamine as starting materials, and in the same manner as in Example 3, the compound was converted to 2ao and 1ao.

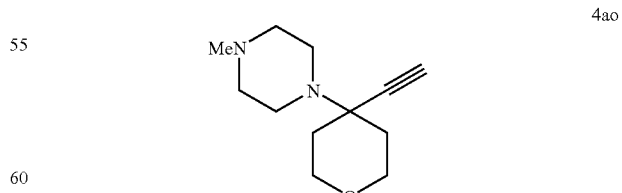

4ao: yield 60%; ¹H NMR (270 MHz, CDCl₃) δ ppm: 1.60-1.71 (m, 2H), 1.87-1.93 (m, 2H), 2.29 (s, 3H), 2.40 (s, 1H), 2.49. (br s, 4H), 2.67 (br s, 4H), 3.64-3.74 (m, 2H), 3.90-3.96 (m, 2H).

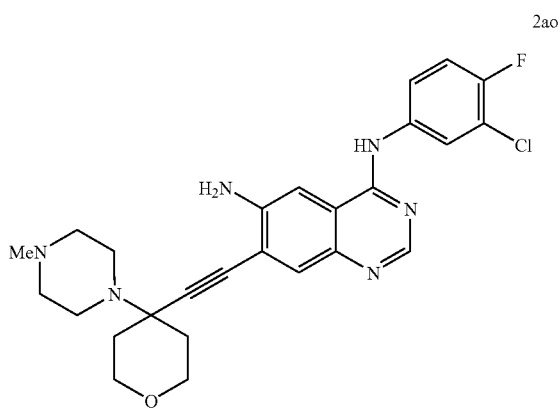

2ao: yield quantitative; $^1$H NMR (270 MHz, DMSO-$d_6$) δ ppm: 1.53-1.65 (m, 2H), 2.04-2.12 (m, 2H), 2.15 (s, 3H), 2.37(br s, 4H), 2.64 (br s, 4H), 3.60 (m, 2H), 3.88 (m, 2H), 5.53 (s, 2H), 7.41 (t, J=9.2 Hz, 1H), 7.53(s, 1H), 7.70 (s, 1H), 7.81 (m, 1H), 8.20 (dd, J=6.8, 2.7 Hz, 1H), 8.39 (s, 1H), 9.64 (s, 1H).

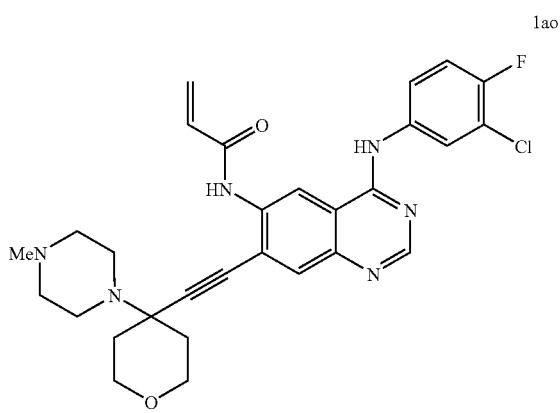

1ao: yield 31%; $^1$H NMR (270 MHz, DMSO-$d_6$) δ ppm: 1.55 (m, 2H), 2.01 (m, 2H), 2.15 (s, 3H), 2.36 (br s, 4H), 2.63 (br s, 4H), 3.61 (m, 2H), 3.84 (m, 2H), 5.84 (d, J=10.0 Hz, 1H), 6.32 (d, J=17.0 Hz, 1H), 6.55 (dd, J=17.0, 10.0 Hz, 1H), 7.46 (t, J=9.2 Hz, 1H), 7.85 (m, 1H), 7.90 (s, 1H), 8.20 (br d, J=6.8 Hz, 1H), 8.64 (s, 1H), 8.65 (s, 1H), 9.96 (s, 1H), 10.00 (s, 1H).

Example 133

A solution (4.5 mL) of acrylamide compound 1z (300 mg, 1.46 mmol) obtained by the method of Example 25 in dichloromethane was cooled to 0° C. to 5° C., and trifluoroacetic acid (TFA) (4.5 mL) was added. The mixture was stirred as it was for 1.5 hrs and the solvent was evaporated under reduced pressure. The residue was suspension-washed with diethyl ether and collected by filtration to give the objective compound 1ap.nTFA (50 mg).

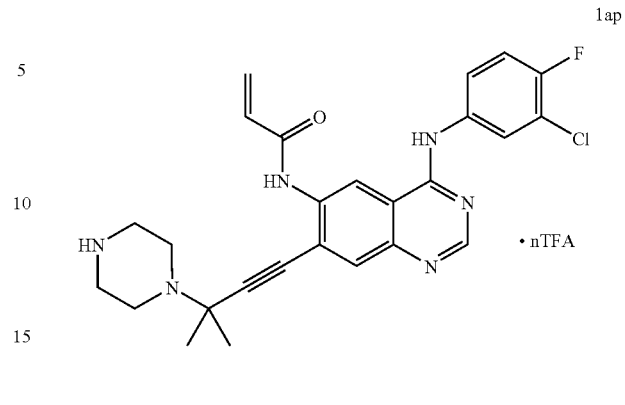

1ap.nTFA : $^1$H NMR (270 MHz, DMSO-$d_6$) δ ppm: 1.46 (s, 6H), 2.86 (br s, 4H), 3.14 (br s, 4H), 5.87 (d, J=10.0 Hz, 1H), 6.34 (d, J=17.0 Hz, 1H), 6.58 (dd, J=17.0, 10.0 Hz, 1H), 7.50 (t, J=9.2 Hz, 1H), 7.77 (m, 1H), 7.92(s, 1H), 8.11 (m, 1H), 8.57 (br s, 2H), 8.75 (s, 1H), 8.77 (s, 1H), 10.01 (s, 1H), 10.53 (br s, 1H).

Example 134

A solution (30 mL) of 4-(4-methyl-1-piperazinyl)-4-oxobutyric acid (0.69 g, 10.0 mmol), N-methylpropargylamine (2.00 g, 10.0 mmol), EDC (2.88 g, 15.0 mmol) and triethylamine (2.1 mL, 15.0 mmol) in DMF was stirred at room temperature overnight. Water (40 mL) was added to the reaction mixture and the product was extracted with dichloromethane (40 mL×3). The extract was washed with aqueous sodium hydrogen carbonate and saturated brine and concentrated under reduced pressure to give a solution (10.00 g) of N-methyl-4-(4-methyl-1-piperazinyl)-4-oxo-N-(2-propynyl)butylamide (4aq) in DMF.

Using this DMF solution of 4aq and 7-bromo-$N^4$-(3-chloro-4-fluorophenyl)-4,6-quinazolinediamine and in the same manner as in Example 3, the compound was converted to 1aq.

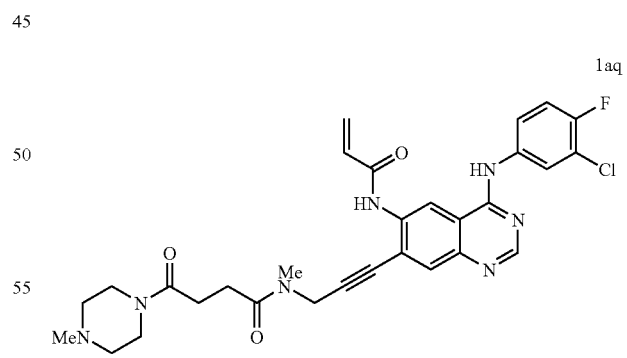

1aq: yield 7%; $^1$H NMR (300 MHz, 354K, DMSO-$d_6$) δ ppm: 2.18 (s, 3H), 2.27 (m, 4H), 2.60(m, 4H), 3.02 (s, 3H), 3.44 (m, 4H), 4.48 (s, 2H), 5.80 (dd, J=10.1, 1.5 Hz, 1H), 6.33 (dd, J=16.8, 1.5 Hz, 1H), 6.60 (m, 1H), 7.38 (t, J=9.2 Hz, 1H), 7.82 (m, 1H), 7.86 (s, 1H), 8.12 (m, 1H), 8.57 (s, 1H), 8.78 (s, 1H), 9.55 (br s, 1H), 9.82 (br s, 1H); LC-MS: m/z=592 ($M^+$+1).

Example 135

Using 4ar (yield 97%) synthesized in the same manner as in Synthetic Example 7 using tert-butyl 4-oxo-1-piperidinecarboxylate instead of 1,3-diethoxyacetone, and diethylamine instead of 1-methylpiperazine, and 7-bromo-N-(3-chloro-4-fluorophenyl)-4,6-quinazolinediamine, 2ar (R=H) can be obtained according to a method similar to that of Example 3-1). This is reacted with a monoequivalent amount of di-tert-butyl dicarboxylate (Boc$_2$O) under ice-cooling in dichloromethane for 30 min and a crude product was purified by silica gel column chromatography to give compound 2ar (R=Boc; total yield 85%). The compound 2ar (R=Boc) was introduced into 1ar' by the method of Example 3-2) and converted to 1ar by the method described in Example 142.

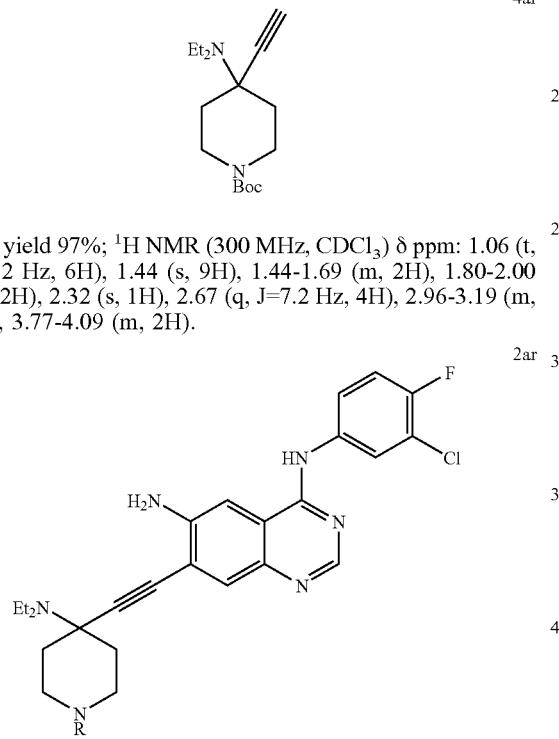

4ar: yield 97%; $^1$H NMR (300 MHz, CDCl$_3$) δ ppm: 1.06 (t, J=7.2 Hz, 6H), 1.44 (s, 9H), 1.44-1.69 (m, 2H), 1.80-2.00 (m, 2H), 2.32 (s, 1H), 2.67 (q, J=7.2 Hz, 4H), 2.96-3.19 (m, 2H), 3.77-4.09 (m, 2H).

2ar (R=Boc): yield 85%; $^1$H NMR (300 MHz, CDCl$_3$) δ ppm: 1.12 (t, J=7.1 Hz, 6H), 1.47 (s, 9H), 1.65-1.81 (m, 2H), 1.91-2.11 (m, 2H), 2.78 (q, J=7.1 Hz, 4H), 3.07-3.27 (m, 2H), 3.83-4.09 (m, 2H), 4.47 (br s, 2H), 6.98 (s, 1H), 7.15 (t, J=8.7 Hz, 1H), 7.24 (br s, 1H), 7.54 (m, 1H), 7.86 (s, 1H), 7.93 (dd, J=2.5, 6.4 Hz, 1H), 8.58 (s, 1H).

1ar': yield 63%; $^1$H NMR (300 MHz, CDCl$_3$) δ ppm: 1.04 (br t, 6H), 1.41 (s, 9H), 1.52 (m, 2H), 2.02 (br d, J=12.3 Hz, 2H), 2.71 (br q, 4H), 3.12 (m, 2H), 3.82 (br d, J=10.0 Hz, 2H), 5.82 (d, J=10.2 Hz, 1H), 6.31 (d, J=16.9 Hz, 1H), 6.51 (dd, 10.2, 16.9 Hz, 1H), 7.45 (t, J=9.1 Hz, 1H), 7.84 (m, 1H), 8.19 (dd, J=2.6, 6.8 Hz, 1H), 8.61 (s, 1H), 8.64 (s, 1H), 9.98 (br s, 2H).

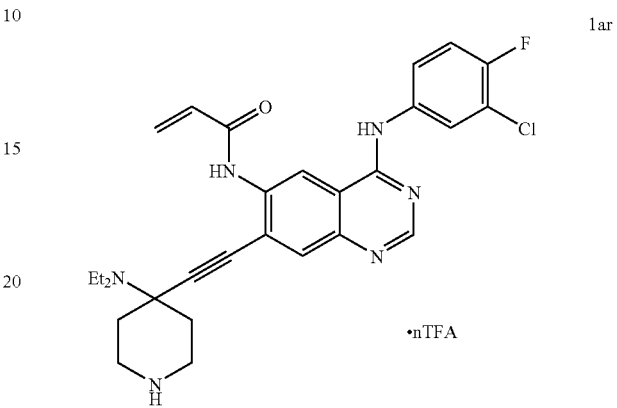

1ar.nTFA: yield 76% (n=3); $^1$H NMR (300 MHz, DMSO-d$_6$) δ ppm: 1.29 (br s, 6H), 2.03-2.24 (m, 2H), 3.05-3.65 (m, 10H), 5.90 (d, J=10.0 Hz, 1H), 6.38 (d, J=17.0 Hz, 1H), 6.56 (dd, J=10.0, 17.0 Hz, 1H), 7.49 (t, J=9.1 Hz, 1H), 7.80 (m, 1H), 8.16 (dd, J=2.3, 7.0 Hz, 1H), 8.19 (s, 1H), 8.66-9.02 (m, 2H), 8.70 (s, 1H), 8.74 (s, 1H), 10.34 (s, 2H).

Example 136

Using the compound 4cz obtained by reacting propargylamine with ethyl isonipecotinate in acetonitrile in the presence of potassium carbonate from ice-cooling to room temperature and 7-bromo-N$^4$-(3-chloro-4-fluorophenyl)-4,6-quinazolinediamine, and in the same manner as in Example 3,1-{3-[6-amino-4-(3-chloro-4-fluorophenylamino)-7-quinazolinyl]-2-propynyl}-4-piperidinecarboxylic acid ethyl ester (2cz) was obtained (yield 73%). The compound 2cz was reacted in the same manner as in Example 66 and the crude product was subjected to silica gel column chromatography. The obtained solid was treated with an about 3 equivalent amount of 2N aqueous sodium hydroxide solution in ethanol at room temperature for 2 hrs and neutralized to give precipitate. The product was collected by filtration and suspension-washed with acetonitrile to give compound 1cz as a pale-yellow solid (yield 57%).

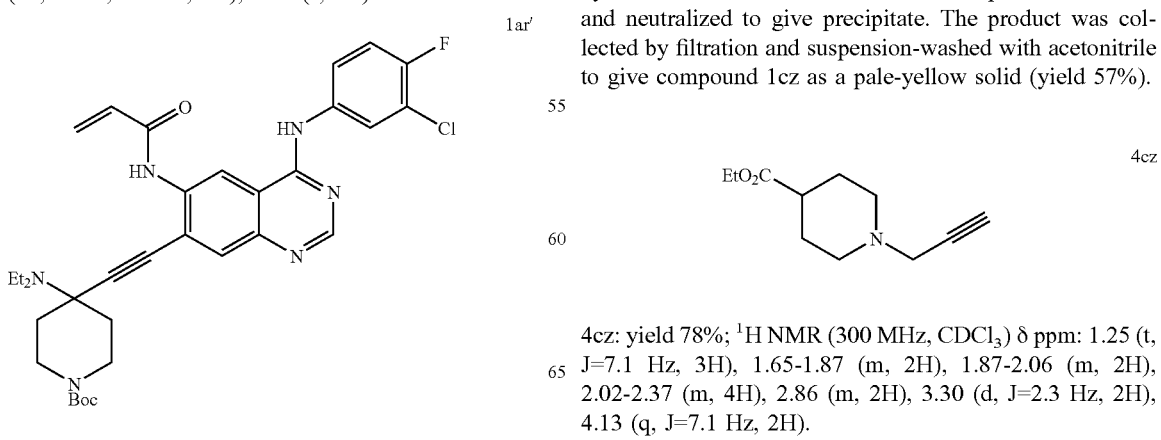

4cz: yield 78%; $^1$H NMR (300 MHz, CDCl$_3$) δ ppm: 1.25 (t, J=7.1 Hz, 3H), 1.65-1.87 (m, 2H), 1.87-2.06 (m, 2H), 2.02-2.37 (m, 4H), 2.86 (m, 2H), 3.30 (d, J=2.3 Hz, 2H), 4.13 (q, J=7.1 Hz, 2H).

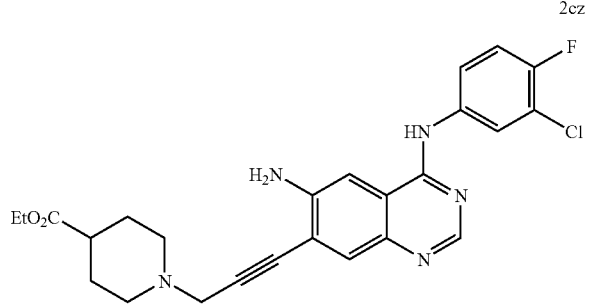

2cz: yield 73%.

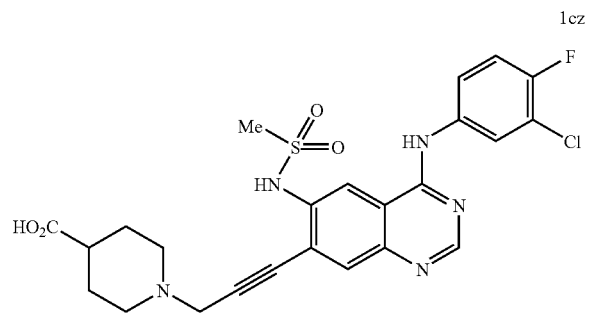

1cz: $^1$H NMR (300 MHz, DMSO-$d_6$) δ ppm: 1.46-1.67 (m, 2H), 1.76-1.91 (m, 2H), 2.16-2.39 (m, 3H), 2.80-2.94 (m, 2H), 3.08 (s, 3H), 3.75 (s, 2H), 7.46 (t, J=9.1 Hz, 1H), 7.72-7.83 (m, 1H), 7.85 (s, 1H), 8.11 (br d, J=6.9 Hz, 1H), 8.35 (br s, 1H), 8.58 (s, 1H), 10.02 (br s, 1H).

Example 137

Using 3-methoxypropyne and 7-bromo-N$^4$-(3-chloro-4-fluorophenyl)-4,6-quinazolinediamine and in the same manner as in Example 3, the compound was converted to N$^4$-(3-chloro-4-fluorophenyl)-7-(3-methoxy-1-propynyl)quinazoline-4,6-diamine. According to the method described in Example 75, [2-(4-morpholino)ethanesulfonyl chloride was used instead of methanesulfonyl chloride]] to synthesize compound 1caa.

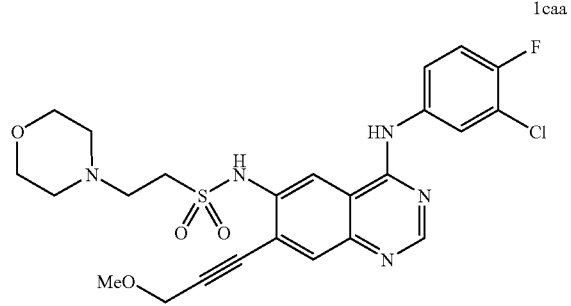

1caa: yield 10%; H NMR (300 MHz, CDCl$_3$) δ ppm: 2.38-2.41 (m, 4H), 2.89 (t, J=6.9 Hz, 2H), 3.38 (t, J=7.2 Hz, 2H), 3.50 (s, 3H), 3.61-3.68 (m, 4H), 4.44 (s, 2H), 7.20 (t, J=9.0 Hz, 1H), 7.52-7.56 (m, 2H), 7.92-7.95 (m, 2H), 8.05 (s, 1H), 8.07 (s, 1H), 8.73 (s, 1H).

Example 138

The compound 2t (Example 20) was converted to 1as according to the method described in Example 1 [using 4-(4-morpholino)-2-butynoic acid instead of acrylic acid].

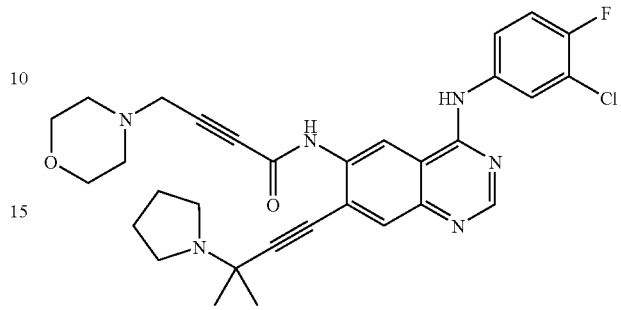

1as: yield 17%; $^1$H NMR (300 MHz, DMSO-$d_6$) δ ppm: 1.47 (br s, 8H), 1.72 (br s, 6H), 2.11 (br s, 4H), 2.72 (br s, 6H), 7.45 (t, J=9.0 Hz, 1H), 7.81-7.85 (m, 2H), 8.18 (d, J=5.1 Hz, 1H), 8.58 (s, 1H), 8.61 (s, 1H), 9.62 (s, 1H), 9.96 (s, 1H).

Test Example 1

Evaluation of Tyrosine Kinase Inhibitor of the Present Invention (1) EGFR Tyrosine Kinase Inhibitory Action (method) Using EGF receptor partially purified by A431 cell line (provided by Institute of Development, Aging and Cancer, Tohoku University, Cell Resource Center for Biomedical Research) derived from human epidermoid cancer, the tyrosine kinase assay of Linda J. Pike et al. (*Proceedings of the National Academy of Science of the U.S.A.*, 1982, 79, 1433) was improved and performed. Specific method was as follows.

A431 cells were cultured in Dulbecco's Modified Eagle Medium (DMEM) containing 10% of fetal calf serum (FBS) at 37° C. under 5% carbon dioxide gas, and homogenized in a solution containing 10 mM N-2-hydroxyethylpiperazino-N'-2-ethanesulfonic acid (Hepes) buffer (pH 7.4), 0.25 M sucrose and 0.1 mM EDTA, and separated by centrifugation at 3000 G for 5 min. The supernatant was separated by centrifugation at 100,000 G for 30 min to separate A431 cell membrane fraction, which was used for the assay as an enzyme source of partially purified EGF receptor.

To a reaction mixture (final concentration 1% DMSO) containing the above-mentioned A431 cell membrane fraction (10 to 15 ag), 30 mM Hepes buffer (pH 7.7), 2 mM MnCl$_2$, 100 μM Na$_3$VO$_4$ and a test substance dissolved in dimethyl sulfoxide (DMSO) was added 100 ng of EGF, after which 50 μg of synthetic substrate Angiotensin II (Asp-Arg-Val-Tyr-Ile-His-Pro-Phe) and a final concentration of 10 μM of adenosine triphosphate (containing γ-$^{32}$P-labeled compound 37 KBq) were added to start the reaction. The volume then was 60 μL.

The reaction was carried out in ice for 30 min and 6 μL of 10 mg/mL bovine serum albumin and 25 μL of 20% trichloroacetic acid were added to stop the reaction. The reaction mixture was left in ice as it was for 30 min.

The mixture was centrifuged at 5000 G for 2 min and the supernatant was sampled by 40 μL and adsorbed on P81 phosphocellulose paper. This was immersed in 0.75% aqueous phosphoric acid for 5 min for rinsing. This rinsing was repeated 4 times. The paper was taken out, the $^{32}$P count was measured on a liquid scintillation counter and this value was taken as A.

Simultaneously, a reaction without the test substance and a reaction without the test substance and EGF were also measured and the counts thereof were taken as B and C, respectively.

The tyrosine kinase inhibitory rate can be determined from the following formula based on these values.

Percent Inhibition (%)=100−{(A−C)/(B−C)}×100

The concentration of the test substance added was changed and the percent inhibition was determined, and from which IC$_{50}$ value (50% inhibitory concentration) was calculated.

TABLE 11

| Compound No. | IC$_{50}$ nM |
| --- | --- |
| 1a | 1.8 |
| 1b | 1.3 |
| 1c | 3.9 |
| 1d | 3.5 |
| 1e | 2.4 |
| 1f | 2.4 |
| 1g | 4.4 |
| 1h | 3.3 |
| 1i | 3.7 |
| 1j | 3.2 |
| 1k | 1.9 |
| 1l | 1.8 |
| 1m | 1.9 |
| 1n | 2.1 |
| 1o | 4.6 |
| 1p | <1 |
| 1q | 2.6 |
| 1r | 1.5 |
| 1s | 2.9 |
| 1t | 2.6 |
| 1v | <1 |
| 1x | <1 |
| 1y | <1 |
| 1aa | 1.7 |
| 1ab | 2.1 |
| 1ac | <1 |
| 1ae | <1 |
| 1ba | 1.1 |
| 1bb | 1.3 |
| 1bc | 1.6 |
| 1bd | 3.0 |
| 1be | 8.0 |
| 1bf | 0.82 |
| 1bg | >10 |
| 1bh | 4.4 |
| 1bi | 1.0 |
| 1bj | 2.9 |
| 1bk | 2.1 |
| 1bl | 2.2 |
| 1bm | 2.8 |
| 1bn | 3.5 |
| 1bo | 2.2 |
| 1bp | 2.1 |
| 1bq | 3.8 |
| 1br | 5.7 |
| 1bs | 1.1 |
| 1bt | 5.0 |
| 1bu | 3.2 |
| 1bv | 1.5 |
| 1bw | 2.8 |
| 1bx | 3.4 |
| 1by | >10 |
| 1bz | 2.2 |
| 1baa | 2.8 |
| 1bab | 5.6 |
| 1bac | 1.2 |
| 1bad | 4.0 |
| 1bae | 2.5 |

TABLE 11-continued

| Compound No. | IC$_{50}$ nM |
| --- | --- |
| 1baf | 3.3 |
| 1bag | 5.1 |
| 1bah | 2.6 |
| 1bai | 1.8 |
| 1baj | 3.3 |
| 1bak | >10 |
| 1bal | 3.2 |
| 1bam | 3.3 |
| 1ban | 2.6 |
| 1ca | 7.7 |
| 1cb | <1 |
| 1cd | 2.1 |
| 1ce | <1 |
| 1cg | 2.1 |
| 1ch | 2.6 |
| 1ci | 1.9 |
| 1cj | 2.7 |
| 1ck | <1 |
| 1cl | 6.7 |
| 1cm | 5.2 |
| 1cn | 2.9 |
| 1co | 10.3 |
| 1cp | 3.1 |
| 1cq | 2.1 |
| 1cr | 3.4 |
| 1cs | 5.3 |
| 1ct | 2.1 |
| 1cu | 5.5 |
| 1cv | 1.8 |
| 1cw | 2.5 |
| 1cx | 2.8 |
| 1ap | 2.4 |

(2) HER2 Tyrosine Kinase Inhibitory Action (Method)

As the cells, NIH3T3 mouse fibroblast cell line (provided by Institute of Development, Aging and Cancer, Tohoku University Cell Resource Center for Biomedical Research) transformed with mutated c-erbB2 constitutively activated by substituting valine at position 659 for glutamic acid was used. In the following, the cell is referred to as A4 cell. This cell line was cultured in DMEM/F12 mixed medium (hereinafter a complete medium) supplemented with 10% FBS in a plastic dish at 37° C., 5% CO$_2$, 95% air.

The A4 cells suspended in a complete medium were seeded in a 12-well plate at 3×10$^5$/well, and confluent cells were cultured with the compound at 37° C. for 2 hrs. The cells were washed once with PBS, re-suspended in a lysis buffer (60 mM Tris (pH 6.8), 2% SDS, 10% glycerol, 5% beta-mercaptoethanol, 0.001% bromophenol blue), treated by ultrasonication and applied to Western blotting as a whole cell lysate.

The whole cell lysate (protein amount 25 μg) was applied to 7.5% SDS-polyacrylamide electrophoresis and transferred to PVDF membrane. The membrane was blocked and incubated with antiphosphotyrosine mouse monoclonal antibody in Tris buffer containing 0.1% Tween 20 and then treated with HRP-labeled antimouse second antibody. The membrane was developed with a chemiluminescent reagent. The chemiluminescence was taken with a lumino CCD camera and recorded electronically. The obtained phosphorylation signal was quantified with densitometer and evaluated for the inhibition of phosphorylation by the compound as expressed in % control, wherein the signal without addition of the compound was taken as 100% control and the background signal was taken as 0%.

TABLE 12

| Compounds | % of control at 0.1 µM | % of control at 1 µM |
| --- | --- | --- |
| 1a | 85 | 1 |
| 1f | 61 | 31 |
| 1ap | 74 | 24 |
| 1l | 16 | 5 |
| 1ac | 9 | 3 |

(3) In vitro Cancer Cell Growth Inhibitory Action (Method)

A growth inhibitory test for various human cancer cell lines was performed by the XTT method. Specific method was as follows. The cells suspended in RPMI1640 medium supplemented with 10% FBS were seeded in a 96-well plate at 5,000/100 µ/1 well. Simultaneously, 100 µl/well of a medium containing a pharmaceutical agent diluted in 8 different concentrations of 100 µM to 0.04 µM at 3-fold ratio was seeded. For a compound that showed inhibitory activity at a low concentration, a further lower dose was employed in the test. Thereafter, 1 mg/ml of XTT reagent (manufactured by SIGMA) supplemented with 25 µM of phenazine methosulfate was added at 50 µl/well and the cells were incubated at 37° C. for about 4 hrs to allow staining of viable cells. Colorimetric determination (OD 490 nm) was done with a spectrophotometer.

$IC_{50}$ value (concentration inhibiting cell growth by 50%) was calculated from a dose-inhibition curve and used as an index of inhibitory activity.

(4) In vivo Antitumor Effect (Method)

Human epidermoid cancer cell A431 ($5 \times 10^6$/100 µl) suspended in PBS was subcutaneously implanted on the back of Balb/c female nude mice (Balb/cAJcl-nu mouse, Clea Japan, Inc., 5-week-old when purchased) and when the average volume of the implanted tumor reached approximately about 100 $mm^3$ in about 7 days, the mice were allocated (4 per group) to make the average tumor volume the same for each group. The tumor volume was obtained by measuring the long diameter and the short diameter with a caliper and according to: [(short diameter)$^2$×long diameter/2]=tumor volume [$mm^3$]. A pharmaceutical agent was forcibly administered orally once a day for 14 consecutive days from the day of the allocation, and the drug was not given to the mice of the control group. The relative tumor growth rate, with the tumor volume of the day of start of the administration as 1, was calculated for the control group and the treatment group. Antitumor effect (%) of control=(relative tumor growth rate of treatment group on the last day −1)/(relative tumor growth rate of control group on the last day −1)×100

(Results)

The compound 1a, compound 1f and compound 1a·2TsOH showed a dose-dependent antitumor effect. From these results, it has been clarified that the compound of the present invention is useful as an anticancer agent.

TABLE 13

| antitumor effect on A431 tumor | | | |
| --- | --- | --- | --- |
| pharmaceutical agent | dose [mg/kg] | relative tumor growth rate | % of control |
| control | — | 9.40 | 100 |
| compound 1a | 0.3 | 6.47 | 65.1 |

TABLE 13-continued

| antitumor effect on A431 tumor | | | |
| --- | --- | --- | --- |
| pharmaceutical agent | dose [mg/kg] | relative tumor growth rate | % of control |
| compound 1a | 1 | 4.93 | 46.8 |
| compound 1a | 3 | 2.70 | 20.3 |

TABLE 14

| antitumor effect on A431 tumor | | | |
| --- | --- | --- | --- |
| pharmaceutical agent | dose [mg/kg] | relative tumor growth rate | % of control |
| control | — | 5.76 | 100 |
| compound 1f | 1 | 5.63 | 97.2 |
| compound 1f | 10 | 1.09 | 1.8 |
| compound 1a · 2TsOH | 1 | 2.95 | 41.0 |

(5) Mutagenicity Test (Evaluation Method)

To investigate the mutagenicity of compounds 1a and 1A (compound* described in Example 24 of JP-T-2000-508657), a reversion assay test (preincubation method) was performed using *Salmonella typhimurium* TA100, TA98, TA2637 and *Escherichia coli* WP2uvrA. Each compound in the dose of from 50 (78.1 for compound 1A) to 5000 µg/plate was pretreated at 37° C. for 20 min in the co-existence or absence of S9mix derived from rat liver and layered on the minimum glucose agar medium along with soft agar. After incubation at 37° C. for about 48 hrs, the revertant colonies emerged on the plate were counted. When the number of the revertant colonies in the treated plate increased in a dose-dependent manner and reached not less than 2 times the solvent control value, the result was evaluated to be positive.

(Results)

The compound 1a did not induce an increase in the revertant colony, such as that exceeding 2 times the solvent control value, in any strain. In contrast, compound 1A induced a distinct increase in the revertant colony both in TA98 and TA2637, which exceeds 2 times the solvent control value, irrespective of metabolism activation.

From the above results, it has been concluded that compound 1a is mutagenicity negative, and compound 1A is mutagenicity positive.

*

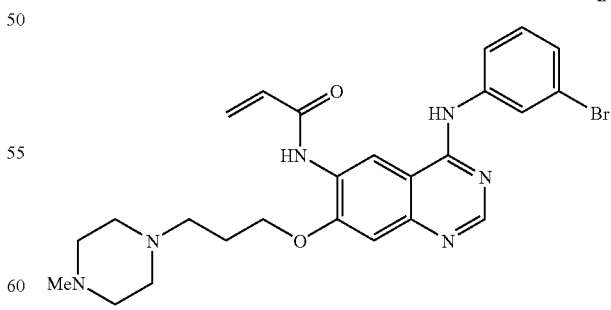

1A

INDUSTRIAL APPLICABILITY

Since the compound (I) of the present invention has a potent tyrosine kinase inhibitory activity (cancer cell growth inhibitory action), it can be used as an anticancer agent as well as an agent for the treatment and/or prophylaxis of psoriasis and the diseases based on arteriosclerosis.

This application is based on patent application Nos. 45827/2001 and 353525/2001 filed in Japan, the contents of which are all hereby incorporated by reference.

What is claimed is:

1. A quinazoline derivative of the following formula (1a)

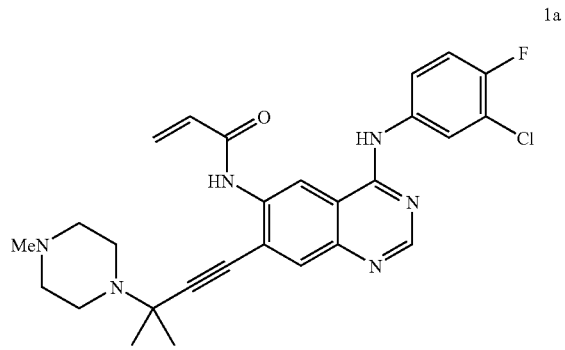

or a pharmaceutically acceptable salt thereof, a hydrate thereof, an optically active compound thereof, a racemate thereof or a diastereomer mixture thereof.

2. The quinazoline derivative of claim 1, wherein the pharmaceutically acceptable salt is a salt with tosic acid.

3. A crystal of a salt with tosic acid of a compound of the following formula (1a)

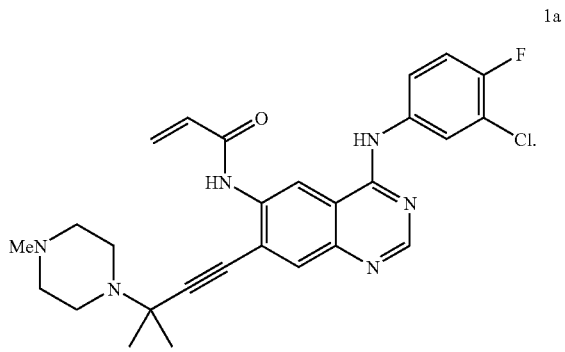

4. The crystal of claim 3 having any one, two, three, four, five, six or all the characteristic absorbance peaks (2θ) shown below in powder X-ray diffraction pattern:

characteristic peaks (2θ, ±0.2°) 33°, 6.6°, 7.5°, 94°, 13.9°, 17.4°, 19.1°.

5. The quinazoline derivative of claim 1, wherein the hydrate is a ½ hydrate.

6. A crystal of a ½ hydrate of a crystal of a compound of the following formula (1a)

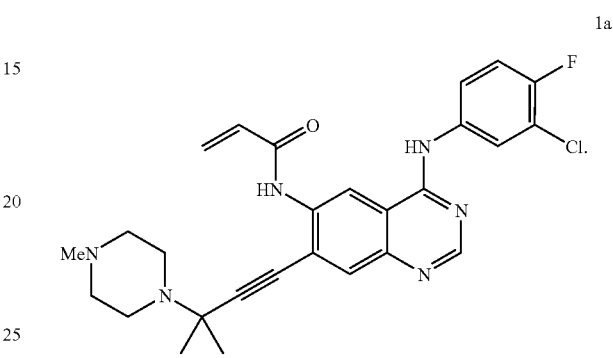

7. The crystal of claim 6 having any one, two, three, four, five, six or all the characteristic absorbance peaks (2θ) shown below in powder X-ray diffraction pattern:

characteristic peaks (2θ, ±0.2°) 7.1°, 10.6°, 11.9°, 12.2°, 13.8°, 17.3°, 18.4°.

8. A pharmaceutical composition comprising a quinazoline derivative of claim 1 and a pharmaceutically acceptable carrier.

9. A method for the treatment of a solid tumor, which comprises administering to a patient in need thereof a therapeutically effective amount of a quinazoline derivative of claim 1 as an active ingredient.

* * * * *